United States Patent
Killeen et al.

(10) Patent No.: US 12,012,441 B2
(45) Date of Patent: Jun. 18, 2024

(54) ENGINEERED HUMAN IL-21 CYTOKINES AND METHODS FOR USING THE SAME

(71) Applicant: Neptune Biosciences LLC, Newark, CA (US)

(72) Inventors: Nigel Killeen, Hillsborough, CA (US); Oren Beske, Aromas, CA (US); Benedikt K. Vollrath, San Diego, CA (US); Sridhar Govindarajan, Los Altos, CA (US)

(73) Assignee: Neptune Biosciences LLC, Newark, CA (US)

( * ) Notice: Subject to any disclaimer, the term of this patent is extended or adjusted under 35 U.S.C. 154(b) by 0 days.

(21) Appl. No.: 18/304,172

(22) Filed: Apr. 20, 2023

(65) Prior Publication Data

US 2023/0382967 A1   Nov. 30, 2023

Related U.S. Application Data

(63) Continuation-in-part of application No. PCT/US2021/056439, filed on Oct. 25, 2021.

(60) Provisional application No. 63/333,085, filed on Apr. 20, 2022, provisional application No. 63/333,090, filed on Apr. 20, 2022, provisional application No. 63/212,547, filed on Jun. 18, 2021, provisional application No. 63/105,414, filed on Oct. 26, 2020.

(51) Int. Cl.
*A61K 38/20* (2006.01)
*C07K 14/54* (2006.01)

(52) U.S. Cl.
CPC .................................. *C07K 14/54* (2013.01)

(58) Field of Classification Search
CPC . C07K 14/54; C12N 2501/2321; A61K 38/20
See application file for complete search history.

(56) References Cited

U.S. PATENT DOCUMENTS

| | | | |
|---|---|---|---|
| 6,057,128 A | 5/2000 | Donaldson et al. |
| 6,307,024 B1 | 10/2001 | Novak et al. |
| 6,576,744 B1 | 6/2003 | Presnell et al. |
| 6,586,251 B2 | 7/2003 | Economides et al. |
| 6,777,539 B2 | 8/2004 | Sprecher et al. |
| 6,803,451 B2 | 10/2004 | Presnell et al. |
| 6,812,339 B1 | 11/2004 | Venter et al. |
| 6,929,932 B2 | 8/2005 | Presnell et al. |
| 7,189,400 B2 | 3/2007 | Carter et al. |
| 7,198,789 B2 | 4/2007 | Carter et al. |
| 7,276,478 B2 | 10/2007 | Sivakumar et al. |
| 7,314,623 B2 | 1/2008 | Grusby et al. |
| 7,381,794 B2 | 6/2008 | Moore et al. |
| 7,495,085 B2 | 2/2009 | Valge-Archer et al. |
| 7,592,427 B2 | 9/2009 | Sivakumar et al. |
| 7,910,105 B2 | 3/2011 | Young et al. |
| 7,959,908 B2 | 6/2011 | Nelson et al. |
| 7,998,468 B2 | 8/2011 | Novak et al. |
| 8,110,180 B2 | 2/2012 | Novak et al. |
| 8,163,884 B2 | 4/2012 | Bloom et al. |
| 8,178,097 B2 | 5/2012 | Bloom et al. |
| 8,211,420 B2 | 7/2012 | Bondensgaard et al. |
| 8,383,367 B2 | 2/2013 | Hjorth et al. |
| 8,450,459 B2 | 5/2013 | Peschke et al. |
| 8,475,784 B2 | 7/2013 | Hjorth et al. |
| 8,586,006 B2 | 11/2013 | Hood et al. |
| 8,647,822 B2 | 2/2014 | Sekaly et al. |
| 9,200,058 B2 | 12/2015 | Park et al. |
| 9,254,311 B2 | 2/2016 | Bancel et al. |
| 9,309,318 B2 | 4/2016 | Gavin et al. |
| 10,105,442 B2 | 10/2018 | Coppieters et al. |
| 10,336,810 B2 | 7/2019 | Tanaka et al. |
| 10,596,274 B2 | 3/2020 | Frost et al. |
| 10,869,887 B2 | 12/2020 | Garcia et al. |
| 11,053,293 B2 | 7/2021 | Krupnick et al. |
| 11,136,562 B2 | 10/2021 | Taunton et al. |
| 11,291,721 B2 | 4/2022 | Loew et al. |
| 11,439,664 B2 | 9/2022 | Garcia et al. |
| 11,541,103 B2 | 1/2023 | Ali et al. |

(Continued)

FOREIGN PATENT DOCUMENTS

| | | |
|---|---|---|
| CA | 3123392 A1 | 6/2020 |
| EP | 1881070 A2 | 1/2008 |
| EP | 2746292 A1 | 6/2014 |
| EP | 2746293 A1 | 6/2014 |
| EP | 3254687 A1 | 12/2017 |
| EP | 3458485 B1 | 12/2021 |

(Continued)

OTHER PUBLICATIONS

UniProt Accession No. G1RE48_NOMILE, *Nomascus leucogenys* (Northern white-cheeked gibbon) (*Hylobates leucogenys*) IL21 Protein, Oct. 19, 2011 [online]. [Retrieved on Jul. 28, 2023]. Retrieved from the internet: <URL: https://www.uniprot.org/uniprotkb/G1RE48/entry> Entire document.

(Continued)

*Primary Examiner* — Dong Jiang
(74) *Attorney, Agent, or Firm* — Benjamen E. Kern; Charlemagne Kern; Kern Kendrick, LLC

(57) ABSTRACT

Orthogonal IL-21 receptors and orthogonal IL-21 cytokines are described. The IL-21 receptor-cytokine pairs may include an orthogonal interleukin-21 receptor α chain ("ortho-IL-21Rα") that has impaired binding to native interleukin-21 cytokine ("IL-21") and an orthogonal IL-21 cytokine ("ortho-IL-21") that has impaired binding to native IL-21Rα, wherein the ortho-IL-21Rα binds to the ortho-IL-21. The IL-21 receptor-cytokine pair may activate IL-21 signaling. Cells engineered to express the orthogonal IL-21 receptors are also described, as well as methods for using such cells for treatment of various diseases and disorders.

18 Claims, 41 Drawing Sheets

Specification includes a Sequence Listing.

(56) References Cited

U.S. PATENT DOCUMENTS

| | | |
|---|---|---|
| 11,629,340 B2 | 4/2023 | Suri et al. |
| 2005/0124044 A1 | 6/2005 | Cunningham et al. |
| 2006/0024268 A1 | 2/2006 | Kasaian et al. |
| 2006/0039902 A1 | 2/2006 | Young et al. |
| 2006/0159655 A1 | 7/2006 | Collins et al. |
| 2006/0281146 A1 | 12/2006 | Bodary et al. |
| 2007/0048301 A1 | 3/2007 | Bodary-Winter et al. |
| 2007/0184444 A1 | 8/2007 | Abbas et al. |
| 2007/0274990 A1 | 11/2007 | Morris et al. |
| 2010/0075329 A1 | 3/2010 | O'Toole et al. |
| 2013/0224109 A1 | 8/2013 | Strom et al. |
| 2013/0323259 A1 | 12/2013 | Svensson et al. |
| 2015/0030562 A1 | 1/2015 | Leonard et al. |
| 2018/0125890 A1 | 5/2018 | Anderson et al. |
| 2019/0046611 A1 | 2/2019 | Ali et al. |
| 2019/0119345 A1 | 4/2019 | Krupnick et al. |
| 2019/0183933 A1 | 6/2019 | Garcia et al. |
| 2019/0391152 A1 | 12/2019 | Abrignani et al. |
| 2020/0316118 A1 | 10/2020 | Jounaidi et al. |
| 2021/0069243 A1 | 3/2021 | Garcia et al. |
| 2021/0163562 A1 | 6/2021 | Lu et al. |
| 2021/0260162 A1 | 8/2021 | Gonzalez et al. |
| 2022/0025006 A1 | 1/2022 | Zhang et al. |
| 2022/0213452 A1 | 7/2022 | Taunton et al. |
| 2022/0296644 A1 | 9/2022 | Garcia et al. |
| 2022/0354893 A1 | 11/2022 | Garcia et al. |

FOREIGN PATENT DOCUMENTS

| | | | |
|---|---|---|---|
| TW | 201531482 A | | 8/2015 |
| WO | 2000017235 A2 | | 3/2000 |
| WO | 2001036467 A2 | | 5/2001 |
| WO | 2001085792 A2 | | 11/2001 |
| WO | 2009100035 A2 | | 8/2009 |
| WO | 2015110930 | | 7/2015 |
| WO | 2017044464 A1 | | 3/2017 |
| WO | 2017120546 A1 | | 7/2017 |
| WO | 2018160993 A1 | | 9/2018 |
| WO | 2018182935 A1 | | 10/2018 |
| WO | 2019028316 | | 2/2019 |
| WO | 2019028419 A1 | | 2/2019 |
| WO | 2019157130 A1 | | 8/2019 |
| WO | 2019246508 | | 12/2019 |
| WO | 2021253360 | | 12/2021 |
| WO | 2022135469 A1 | | 6/2022 |

OTHER PUBLICATIONS

International Search Report and Written Opinion issued in PCT/US21/56439 on Mar. 2, 2022.

International Preliminary Report on Patentability issued in PCT/US21/56439 on Mar. 2, 2022.

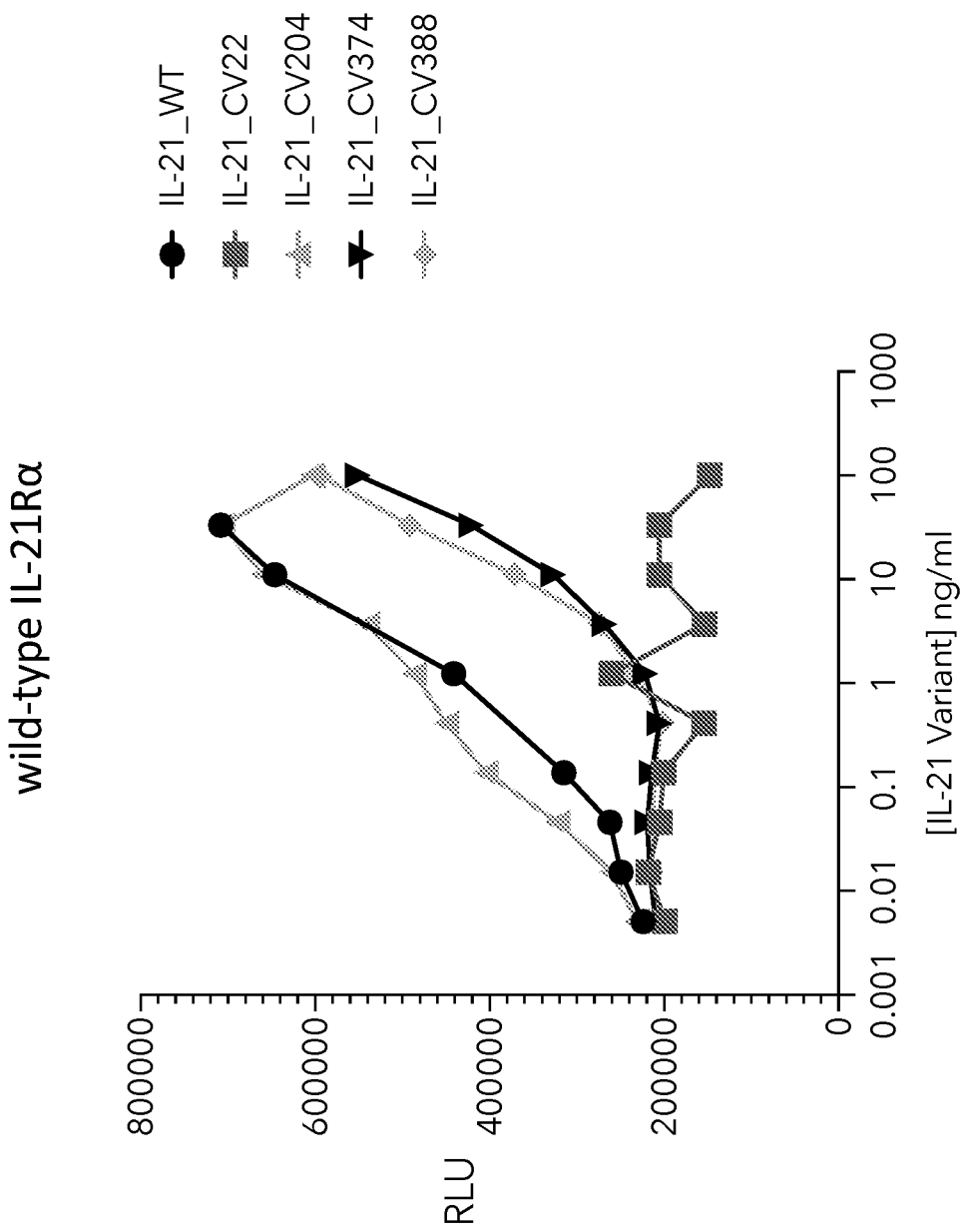

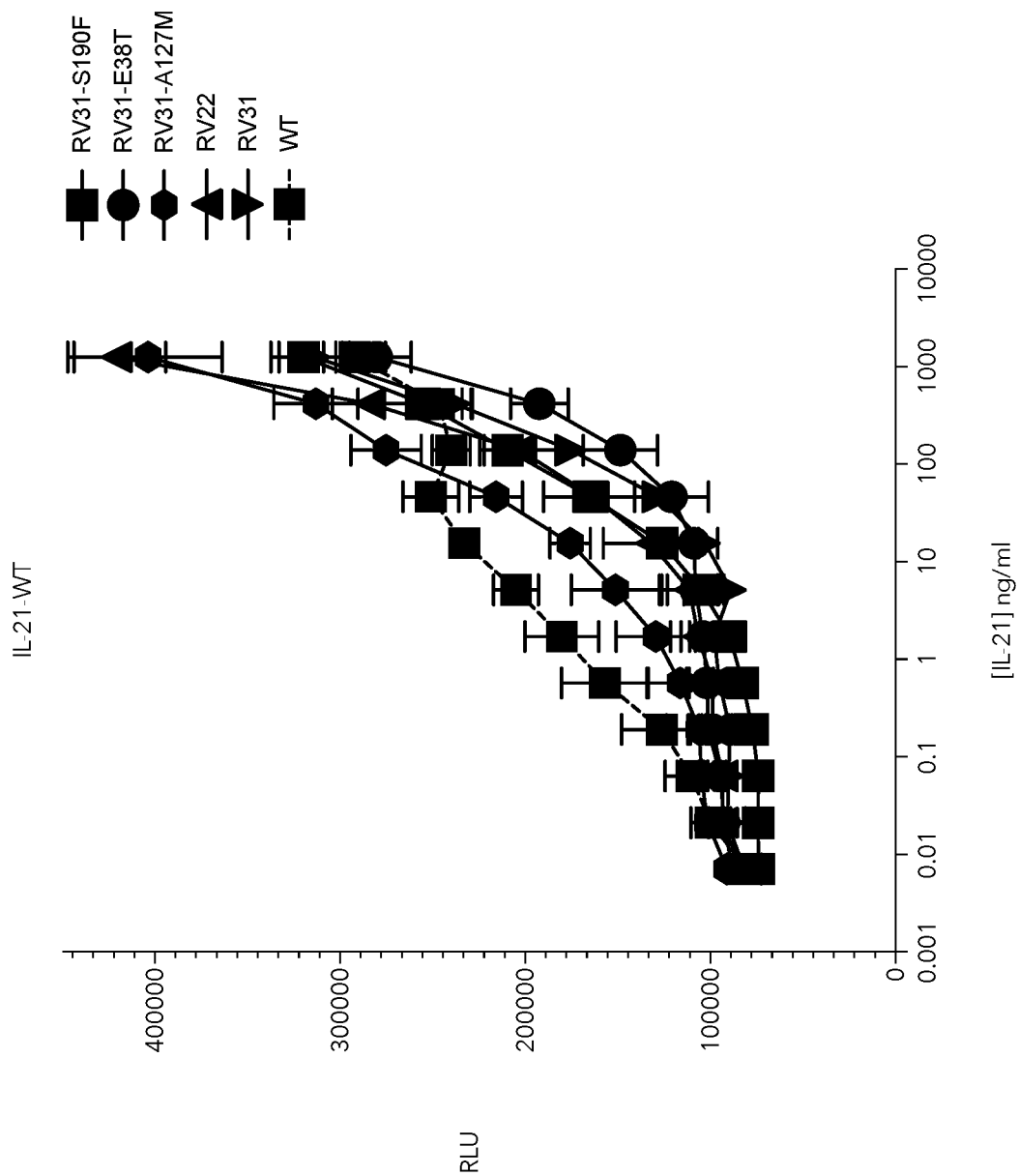

ENGINEERED HUMAN IL-21 CYTOKINES AND METHODS FOR USING THE SAME

CROSS-REFERENCE TO RELATED APPLICATIONS

This application is a continuation-in-part of International Application No. PCT/US21/56439, filed on Oct. 25, 2021, which claims the benefit of U.S. Provisional Patent Application No. 63/105,414, filed on Oct. 26, 2020, and U.S. Provisional Patent Application No. 63/212,547, filed on Jun. 18, 2021. This application also claims the benefit of U.S. Provisional Patent Application No. 63/333,085, filed on Apr. 20, 2022, and U.S. Provisional Patent Application No. 63,333,090, filed on Apr. 20, 2022. Each of these applications is incorporated by reference herein in its entirety.

SEQUENCE LISTING

A Sequence Listing has been submitted electronically in XML format and is hereby incorporated by reference in its entirety. The XML copy, created on Apr. 20, 2023, is named IL21_ST26.xml and is 187,241 bytes in size.

BACKGROUND

Cytokines are potent natural regulators of immune cell proliferation and differentiation. While this potency has made cytokines highly attractive as potential therapeutics, it has also complicated their clinical utility. This has been especially true for cytokines that have multiple cellular targets and, thus, high potential for pleiotropic effects. One example is Interleukin-2 ("IL-2"), a robust T cell mitogen whose anti-cancer activity is offset by unwanted proliferation of regulatory (suppressor) T cells and a painful vascular leak syndrome. In the specific case of IL-2, protein engineering can be used to solve some of the clinical challenges: removing, for example, the cytokine's capacity to act preferentially on regulatory T cells. An alternative approach involves generating orthogonally constrained forms of cytokines and their receptors. See U.S. Pat. No. 10,869,887; Sockolosky J T, Trotta E, Parisi G, et al. Selective targeting of engineered T cells using orthogonal IL-2 cytokine-receptor complexes. *Science.* 2018; 359(6379): 1037-1042. doi: 10.1126/science.aar3246, the disclosure of each of which is incorporated by reference herein in its entirety.

An orthogonal cytokine system is one in which a cytokine and its receptor have been mutated such that they lose compatibility with their native (parental) partners yet retain the capacity to interact productively with one another. Such an orthogonal cytokine:receptor pair can thus be said to demonstrate "privileged" or "private" interactions. The approach of generating orthogonally constrained forms of cytokines and their receptors is of value for cell therapy because it provides a way to limit the scope of a cytokine's activity solely to the therapeutic (i.e., adoptively transferred) cells—these being the only cells expressing the engineered receptor and, consequently, the only cells capable of responding to the engineered cytokine.

Interleukin-21 ("IL-21") is another pleiotropic cytokine with actions in a broad range of lymphoid, myeloid, and epithelial cells. IL-21 regulates both innate and adaptive immune responses; it not only has key roles in antitumor and antiviral responses, but also exerts major effects on inflammatory responses that promote the development of autoimmune diseases and inflammatory disorders. Spolski, R., Leonard, W. Interleukin-21: a double-edged sword with therapeutic potential. Nat Rev Drug Discov 13, 379-395 (2014). https://doi.org/10.1038/nrd4296. The three-dimensional structure of the natural human IL-21 cytokine:receptor complex is known. See Hamming O J, Kang L, Svensson A, et al. Crystal structure of interleukin-21 receptor (IL-21R) bound to IL-21 reveals that sugar chain interacting with WSXWS motif is integral part of IL-21R. *J Biol Chem.* 2012; 287(12):9454-9460. doi:10.1074/jbc.M111.311084, the disclosure of which is incorporated by reference herein in its entirety.

IL-21 is of particular interest because it enhances cytotoxic T cell responses to viruses and tumors and can act in synergy with other cytokines, such as IL-2 or IL-15. IL-21 does this in part by promoting the persistence of T cells with a stem cell memory phenotype, which has been associated with beneficial outcomes in cell therapy settings. IL-21 is currently undergoing evaluation as a cancer therapeutic in multiple clinical trials. IL-21 also has significant potential utility in chimeric antigen receptor T ("CAR-T") cell therapies, where it may help to overcome clinical failures due to poor expansion, anti-tumor efficacy, exhaustion, suppression, and persistence. Thus, an urgent need exists for the ability to modulate the actions of IL-21, particularly by engineering into adoptively transferred cells a desired behavior that is protected from endogenous signaling pathways, that does not affect non-targeted endogenous cells, and that can be controlled once administered to a patient.

SUMMARY

In one aspect, an orthogonal interleukin-21 receptor alpha chain (an "ortho-IL-21Rα" or "ortho-IL-21Rα molecule," or when referring to a specific ortho-IL-21Rα constructed as provided herein, an "RV," as in "Receptor Variant") is provided, the ortho-IL-21Rα comprising a modified amino acid sequence derived from SEQ ID NO: 1 that binds to an orthogonal interleukin-21 cytokine (an "ortho-IL-21" or "ortho-IL-21 molecule," or when referring to a specific ortho-IL-21 constructed as provided herein, a "CV," as in "Cytokine Variant") but has impaired binding to native IL-21. In one aspect, the ortho-IL-21Rα comprises a modified amino acid sequence comprising a substitution of one or more amino acid residues of SEQ ID NO: 1 that contact IL-21, residues in the immediate vicinity of such contact residues, or residues elsewhere in IL-21Rα that have an influence on the conformation of the IL-21 binding surface. In one aspect, the ortho-IL-21Rα comprises an amino acid substitution, numbered relative to SEQ ID NO: 2 (the human IL-21Rα ectodomain in mature form lacking the signal peptide), at position: Q33, E38, M70, D73, A127, Y129, S190, and combinations thereof. In one aspect, the amino acid substitution comprises, consists essentially of, or consists of: M70G, M70I, D73E, Q33H, E38T, E38H, Y129F, S190F, A127M, and combinations thereof. In one aspect, the amino acid substitution comprises, consists essentially of, or consists of: M70G/Y129F ("RV13," as in "Receptor Variant 13," or SEQ ID NO: 3), M70G ("RV22" or SEQ ID NO: 4), M70I/D73E/Q33H ("RV6" or SEQ ID NO: 5), M70I/D73E ("RV31" or SEQ ID NO: 6), M70I/D73E/E38T ("RV31-E38T" or SEQ ID NO: 85), M70I/D73E/E38H ("RV31-E38H" or SEQ ID NO: 86), M70I/D73E/S190F ("RV31-S190F" or SEQ ID NO: 87), M70I/D73E/A127M (RV31-A127M, or SEQ ID NO: 88), M70I/D73E/S190F/A127M/E38T ("RV31-S190F/A127M/E38T" or SEQ ID NO: 95). M70I/D73E/S190F/A127M/E38H ("RV31-S190F/A127M/E38H" or SEQ ID NO: 96), M70I/D73E/S190F/E38T ("RV31-S190F/E38T" or SEQ ID NO: 97), M70I/D73E/

S190F/E38H ("RV31-S190F/E38H" or SEQ ID NO: 98), M70I/D73E/A127M/E38H ("RV31-A127M/E38T" or SEQ ID NO: 99), M70I/D73E/A127M/E38H ("RV31-A127M/E38T" or SEQ ID NO: 100), or M70I/D73E/S190F/A127M ("RV31-S190F/A127M" or SEQ ID NO: 101). In one aspect, RV13 and RV22 may be substituted in the same manner as RV31, i.e., at positions S190, A127, and E38.

In another aspect, parallel mutually orthogonal systems that do not demonstrate crosstalk with each other or with wild-type IL-21 or IL-21Rα are provided.

In another aspect, an ortho-IL-21 or engineered human IL-21 polypeptide (these phrases are used interchangeably herein) is provided, the ortho-IL-21 comprising a modified amino acid sequence derived from SEQ ID NO: 7 that binds to an ortho-IL-21Rα but has impaired binding to native IL-21Rα. In one aspect, the ortho-IL-21 comprises a modified amino acid sequence comprising a substitution of one or more amino acid residues of SEQ ID NO: 7 that contact IL-21Rα, residues in the immediate vicinity of such contact residues, or residues elsewhere in IL-21 that have an influence on the conformation of the IL-21Rα binding surface. In one aspect, the ortho-IL-21 comprises an amino acid substitution, numbered relative to SEQ ID NO: 7, at position: H6, R9, M10, R11, I16, Q19, I66, K73, R76, P78, S80, G84, or P104, and combinations thereof. The phrase "numbered relative to SEQ ID NO: 7" means, for numbering purposes, to disregard any epitope tags and signaling peptides. In one aspect, the amino acid substitution comprises, consists essentially of, or consists of: H6L, R9K, M10L, R11S, R11T, I16V, Q19F, I66S, K73V, K73L, K73M, K73I, R76K, R76H, P78L, S80K, S80L, G84E, P104I, or P104A, and combinations thereof.

In one aspect, the ortho-IL-21 comprises amino acid substitutions, numbered relative to SEQ ID NO: 7: H6L/M10L/P78L. In another aspect, the ortho-IL-21 further comprises amino acid substitution R9K. In another aspect, the ortho-IL-21 further comprises amino acid substitution G84E. In another aspect, the ortho-IL-21 further comprises one of amino acid substitution P104V or P104A. In another aspect, the ortho-IL-21 further comprises one of amino acid substitution K73V or K73I. In one aspect, such an ortho-IL-21 may include SEQ ID NO: 8 (CV374: H6L/R9K/M10L/K73V/P78L/G84E), SEQ ID NO: 9 (CV388: H6L/R9K/M10L/K73I/P78L/P104A), SEQ ID NO: 10 (CV414: H6L/R9K/M10L/K73I/P78L), or SEQ ID NO: 11 (CV415: H6L/R9K/M10L/K73I/P78L/G84E/P104V).

In one aspect, an engineered human IL-21 polypeptide is provided that comprises amino acid substitutions, numbered relative to SEQ ID NO: 7: H6L/M10L/P78L. In another aspect, the engineered human IL-21 polypeptide further comprises one of amino acid substitution S80P, S80K, or S80V. In another aspect, the engineered human IL-21 polypeptide further comprises amino acid substitution G84E. In another aspect, the engineered human IL-21 polypeptide further comprises one of amino acid substitution P104I or P104A. In another aspect, the engineered human IL-21 polypeptide further comprises one of amino acid substitution K73V, K73L, or K73M. In another aspect, the engineered human IL-21 polypeptide further comprises one of amino acid substitution R76H or R76K. In another aspect, the engineered human IL-21 polypeptide further comprises one of amino acid substitution R11S or R11T. In another aspect, the engineered human IL-21 polypeptide further comprises amino acid substitution I16V. In another aspect, the engineered human IL-21 polypeptide further comprises amino acid substitution Q19F. In another aspect, the engineered human IL-21 polypeptide further comprises amino acid substitution I66S. In one aspect, such an engineered human IL-21 polypeptide may include SEQ ID NO: 12 (CV339: H6L/M10L/K73V/R76K/P104A), SEQ ID NO: 13 (CV425: H6L/M10L/K73L/P78L), SEQ ID NO: 14 (CV431: H6L/M10L/K73M/R76H/P78L/G84E), SEQ ID NO: 15 (CV458: H6L/M10L/K73L/P78L/S 80P/P104A), SEQ ID NO: 82 (CV588: H6L/M10L/R11S/I16V/K73L/R76H/P78L), SEQ ID NO: 83 (CV617: H6L/M10L/R11S/I16V/Q19F/I66S/K73L/R76H/P78L/S80K), or SEQ ID NO: 84 (CV631: H6L/M10L/R11T/I16V/K73L/R76H/P78L/S80V/P104I).

In another aspect, parallel mutually orthogonal systems that do not demonstrate crosstalk with each other or with wild-type IL-21 or IL-21Rα are provided.

In another aspect, a system for activating IL-21 signaling in a cell is provided, the system comprising: an ortho-IL-21Rα that has impaired binding to native IL-21, the ortho-IL-21Rα comprising a modified amino acid sequence derived from SEQ ID NO: 1 comprising a substitution of one or more of the amino acid residues of SEQ ID NO: 1 that contact IL-21, residues in the immediate vicinity of such contact residues, or residues elsewhere in IL-21Rα that have an influence on the conformation of the IL-21 binding surface; and an ortho-IL-21 that has impaired binding to native IL-21Rα, the ortho-IL-21 comprising a modified amino acid sequence derived from SEQ ID NO: 7 comprising a substitution of one or more amino acid residues of SEQ ID NO: 7 that contact IL-21Rα, residues in the immediate vicinity of such contact residues, or residues elsewhere in IL-21 that have an influence on the conformation of the IL-21Rα binding surface, wherein the ortho-IL-21Rα binds to the ortho-IL-21. In one aspect, the cell is a mammalian cell, an immune cell, a stem cell, or a T cell.

BRIEF DESCRIPTION OF THE FIGURES

The present invention may be more readily understood by reference to the following figures, wherein:

FIGS. 4A-C show luminometry data for individual plates in which, in each case, the binding of IL-21-TLuc16 to five candidate ortho-IL-21Rα molecules and a wild-type control IL-21Rα was compared. Several of the candidate ortho-IL-21Rα molecules showed significantly diminished capacity to bind IL-21-TLuc16 relative to the wild-type control.

FIGS. 5A and 5B show IL-21-induced STAT3 signaling responses by Ba/F3 cells expressing native IL-21Rα and eight candidate ortho-IL-21Rα molecules, including RV6 and RV13. The cells carried a STAT3-regulated *Cypridina noctiluca* luciferase reporter transgene; they were exposed to different concentrations of native IL-21 overnight (approximately 20 hours) before testing the supernatant medium for luciferase activity by luminometry, with Vargulin serving as the enzyme substrate. Cells expressing a form of wild-type IL-21Rα lacking its cytoplasmic tail (Δcyt) were included to show that STAT3 signaling in response to IL-21 depended on the cytoplasmic tail of the receptor, as expected.

FIG. 6A-6D show the capacity of native IL-21 and selected candidate ortho-IL-21 molecules, including two, for example, that each comprise one amino acid substitution, numbered relative to SEQ ID NO: 7, at R9K (CV9; SEQ ID NO: 16) and K73V (CV14; SEQ ID NO: 17), to induce signaling via native IL-21Rα and RV13. As described with respect to FIGS. 5A and 5B, luminometry was used to quantify luciferase produced by transfected Ba/F3 cells carrying a STAT3-dependent luciferase reporter transgene resident on the same transposon used to confer expression of native IL-21Rα or candidate ortho-IL-21Rα molecules. The cells were exposed to increasing concentrations of the candidate ortho-IL-21 molecules overnight (approximately 20 hours) before testing the supernatant culture medium for luciferase activity.

FIGS. 7A-7D show the capacity of native IL-21 and CV14 to induce signaling via native IL-21Rα and RV13. B a/F3 cells (expressing native IL-21Rα or CV14 from a transposon that also carried a STAT3-luciferase reporter transgene) were exposed to increasing concentrations of native IL-21Rα and RV13 (for approximately 20 hours) before recovering supernatant medium and testing it for luciferase activity by luminometry as in FIGS. 5A and B and 6A-6D.

FIGS. 8A, 8B, and 8C show the results of a representative screening experiment in which a collection of 96 cytokines were tested for their capacity to induce STAT3-dependent signaling responses in B a/F3 cells expressing wild-type IL-21Rα (FIG. 8A) or the candidate ortho-IL-21Rα molecules RV13 (FIG. 8B) or RV6 (FIG. 8C). As described with respect to FIGS. 5A and B and 6A-6D, luminometry was used to quantify luciferase produced by transfected Ba/F3 cells carrying a STAT3-dependent luciferase reporter transgene resident on the same transposon used to confer expression of native IL-21Rα or the candidate ortho-IL-21Rα molecule. The cells were exposed to increasing concentrations of the candidate ortho-IL-21 molecules overnight (approximately 20 hours) before testing the supernatant culture medium for luciferase activity. The dotted lines show response curves for the cytokine collection, while the responses caused by five cytokines of interest (wild-type IL-21, negative control CV22 comprising amino acid substitutions R5Q/R76A (SEQ ID NO: 18), and candidate ortho-IL-21 molecules CV204 comprising amino acid substitutions H6L/M10L/K73V/P78L/P104A (SEQ ID NO: 19), CV374, and CV388 are highlighted with solid lines and symbols.

FIGS. 9A and 9B show the relative capacity of native IL-21, CV22, CV204, CV374, and CV388 to induce signaling via wild-type IL-21Rα (FIG. 9A) and the candidate ortho-IL-21Rα RV13 (FIG. 9B). As described with respect to FIGS. 5A and B and 6A-6D, luminometry was used to quantify luciferase produced by transfected Ba/F3 cells carrying a STAT3-dependent luciferase reporter transgene resident on the same transposon used to confer expression of native IL-21Rα or RV13. The cells were exposed to increasing concentrations of the candidate ortho-IL-21 molecules overnight (approximately 20 hours) before testing the supernatant culture medium for luciferase activity.

FIGS. 10A, 10B, and 10C show the capacity of native IL-21, CV22, CV204, CV374, and CV388 to induce signaling via wild-type IL-21Rα (FIG. 10A), the candidate ortho-IL-21Rα RV13 (FIG. 10B), and the candidate ortho-IL-21Rα RV22 (FIG. 10C). Responses elicited by wild-type IL-21 and 95 variants are represented in each figure, with the five indicated response curves highlighted. As described with respect to FIGS. 5A and B and 6A-6D, luminometry was used to quantify luciferase produced by transfected Ba/F3 cells carrying a STAT3-dependent luciferase reporter transgene resident on the same transposon used to confer expression of native IL-21Rα or the candidate ortho-IL-21Rα molecule. The cells were exposed to increasing concentrations of the candidate ortho-IL-21 molecules overnight (approximately 20 hours) before testing the supernatant culture medium for luciferase activity.

FIGS. 11A and 11B show the capacity of native IL-21 and candidate ortho-IL-21 molecules CV374 and CV415 to induce signaling via wild-type IL-21Rα (FIG. 11A) or the candidate ortho-IL-21Rα molecule RV22 (FIG. 11B). Responses elicited by wild-type IL-21 and 95 variants are represented in each figure, with the three indicated response curves highlighted. FIG. 11C shows a comparison of the responses elicited by wild-type IL-21 or the candidate ortho-IL-21 molecule CV415 on cells expressing wild-type IL-21Rα or the candidate ortho-IL-21Rα molecule RV22. As described with respect to FIGS. 5A and B and 6A-6D, luminometry was used to quantify luciferase produced by transfected Ba/F3 cells carrying a STAT3-dependent luciferase reporter transgene resident on the same transposon used to confer expression of native IL-21Rα or the candidate ortho-IL-21Rα molecule. The cells were exposed to increasing concentrations of the candidate ortho-IL-21 molecules overnight (approximately 20 hours) before testing the supernatant culture medium for luciferase activity.

FIGS. 12A-12C show the capacity of native IL-21 and candidate ortho-IL-21 molecules CV374, CV415, CV425, CV431, CV458, and CV339 to induce signaling via wild-type IL-21Rα (FIG. 12A), the candidate ortho-IL-21Rα molecule RV22 (FIG. 12B), or the candidate ortho-IL-21Rα molecule RV31 (FIG. 12C). Responses elicited by wild-type IL-21 and 95 variants are represented in each figure, with the indicated response curves highlighted. FIG. 12D shows a comparison of the responses elicited by wild-type IL-21 or the indicated candidate ortho-IL-21 variants on cells expressing wild-type IL-21Rα or the candidate ortho-IL-21Rα molecule RV31. As described with respect to FIGS. 5A and B and 6A-6D, luminometry was used to quantify luciferase produced by transfected Ba/F3 cells carrying a STAT3-dependent luciferase reporter transgene resident on the same transposon used to confer expression of native IL-21Rα or the candidate ortho-IL-21Rα molecule. The cells were exposed to increasing concentrations of the candidate ortho-IL-21 molecules overnight (approximately 20 hours) before testing the supernatant culture medium for luciferase activity.

FIGS. 13A-13J show the capacity of native IL-21 (IL-21-WT, FIGS. 13A and 13F) and candidate ortho-IL-21 molecules CV415 (FIGS. 13B and 13G), CV588 (FIGS.

13C and 13H), CV617 (FIGS. 13D and 13I), and CV631 (FIGS. 13E and 13J) to induce signaling via wild-type IL-21Rα, the candidate ortho-IL-21Rα molecule RV22, the candidate ortho-IL-21Rα molecule RV31, and four variants of RV31 (M70/D73E) bearing an additional E38T (RV31-E38T), E38H (RV31-E38H), S190F (RV31-S190F), or A127M (RV31-A127M) substitution. In FIGS. 13A-13E, a *Cypridina* luciferase reporter was used to detect STAT3 activation, whereas a *Gaussia* luciferase reporter was used for the same purpose in FIGS. 13F-13J. In all cases, the cells were exposed to different concentrations of the indicated ortho-IL-21 cytokines (or native IL-21) overnight (approximately 20 hours) before testing the supernatant culture medium for luciferase activity by luminometry using either vargulin or coelenterazine as luciferase substrates. The assays were performed in quadruplicate using 384-well plates with approximately 50,000 cells in each well in a final volume of 60111.

DETAILED DESCRIPTION

Orthogonal IL-21 receptors and orthogonal IL-21 cytokines are provided. The orthogonal IL-21 receptor:cytokine pairs may include an ortho-IL-21Rα that has impaired binding to native IL-21 and an ortho-IL-21 that has impaired binding to native IL-21Rα, wherein the ortho-IL-21Rα binds to ortho-IL-21. The orthogonal IL-21 receptor-cytokine pair may be used to activate a signaling response in cells. The signaling response may be the native one normally downstream of the IL-21 receptor or an alternative one dependent on non-native IL-21 receptors and/or other non-native cellular components. Cells engineered to express the orthogonal IL-21 receptors are also provided, as well as methods for using such cells for treatment of various diseases and disorders.

Definitions

The terminology as set forth herein is for description only and should not be construed as limiting of the invention. As used in the description and the appended claims, the singular forms "a," "an," and "the" are inclusive of their plural forms, unless otherwise expressed.

"Treat," "treating," "treatment," and the like refer to any action providing a benefit to a subject afflicted with a disease or disorder such as cancer, including improvement in the condition through lessening or suppression of at least one symptom, delay in progression of the disease, and the like.

The phrases "effective amount" and "therapeutically effective amount" refer to an amount of the composition used in the practice of the invention that is sufficient to provide effective treatment in a subject.

"Wild type," "WT," and "native" are used interchangeably herein and mean an amino acid sequence or a nucleotide sequence that is found in nature, including allelic variations. A WT protein, polypeptide, antibody, immunoglobulin, IgG, and the like has an amino acid sequence or a nucleotide sequence corresponding to that normally found in nature, which has not been intentionally modified.

The term "polynucleotide" refers to oligonucleotides, nucleotides, or to a fragment of any of these; to DNA or RNA (e.g., mRNA, rRNA, tRNA) of genomic or synthetic origin, which may be single-stranded or double-stranded and may represent a sense or antisense strand; to peptide nucleic acids; or to any DNA-like or RNA-like material, whether natural or synthetic in origin. The term may also encompass nucleic acids, e.g., oligonucleotides, containing known analogs of natural nucleotides, as well as nucleic acid-like structures with synthetic backbones.

The term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs, and the like. A protein or peptide "chain" refers to a distinct subunit of a larger protein or protein complex.

By "homologs" is meant that the corresponding proteins (e.g., IL-21Rα), such as those from other species, are substantially homologous at the overall protein (i.e., mature protein) level to the human protein, so long as such homologous peptides retain their respective known activities. Various levels of homology, from 35% to 99%, can be present.

The term "amino acid modification" includes an amino acid substitution, insertion, or deletion in a polypeptide sequence. By "amino acid substitution" or "substitution" is meant the replacement of an amino acid at a particular position in a parent polypeptide sequence with another amino acid. For example, the substitution R94K refers to a modified polypeptide in which the arginine at position 94 is replaced with a lysine. For the preceding example, 94K indicates the substitution of position 94 with a lysine. Multiple substitutions are typically separated by a slash or a comma. For example, R94K/L78V and [R94K, L78V] refer to a double variant comprising the substitutions R94K and L78V. By "amino acid insertion" or "insertion" is meant the addition of an amino acid at a particular position in a parent polypeptide sequence, including an addition to a C- or N-terminus. For example, insert-94 designates an insertion at position 94. By "amino acid deletion" or "deletion" is meant the removal of an amino acid at a particular position in a parent polypeptide sequence. For example, R94- designates the deletion of arginine at position 94.

The phrases "conservative modifications" and "conservative sequence modifications" refer to amino acid modifications that do not significantly affect or alter the binding characteristics of the polypeptide containing the amino acid sequence. Such conservative modifications include amino acid substitutions, insertions, and deletions. Modifications can be introduced into a protein by standard techniques known in the art, such as site-directed mutagenesis and PCR-mediated mutagenesis, or by DNA synthesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine).

Ordinarily, the conservative substitution variants, homologs, and analogs of the peptides will have an amino acid sequence identity to the disclosed sequences of at least about 35%, at least about 45%, at least about 55%, at least about 65%, at least about 75%, at least about 80%, at least about 85%, at least about 90%, at least about 95%, or at least about 96% to 99%. Rost B. Twilight zone of protein sequence alignments. *Protein Eng.* 1999; 12(2):85-94. doi: 10.1093/protein/12.2.85.

Figure 1:
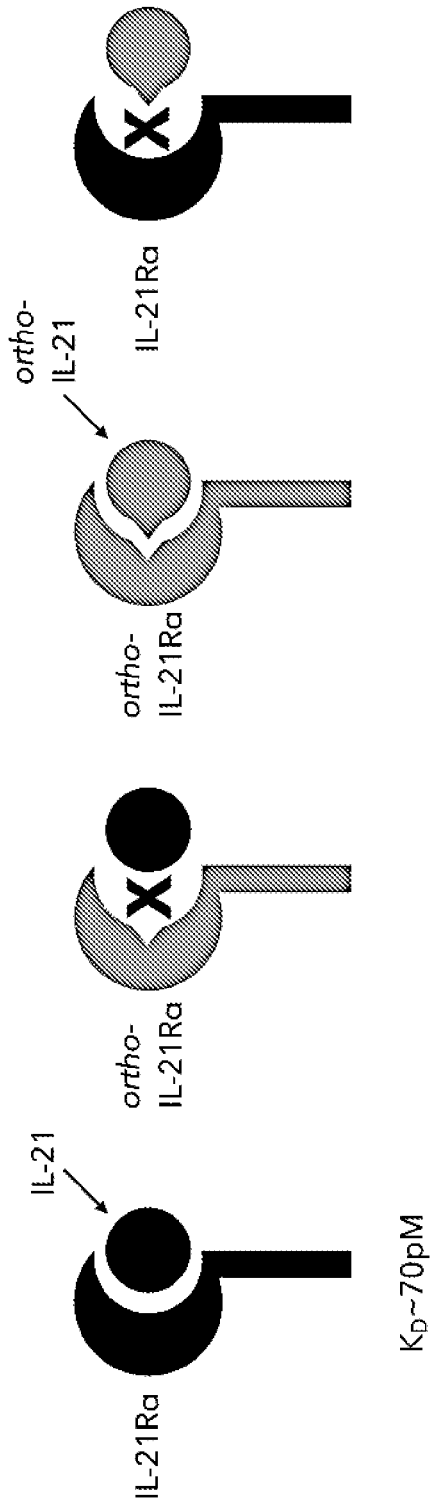
FIG. 1 provides a schematic representation of an orthogonal IL-21 system. The cartoon at the extreme left shows the wild-type receptor and cytokine interacting productively with one another, while the adjacent cartoon depicts the impaired interaction between an ortho-IL-21Rα and the native cytokine. The cartoon at the extreme right depicts the impaired interaction between ortho-IL-21 and the native (wild-type) receptor, while the adjacent cartoon shows a productive interaction between the two orthogonal molecules (ortho-IL-21Rα and ortho-IL-21).

Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal, or internal extensions, deletions, or insertions into the peptide sequence shall not be construed as affecting homology.

A gamma chain (γc) cytokine means any cytokine where the cognate cytokine receptor complex includes the common cytokine receptor gamma chain (γc). γc cytokines include IL-2, IL-4, IL-7, IL-9, IL-15 and IL-21.

An orthogonal cytokine:receptor pair refers to variants of a natural cytokine:receptor pair that interact effectively with one another (i.e., such that they can be used to initiate physiologically consequential signaling responses in cells) but are significantly impaired in their capacity to interact with their natural counterparts. The orthogonal cytokine can either be a mutated or otherwise modified natural cytokine (a "mutein") or a completely synthetic protein that acts as an agonist on the orthogonal cytokine receptor (sometimes referred to as a "synthekine"). The orthogonal cytokine (whether a mutein or a synthekine) shows no, or only attenuated, agonist activity toward the wild-type cytokine receptor.

Thus, the orthogonal cytokine:receptor pair may comprise a genetically engineered pair of proteins that are modified by amino acid changes to: (a) lack or reduce binding to the native cytokine or cognate receptor; and (b) specifically bind to the counterpart engineered (orthogonal) ligand or receptor. Upon binding of the orthogonal cytokine, the orthogonal receptor activates signaling that is transduced through native cellular elements to provide for a biological activity that mimics the native response, but that is specific to an engineered cell expressing the orthogonal receptor. Non-native receptor or cellular elements (e.g., non-native cytoplasmic domains in the receptor) can be involved to modify the signaling response. The orthogonal receptor does not bind to any endogenous cytokine or only does so with attenuated avidness, including the native counterpart of the orthogonal cytokine, while the orthogonal cytokine does not bind to any endogenous receptor or only does so with attenuated avidness, including the native counterpart of the orthogonal receptor. In some aspects, the affinity of the orthogonal cytokine for the orthogonal receptor is comparable to the affinity of the native cytokine for the native receptor, e.g., having an affinity that is at least about 1% of the native cytokine receptor pair affinity, at least about 5%, at least about 10%, at least about 25%, at least about 50%, at least about 75%, at least about 100%, and may be higher, e.g. 2×, 3×, 4×, 5×, 10× or more of the affinity of the native cytokine for the native receptor.

The term "candidate" when used in qualification of an orthogonal protein (IL-21 or IL-21Rα) infers a prototypic or developmental status. Analytical procedures may remove the qualification if a candidate protein is found to have the desired degree of binding privilege and orthogonal functionality.

As used herein, the phrases "does/do not bind" and "incapable of binding" refer to no detectable binding, or an insignificant binding, i.e., having a binding affinity much lower than that of the natural ligand. "Impaired binding" refers to binding that is lower than the normal level of binding between the corresponding wild-type components (e.g., cytokine and receptor).

Figure 2:
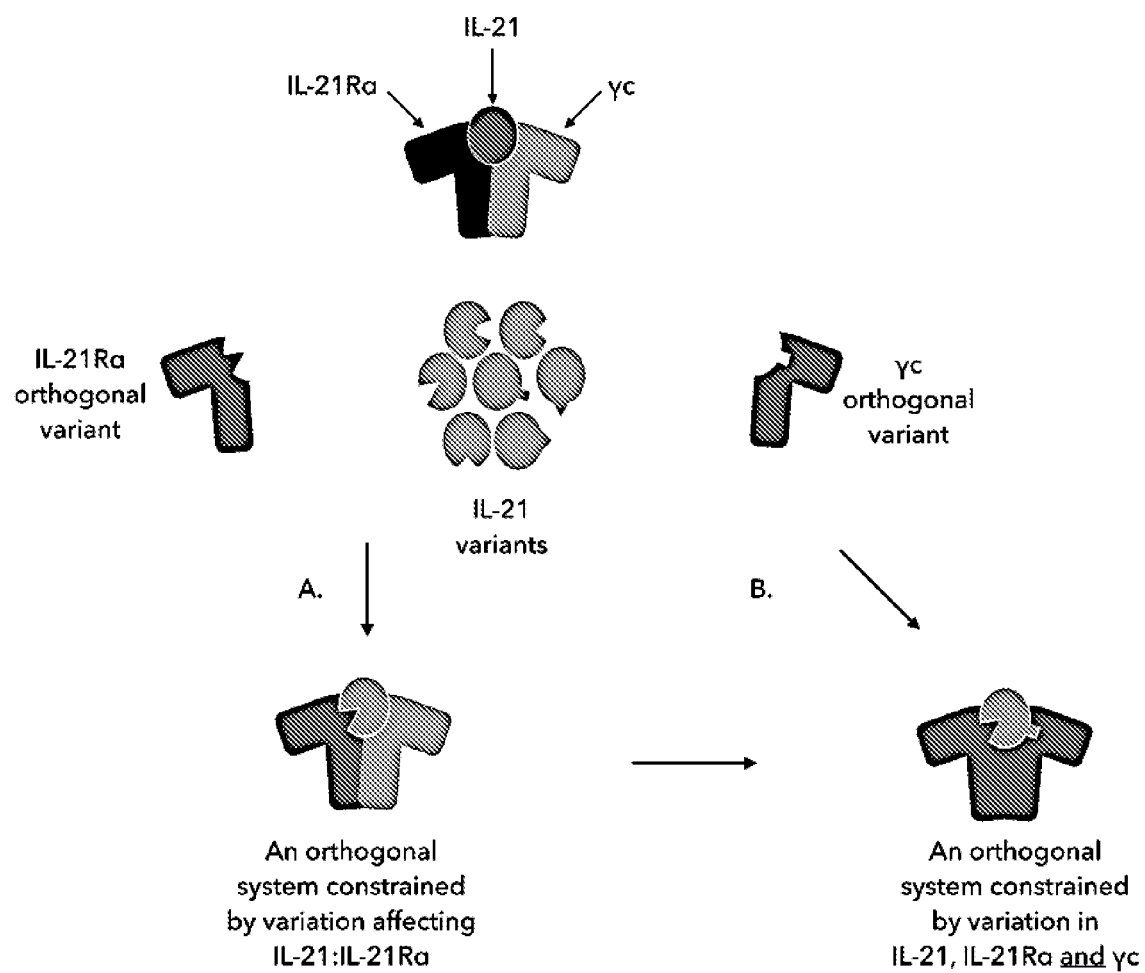
FIG. 2 provides a schematic representation of pathways for generating an orthogonal IL-21 system.

The present invention includes an orthogonal cytokine system based on IL-21, which is a member of the γc family of cytokines. IL-21 is structurally related to IL-2 and signals via a dimeric receptor comprised of IL-21Rα and γc. Whereas the IL-2 receptor promotes a STAT5-dominated signaling response, STAT3 dominates the IL-21 response. IL-21 promotes a form of T cell differentiation that correlates with good outcomes in adoptive cellular therapy ("ACT"), including ACT using CAR-T cells, and it shows enhanced anti-tumor properties compared to IL-2 in various tumor model systems. As a result, IL-21 may prove to be a better adjunct for ACT than IL-2. Accordingly, in one aspect, an IL-21 orthogonal system is provided that comprises: 1) an ortho-IL-21 with impaired binding to native IL-21Rα; and 2) an ortho-IL-21Rα capable of binding the ortho-IL-21 while exhibiting impaired binding to native IL-21 (FIG. 1; FIG. 2, path A).

Orthogonal Interleukin-21 Receptors

In one aspect, an orthogonal interleukin-21 receptor is provided. The orthogonal interleukin-21 receptor can include modification of either of the chains making up the overall protein. In some aspects, an ortho-IL-21Rα is provided. The ortho-IL-21Rα includes a modified amino acid sequence derived from wild-type human IL-21Rα (SEQ ID NO: 1—human IL-21Rα in mature form lacking the signal peptide). The ortho-IL-21Rα binds to an ortho-IL-21 but has impaired binding to native IL-21. Human IL-21Rα is represented by SEQ ID NO: 20.

In some aspects, the modified amino acid sequence comprises a substitution of one or more of the amino acid residues of SEQ ID NO: 1 that contact IL-21, residues in the immediate vicinity of such contact residues, or residues elsewhere in IL-21Rα that have an influence on the conformation of the IL-21 binding surface. Amino acids within the immediate vicinity are those within 1, 2, 3, 4, or 5 amino acids of the contact residues in the primary protein sequence, or amino acid residues that are similarly nearby in the tertiary protein structure. In some aspects, the ortho-IL-21Rα includes an amino acid substitution, numbered relative to SEQ ID NO: 2, at position: Q33, E38, M70, D73, A127, Y129, S190, and combinations thereof. In one aspect, the amino acid substitution comprises, consists essentially of, or consists of: M70G, M70I, D73E, Q33H, E38T, E38H, Y129F, S190F, A127M, and combinations thereof.

One strategy for creating an orthogonal version of IL-21 involves first mutating IL-21Rα such that it suffers reduced binding capability to IL-21. Twenty IL-21Rα amino acids make significant direct contacts with IL-21 within a binding surface of 990 Å$^2$. Mutating certain of these 20 residues impairs the capacity of the receptor to bind normally to IL-21. For example, the methionine residue at position 70 of IL-21Rα has been identified as a major contributor to the binding interaction. The large hydrophobic side chain of this residue fits into an IL-21 pocket comprised of mostly hydrophilic residues (Arginine-9, Glutamine-12, Arginine-76, Lysine-73, and Isoleucine-16), repositioning some of them for improved contact with IL-21Rα (notably, Arginine-9 and Arginine-76 of IL-21 contact Aspartic acid-72 and Aspartic acid-73 of IL-21Rα, respectively). Changing Methionine-70 to a different residue adjusts this repositioning such that some of these contacts are weakened or lost. Changing Aspartic acid-72 or -73 of IL-21Rα decreases the binding free energy of the interaction such that compensatory changes in IL-21 (e.g., at positions 9 and 76) are required to restore it.

Helix C of IL-21 exists in two interchangeable states (one disordered, the other α-helical) in the free structure of the cytokine. The α-helical form is stabilized in the complex of IL-21 with IL-21Rα, as is the first part of the CD loop. Helix C of IL-21 contains the above-mentioned Lysine-73 and Arginine-76, which are proximal to Methionine-70 of IL-21Rα. The CD loop of IL-21 includes Lysine-77, Proline-79, and Serine-80, which collectively form a pocket for Tyrosine-36 of IL-21Rα; Lysine-77 also makes an ionic contact with Glutamic acid-38 of IL-21Rα. Changing the CD loop amino acid sequence to the analogous sequence found in IL-4 results in a ten-fold enhancement of IL-21 potency measured using a cellular assay. This observation suggests that significant binding energy is expended in stabilizing helix C of IL-21. Moreover, it suggests that changes to Glutamic acid-38 and Tyrosine-36 of IL-21Rα should significantly impact IL-21 binding in a manner that might be reversible by compensatory changes to IL-21 in helix C or the CD loop.

Discrete avian sequence motifs can be used in the design of an orthogonal IL-21 system. Of 44 available avian sequences of IL-21, 39 have significantly (six residues) shortened CD loops compared to humans and mice. Together with the absence of Tyrosine-36 in the 74 available avian IL-21Rα sequences, this suggests helix C of avian IL-21 likely engages its receptor in a distinct fashion to that of human IL-21. This also provides an additional basis for modifications to the binding residues mentioned above for constructing an orthogonal IL-21 system.

Based on structural considerations, candidate amino acids may be identified that can be modified to change IL-21Rα such that its binding to native IL-21 is impaired. These changes must, however, be of a character that will not be incompatible with compensatory changes in IL-21 (i.e., changes in IL-21 that would restore binding to ortho-IL-21Rα). Changes to IL-21Rα resulting in large alterations to its conformation are not desirable because the number of compensatory changes required to restore binding may either present too great an engineering challenge or be incompatible with cytokine function (e.g., because γc binding is lost, or because the cytokine or cytokine receptor becomes unstable, difficult to express, immunogenic, or pharmacologically problematic).

At least two kinds of assays can be used to screen ortho-IL-21Rα for a loss of binding to IL-21. One is a direct binding assay, which can be carried out, for example, using purified proteins and a sensitive biophysical analytical procedure such as surface plasmon resonance ("SPR") or biolayer interferometry ("BLI"). Another assay is a functional assay involving an appropriate cell line. Ba/F3 cells have been used successfully for this purpose because they possess a number of useful traits: (i) they do not express endogenous IL-21Rα; (ii) they express mouse γc, which substitutes effectively for human γc in signaling with human IL-21Rα and human IL-21; (iii) they respond to IL-21R signaling by phosphorylating STAT3 and proliferating; and (iv) they permit use of a STAT3 reporter transgene (such as one expressing luciferase) as a facile and attractive means for monitoring IL-21 signaling. Jurkat or Molt-3 cells are alternative choices, both of which show minimal or absent expression of endogenous IL-21Rα but express γc and are IL-21R signaling-competent. HeLa cells transfected to express γc may also be used.

The strategy for isolating candidate ortho-IL-21Rα involves expressing the variants individually in Ba/F3 cells (or one of the alternatives just mentioned) by transfection. Flow cytometry is used to confirm the presence of the candidate ortho-IL-21Rα molecules on the cell surface and the presence of epitopes recognized by available antibodies. In one aspect, the candidate ortho-IL-21Rα includes an amino acid substitution at position: Q33, E38, M70, D73, A127, Y129, S190, and combinations thereof (where the numbers refer to the residue position in the mature IL-21Rα ectodomain (SEQ ID NO: 2), and letters refer to amino acid identity using the single letter code, the first letter being the wild-type residue and the second, if present, the substitute residue). In one aspect, the amino acid substitution comprises, consists essentially of, or consists of: In one aspect, the amino acid substitution comprises, consists essentially of, or consists of: M70G, M70I, D73E, Q33H, E38T, E38H, Y129F, S190F, A127M, and combinations thereof. In one aspect, the amino acid substitution comprises, consists essentially of, or consists of: RV13, RV22, RV6, RV31, RV31-E38T, RV31-E38H, RV31-S190F, RV31-A127M, RV31-S190F/A127M/E38T, RV31-S190F/A127M/E38H, RV31-S190F/E38T, RV31-S190F/E38H, RV31-A127M/E38T, RV31-A127M/E38H, or RV31-S190F/A127M. In one aspect, RV13 and RV22 may be substituted in the same manner as RV31, i.e., at positions S190, A127, and E38.

Ba/F3 cells expressing candidate ortho-IL-21Rα may be incubated with native human IL-21 before analysis for a signaling response. In some experiments, a time course may be used to improve assay sensitivity and resolution. Other experiments involve comparisons of dose-response curves. IL-21 responsiveness is detected by monitoring proliferation of the Ba/F3 cells, tyrosine phosphorylation of STAT3 by flow cytometry or immunoblotting, or expression of a reporter (such as luciferase or secreted alkaline phosphatase) from a STAT3-dependent reporter transgene present in the cells. Whereas native IL-21Rα allows a robust response to IL-21 using any of these analytical techniques, the desired ortho-form of the receptor will have a reduced or no response. Ortho-IL-21Rα molecules demonstrating this nonresponsive property are candidates for orthogonally restricted IL-21 cytokine-receptor systems.

Orthogonal Interleukin-21 Cytokines

Another aspect provides an ortho-IL-21 having a modified amino acid sequence derived from wild-type human IL-21 (SEQ ID NO: 7—human IL-21 in mature form lacking the signal peptide) that binds to an ortho-IL-21Rα but has impaired binding to native IL-21Rα. Human IL-21 is represented by SEQ ID NO: 21.

In some aspects, the ortho-IL-21 binds to an ortho-IL-21Rα but has impaired binding to native IL-21Rα. In further aspects, the modified amino acid sequence comprises a substitution of one or more amino acid residues of SEQ ID NO: 7 that contact IL-21Rα, residues in the immediate vicinity of such contact residues, or residues elsewhere in IL-21R that have an influence on the conformation of the IL-21α binding surface.

Methods are also available to identify orthogonal forms of IL-21. Ten residues of IL-21 participate in polar interactions with IL-21Rα: Arginine-5, Arginine-9, Arginine-11, Glutamine-12, Aspartic acid-15, Serine-70, Lysine-73, Arginine-76, Lysine-77, and Serine-80. Among these, Arginine-5, Arginine-9, Arginine-11, Glutamine-12, Lysine-73, Arginine-76, and Lysine-77 also form significant van der Waals contacts with IL-21Rα. Isoleucine-8, Isoleucine-16, Glutamine-19, Tyrosine-23, Isoleucine-66, Valine-69, and Proline-79 make additional van der Waals contacts. Substitutions can be made to any of these residues to overcome the changes present in candidate ortho-IL-21Rα molecules and restore binding.

The crystal structure of IL-21 bound by IL-21Rα can be used to identify IL-21 residues proximal to changes engineered into IL-21Rα. If, for example, changing Methionine-70 of IL-21Rα impairs IL-21 binding, then it is possible that compensatory changes to any of the following Methionine-70 contact residues in IL-21 may restore binding: Arginine-9, Glutamine-12, Isoleucine-16, Lysine-73, and Arginine-76. However, in addition to Methionine-70, these five IL-21 residues contact the following IL-21Rα residues: Tyrosine-10, Leucine-39, Glutamic acid-38, Phenylalanine-67, Alanine-71, Aspartic acid-72, Aspartic acid-73, Tyrosine-129, Methionine-130, and Tyrosine-191. In turn, the ten IL-21Rα residues just mentioned mediate additional contacts with IL-21 residues Arginine-5, Isoleucine-8, Glutamine-19, Serine-70, and Lysine-77. Therefore, just considering direct contacts present in the native IL-21:IL-21Rα crystal structure, a single substitution at position Methionine-70 in IL-21Rα could impact interactions mediated by ten IL-21 residues (Arginine-5, Isoleucine-8, Arginine-9, Glutamine-12, Isoleucine-16, Glutamine-19, Serine-70, Lysine-73, Arginine-76, and Lysine-77). This infers that compensation for the substitution (i.e., restoring IL-21 binding) may be accomplished by changes to one or more of these ten residues. It is also possible that changes to residues that do not make direct contacts with IL-21Rα can result in conformational adjustments that work at a distance to allow for binding to be restored to the Methionine-70-substituted variant of IL-21Rα.

Phage display or yeast display technology can permit the screening of large mutation spaces. This is typically accomplished by creating highly diverse libraries of variants wherein small numbers of residues in a protein are changed in a random (or semi-random) combinatorial fashion. The library is then screened for the desired properties. In one aspect, screening can include identifying members of a library of IL-21 variants that are capable of binding to a candidate ortho-IL-21Rα. If, as in the example just described, a substitution at Methionine-70 impairs binding of IL-21Rα to native IL-21, then an IL-21 library can be constructed that has randomized combinatorial mutations in the ten potentially impacted contact residues (Arginine-5, Isoleucine-8, Arginine-9, Glutamine-12, Isoleucine-16, Glutamine-19, Serine-70, Lysine-73, Arginine-76, and Lysine-77). The theoretical complexity of such a library could exceed $10^{13}$. It is typically challenging and impractical to generate libraries comprised of more than $10^8$-$10^9$ variants. Screening of such a library could involve a selection process in which phage or yeast displaying variant forms of IL-21 attached to their surfaces are separated based on their capacity to adhere to a matrix coated with a candidate ortho-IL-21Rα (and not to a matrix coated with wild-type IL-21Rα). Repeated cycles of such selection are performed to enrich for the desired properties in IL-21. Analytical screening procedures (including SPR or BLI) are used to characterize the products of the selection in detail and identify those with optimal properties.

In one aspect, the ortho-IL-21 comprises a modified amino acid sequence comprising a substitution of one or more amino acid residues of SEQ ID NO: 7 that contact IL-21Rα, residues in the immediate vicinity of such contact residues, or residues elsewhere in IL-21 that have an influence on the conformation of the IL-21Rα binding surface.

In one aspect, the ortho-IL-21 comprises an amino acid substitution, numbered relative to SEQ ID NO: 7, at position: H6, R9, M10, R11, I16, Q19, I66, K73, R76, P78, S80, G84, or P104, and combinations thereof. In one aspect, the amino acid substitution comprises, consists essentially of, or consists of: H6L, R9K, M10L, R11S, R11T, I16V, Q19F, I66S, K73V, K73L, K73M, K73I, R76K, R76H, P78L, S80K, S80L, G84E, P104I, or P104A, and combinations thereof. In one aspect, the ortho-IL-21 comprises amino acid substitutions, numbered relative to SEQ ID NO: 7: H6L/M10L/P78L. In another aspect, the ortho-IL-21 further comprises amino acid substitution R9K. In another aspect, the ortho-IL-21 further comprises amino acid substitution G84E. In another aspect, the ortho-IL-21 further comprises one of amino acid substitution P104V or P104A. In another aspect, the ortho-IL-21 further comprises one of amino acid substitution K73V or K73I. In one aspect, such an ortho-IL-21 may include CV374, CV388, CV414, or CV415.

In one aspect, the ortho-IL-21 comprises amino acid substitutions, numbered relative to SEQ ID NO: 7: H6L/M10L/P78L. In another aspect, the engineered human IL-21 polypeptide further comprises one of amino acid substitution S80P, S80K, or S80V. In another aspect, the engineered human IL-21 polypeptide further comprises amino acid substitution G84E. In another aspect, the engineered human IL-21 polypeptide further comprises one of amino acid substitution P104I or P104A. In another aspect, the engineered human IL-21 polypeptide further comprises one of amino acid substitution K73V, K73L, or K73M. In another aspect, the engineered human IL-21 polypeptide further comprises one of amino acid substitution R76H or R76K. In another aspect, the engineered human IL-21 polypeptide further comprises one of amino acid substitution R11S or R11T. In another aspect, the engineered human IL-21 polypeptide further comprises amino acid substitution I16V. In another aspect, the engineered human IL-21 polypeptide further comprises amino acid substitution Q19F. In another aspect, the engineered human IL-21 polypeptide further comprises amino acid substitution I66S. In one aspect, such an engineered human IL-21 polypeptide may include CV339, CV425, CV431, CV458, CV588, CV617, or CV631.

Additional Methods for Identifying Orthogonal IL-21 Receptor-Cytokine Pairs

An alternative approach to the identification of ortho-IL-21 molecules involves iterative cycles of mutagenesis, again focused on small numbers of residues selected from those that make direct intermolecular contacts in the IL-21:IL-21Rα structure. This approach may also include residues that are near to contact points and/or residues in potentially relevant structural features. A broad version of this approach can involve any of the residues that are proximal to the entire area of contact with IL-21Rα and additional semi-randomly selected residues in proximal structural features. A more focused version involves residues—such as the ten potentially relevant for the Methionine-70 substitution—that might be directly impacted by the specific substitution(s) present in the candidate ortho-IL-21Rα. An alternative broad approach is one in which substitutions are made with minimal, if any, consideration of the structure of IL-21, but instead with a partial emphasis on substitutions that occur in IL-21 orthologues from other species. This approach involves single substitutions in individual residues throughout the IL-21 primary sequence.

The iterative process begins with a large number (e.g., 10-100) of candidate ortho-IL-21 forms. In some versions of the approach, double or triple mutants are included in the initial collection, but in other versions, only single point mutations of IL-21 are evaluated. These candidate ortho-IL- 21 molecules are tested for activity using the cellular assay described above (employing, for example, Ba/F3 cells carrying a STAT5-dependent luciferase reporter transgene). A minimum of two kinds of cells are used in the assay: cells expressing a candidate ortho-IL-21Rα and, as a counter-screen, cells expressing wild-type IL-21Rα.

The likelihood of the alternative approach succeeding corresponds to the number of candidate ortho-IL-21Rα molecules examined. Expanding this number reduces the likelihood of inadvertently selecting a candidate ortho-IL-21Rα that does not readily allow for IL-21 binding to be restored (even partially) with small numbers (e.g., less than three) of substitutions. Expanding this number also increases the likelihood of being able to isolate parallel mutually orthogonal systems that do not demonstrate crosstalk with each other or with wild-type IL-21 or IL-21Rα.

The data from the initial screening round may be deconvoluted and analyzed focusing on identifying substitutions in IL-21 that in isolation promote improved binding to candidate ortho-IL-21Rα molecules and diminished binding to native IL-21Rα. A second round of screening may be performed in which positively scoring substitutions from the first round are combined in new candidate ortho-IL-21 molecules. These candidate ortho-IL-21 molecules (and, if considered desirable, additional variations in which conservative or nonconservative substitutions are made at the positively scoring positions) are tested again for improved binding to candidate ortho-IL-21Rα molecules and impaired binding to native IL-21Rα.

Additional rounds of screening may be performed involving further combinations of substitutions until at least one candidate ortho-IL-21 has been isolated with the desired properties (absence of activity with native IL-21Rα and near-normal activity with at least one candidate ortho-IL-21Rα).

The alternative screening approach may, in some circumstances, be facilitated using candidate ortho-IL-21Rα molecules that retain reduced—but not entirely absent—binding to wild-type IL-21. Such reduced-binding candidate ortho-IL-21Rα molecules may prove more permissive than non-binding candidate ortho-IL-21Rα molecules (i.e., candidate ortho-IL-21Rα molecules lacking any binding to wild-type IL-21) to a restoration of some IL-21 binding activity by small numbers (e.g., less than three) of discrete substitutions in IL-21. Once candidate ortho-IL-21 molecules have been isolated by the screening procedure outlined above, additional screening steps may be performed involving new candidate ortho-IL-21Rα molecules in which additional substitutions are compounded with the ones already present. In some aspects, these additional mutations may entirely eliminate binding to wild-type IL-21 while retaining the capacity to bind the ortho-IL-21. Multiple rounds of this receptor mutagenesis may be performed along with subsequent refining cytokine mutagenesis rounds.

The binding properties of the products of the screening approach may be analyzed using purified proteins and BLI or SPR. The products that most closely resemble wild-type IL-21 and IL-21Rα in their binding kinetics may be chosen as candidate orthogonal IL-21 systems.

In one aspect, candidate ortho-IL-21 molecules may be engineered according to the process described in one or more of U.S. Pat. Nos. 8,005,620, 8,635,029, and 8,412,461, as well as Govindarajan S, Mannervik B, Silverman J A, et al. Mapping of amino acid substitutions conferring herbicide resistance in wheat glutathione transferase. *ACS Synth Biol.* 2015; 4(3):221-227. doi:10.1021/sb500242x; Musdal Y, Govindarajan S, Mannervik B. Exploring sequence—function space of a poplar glutathione transferase using designed information-rich gene variants. *Protein Eng Des Set.* 2017; 30(8):543-549. doi:10.1093/protein/gzx045; and Liao J, Warmuth M K, Govindarajan S, et al. Engineering proteinase K using machine learning and synthetic genes. *BMC Biotechnol.* 2007; 7:16. Published 2007 Mar. 26. doi: 10.1186/1472-6750-7-16, each of which is incorporated by reference herein its entirety.

In one aspect, candidate ortho-IL-21 molecules are expressed as fusion proteins between a modified amino acid sequence derived from SEQ ID NO: 7 as described above and a second amino acid sequence that facilitates purification, increases stability and half-life of the ortho-IL-21 molecules in vivo, or improves drug properties that are critical for successful dosing of ortho-IL-21 molecules in patients. Suitable second amino acid sequences are known in the art, and include, but are not limited to, serum albumin, Fc fragments of IgG, single-chain Fc antibody fragments, ABD035, and the like. Fc fragments can be modified, for example, with electrostatic steering mutations, to prevent, or at least significantly limit, the formation of homodimers.

Orthogonal IL-21 Receptor-Cytokine Systems

Another aspect provides a system for activating IL-21 signaling in a cell. The system includes a candidate ortho-IL-21Rα that has impaired binding to native IL-21, the candidate ortho-IL-21Rα comprising a modified amino acid sequence derived from SEQ ID NO: 1 comprising a substitution of one or more of the amino acid residues of SEQ ID NO: 1 that contact IL-21, residues in the immediate vicinity of such contact residues, or residues elsewhere in IL-21Rα that have an influence on the conformation of the IL-21 binding surface; and an ortho-IL-21 that has impaired binding to native IL-21Rα, the ortho-IL-21 comprising a modified amino acid sequence derived from SEQ ID NO: 7 comprising a substitution of one or more amino acid residues of SEQ ID NO: 7 that contact IL-21Rα, residues in the immediate vicinity of such contact residues, or residues elsewhere in IL-21 that have an influence on the conformation of the IL-21Rα binding surface wherein the ortho-IL-21Rα binds to the ortho-IL-21.

In some aspects, the cell is a T cell. In further aspects, the cell is a CAR-T cell. The orthogonal cytokine and orthogonal receptor can be any of the candidate ortho-IL-21 and candidate ortho-IL-21Rα molecules described herein. For example, in one aspect, the ortho-IL-21Rα includes an amino acid substitution, numbered relative to SEQ ID NO: 2, comprising, consisting essentially of, or consisting of: RV13, RV22, RV6, RV31, RV31-E38T, RV31-E38H, RV31-S190F, RV31-A127M, RV31-S190F/A127M/E38T, RV31-S190F/A127M/E38H, RV31-S190F/E38T, RV31-S190F/E38H, RV31-A127M/E38T, RV31-A127M/E38H, or RV31-S190F/A127M (in one aspect, RV13 and RV22 may be substituted in the same manner as RV31, i.e., at positions S190, A127, and E38); and the ortho-IL-21 includes an amino acid substitution, numbered relative to SEQ ID NO: 7, comprising, consisting essentially of, or consisting of one of: CV374, CV388, CV414, CV415, CV339, CV425, CV431, CV458, CV588, CV617, or CV631.

Expression Vectors for Orthogonal Cytokines and Receptors

Another aspect provides expression vectors comprising a nucleic acid encoding any of the candidate orthogonal IL-21 proteins (e.g., receptors or cytokines) described herein. Orthogonal proteins, such as ortho-IL-21 or ortho-IL-21Rα, may be produced by recombinant methods. Ortho-IL-21Rα may be introduced on an expression vector into a cell to be engineered. DNA encoding an orthogonal protein may be obtained from various sources as designed during the engineering process.

Amino acid sequence variants may be prepared by introducing appropriate nucleotide changes into the nucleic acid coding sequence encoding the protein. The nucleic acid codons that encode amino acids are known to those skilled in the art. The specific codons selected may be chosen to optimize expression in the host cells being used. The amino acid variants may represent insertions, substitutions, and specified deletions of residues as described herein. Any combination of insertions, substitutions, and specified deletions may be made to arrive at the final construct, provided that the final construct possesses the desired biological activity as defined herein. In some aspects, the nucleic acid encodes an ortho-IL-21Rα as described herein.

In one aspect, the nucleic acid coding sequences for encoding certain of the candidate ortho-IL-21Rα and ortho-IL-21 molecules are set forth below:

| ortho-IL-21Rα or ortho-IL-21 molecules | Gene SEQ ID NO: |
| --- | --- |
| RV6 | 22 |
| RV13 | 23 |
| RV22 | 24 |
| RV31 | 25 |
| RV31-E38T | 92 |
| RV31-E38H | 93 |
| RV31-S190F | 94 |
| RV31-A127M | 35 |
| RV31-S190F/A127M/E38T | 102 |
| RV31-S190F/A127M/E38H | 103 |
| RV31-S190F/E38T | 104 |
| RV31-S190F/E38H | 105 |
| RV31-A127M/E38T | 106 |
| RV31-A127M/E38H | 107 |
| RV31-S190F/A127M | 108 |
| CV374 | 26 |
| CV388 | 27 |
| CV414 | 28 |
| CV415 | 29 |
| CV339 | 30 |
| CV425 | 31 |
| CV431 | 32 |
| CV458 | 33 |
| CV588 | 89 |
| CV617 | 90 |
| CV631 | 91 |

Nucleic acids are "operably linked" when placed into a functional relationship with another nucleic acid sequence. For example, DNA for a signal sequence is operably linked to DNA for a polypeptide if the DNA for a signal sequence is expressed as a preprotein that participates in the secretion of the polypeptide; a promoter or enhancer is operably linked to a coding sequence if the promoter or enhancer affects the transcription of the sequence; or a ribosome binding site is operably linked to a coding sequence if the ribosome binding site is positioned so as to facilitate translation. Generally, "operably linked" means that the DNA sequences being linked are contiguous, and, in the case of a secretory leader, contiguous and in reading phase. However, some sequences, such as enhancers, do not have to be contiguous to be effective.

The nucleic acid encoding the ortho-IL-21 or ortho-IL-21Rα may be inserted into a replicable vector for expression. Many such vectors are available. The vector components generally include, but are not limited to, one or more of the following: an origin of replication, one or more marker genes, an enhancer element, a promoter, and a transcription termination sequence. Vectors may include viral vectors, plasmid vectors, integrating vectors, transposons, and the like. For example, a suitable transposon/transposase-based polynucleotide vector system is described in U.S. Pat. No. 10,041,077, which is incorporated by reference herein in its entirety.

The ortho-IL-21 or ortho-IL-21Rα may be recombinantly produced without modification or as a fusion polypeptide with a heterologous polypeptide, e.g., a signal sequence or other polypeptide having a specific cleavage site at the N-terminus of the mature protein or polypeptide. In general, the signal sequence may be a component of the vector, or it may be a part of the coding sequence that is inserted into the vector. The heterologous signal sequence selected may be one that is recognized and processed (i.e., cleaved by a signal peptidase) by the host cell. In mammalian cell expression, the native signal sequence may be used, or other mammalian signal sequences may be suitable, such as signal sequences from secreted polypeptides of the same or related species, as well as viral secretory leaders, for example, the herpes simplex gD signal.

Expression vectors typically contain a selection gene, also termed a selectable marker. The selection gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors may contain a promoter that may be recognized by the host organism and may be operably linked to an orthogonal protein coding sequence. Promoters may be untranslated sequences located upstream (5') to the start codon of a structural gene (generally within about 100 to 1000 bp) that control the transcription and translation of the particular nucleic acid sequence to which they are operably linked. Such promoters typically fall into two classes: inducible and constitutive. Inducible promoters are promoters that initiate increased levels of transcription from DNA under their control in response to some change in culture conditions, e.g., the presence or absence of a nutrient or a change in temperature.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus (such as murine stem cell virus), hepatitis-B virus, and Simian Virus 40 ("SV40"), from heterologous mammalian promoters, e.g., the actin promoter, phosphoglycerate kinase ("PGK"), or an immunoglobulin promoter, from heat-shock promoters, provided such promoters are compatible with the host cell systems. The early and late promoters of SV40 are conveniently obtained as an SV40 restriction fragment that also contains the SV40 viral origin of replication.

The expression vector may also include an enhancer sequence. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are known from mammalian genes (e.g., globin, elastase, albumin, α-fetoprotein, and insulin). Typically, however, one will use an enhancer from a eukaryotic cell virus. Examples may include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter.

Expression vectors used in eukaryotic host cells will also contain sequences necessary for the termination of transcription and for stabilizing the mRNA. Such sequences are commonly available from the 5' and 3' untranslated regions of eukaryotic or viral DNAs or cDNAs.

Expression vectors might also be comprised of inducible regulatory elements for the purpose of controlling expression of a transgene (encoding, for example, ortho-IL-21 or ortho-IL-21Rα) with small molecules or other stimulatory agents. Examples of regulatory elements include, but are not limited to, promoters containing tetracycline operators that render them sensitive to regulation by tetracycline or derivatives thereof (such as doxycycline). Promoters may also be inducibly regulated by CRISPRa (clustered regularly interspaced short palindromic repeats-activation) using fusions of transcriptional effectors and catalytically dead Cas9. Such promoters may in turn be downstream of other control systems such as those involving dimerizers (of an antibody-based and/or chemical nature) or components based on the Notch receptor.

Engineered Cells

In one aspect, cells are provided that have been engineered to express an ortho-IL-21Rα. The cells may be genetically engineered to include any suitable expression vector described herein. In some aspects, the expression vector comprises a coding sequence that encodes the orthogonal receptor, the coding sequence being operably linked to a promoter active in the desired cell. Various vectors may be used for this purpose, e.g., transposons, viral vectors, plasmid vectors, and minicircle vectors, which can be integrated into the target cell genome or can be episomally maintained. In one aspect, the expression vector is a synthetic transposon that can be integrated into the genome by means of a transposase enzyme. Examples of transposon/transposase systems include Sleeping Beauty, PiggyBac, LeapIn® from ATUM Bio, and derivatives thereof.

The engineered cell may be a host cell for preparing recombinant protein in vitro. Suitable host cells for recombinant expression of orthogonal proteins include prokaryotes, yeast, and higher eukaryote cells, such as various mammalian host cell lines.

In some aspects, the engineered cell is further modified beyond the expression of an ortho-IL-21Rα. Modifications suitable for use in engineered cells are known in the art and include expression of a CAR, a T cell Receptor ("TCR"), or other receptor or receptor derivatives that recognize specific antigens on antigen presenting cells.

In some aspects, the engineered cell is a cell intended for therapeutic use. Examples of therapeutic engineered cells may include stem cells, e.g., a hematopoietic stem cell, a natural killer ("NK") cell, or a T cell. In some aspects, the engineered cell is a T cell. The term "T cells" refers to mammalian immune effector cells that may be characterized by expression of a CD3 and/or a T cell antigen receptor, which cells may be engineered to express an ortho-IL-21Rα. In some aspects, the T cells are selected from naïve, activated, or post-activation CD8+ T cells; cytotoxic CD8+ T cells; naïve, activated, or post-activation CD4+ T cells; helper T cells, e.g., TH1, TH2, TH9, TH11, TH22, and TFH; regulatory T cells, e.g., TR1, natural TReg, and inducible TReg; and memory T cells, e.g., central memory T cells, effector memory T cells, NKT cells, and γδ T cells.

Ortho-IL-21 may be used as an adjunct to ACT. T cells may be engineered to express the ortho-IL-21Rα by gene (cDNA, minigene, or other nucleic acid construct) transfection, transduction, or transposition. Patients receiving the ACT may be treated (and/or pretreated) with the ortho-IL-21 and dosed repeatedly as needed to augment and sustain a desirable T cell presence and responses.

Therapeutic cells may also be engineered to express ortho-IL-21. This could be accomplished using any of the methods appropriate for ectopic expression of ortho-IL-21Rα. The ortho-IL-21 could be expressed in the same or different cells as those that express ortho-IL-21Rα, allowing for autocrine or paracrine action, respectively. An example of a paracrine arrangement could be CD4+ T cells expressing the ortho-IL-21 and CD8+ T cells expressing the matched ortho-IL-21Rα.

In some aspects, ortho-IL-21 may be expressed in a membrane-tethered form. This has previously been accomplished with natural IL-21 by fusing the cytokine to the amino-terminus of an IgG4 $CH_2$—$CH_3$ moiety that was itself fused to a CD4 transmembrane domain. Related strategies have been employed to tether other cytokines to the membranes of cells. Such membrane tethering limits the diffusion of the cytokine and restricts its action to the immediate vicinity of the cells expressing the membrane-bound cytokine. In vivo, this approach could be exploited to ensure ortho-IL-21Rα-expressing cells only encounter the ortho-IL-21 when they are proximal to a specific type of cell and/or location in the body. In vitro, the approach may facilitate certain kinds of selective differentiation protocols (e.g., the differentiation of NK cells from stem cells in the presence of K562 [or other] feeder cells expressing membrane-bound IL-21 and CD137L).

Engineered cells may be provided in pharmaceutical compositions suitable for therapeutic use, e.g., for human treatment. Therapeutic formulations comprising such cells can be frozen or prepared for administration with physiologically acceptable carriers, excipients, or stabilizers (Remington's Pharmaceutical Sciences 16th edition, Osol, A. Ed. (1980)) in the form of aqueous solutions. The cells may be formulated, dosed, and administered in a fashion consistent with good medical practice.

Methods of Treatment

A cell such as a T cell engineered to express one of the ortho-IL-21Rα molecules described herein may be used to treat a broad range of conditions. Engineered properties in this therapy may allow for beneficial T cell differentiation, resistance to exhaustion, capacity for long-term persistence, anamnestic responses, and in-built safety features allowing for responses to be halted when they become pathogenic.

Methods are provided for enhancing cellular responses by engineering cells from a recipient or donor by introduction of an ortho-IL-21Rα and stimulating the ortho-IL-21Rα by contacting the engineered cell with ortho-IL-21. The subject methods may include a step of obtaining the targeted cells, e.g., T cells, hematopoietic stem cells, etc., which may be isolated from a biological sample or may be derived in vitro from a source of progenitor cells. The cells may be transduced or transfected with an expression vector comprising a sequence encoding the ortho-IL-21Rα, which step may be performed in any suitable culture medium.

In some aspects, the engineered T cells may be contacted with the ortho-IL-21 in vivo, i.e., where the engineered T cells are transferred to a recipient, and an effective dose of the ortho-IL-21 is injected into the recipient and allowed to contact the engineered T cells in their native environment, e.g., in lymph nodes, etc. In other aspects, the contacting is performed in vitro. In such in vitro aspects, the contacting may be accomplished using soluble ortho-IL-21 comprised, or not, of a fusion to another protein moiety such as an immunoglobulin Fc domain. In further such in vitro aspects, the contacting could be accomplished by encounter with other cells expressing secreted or membrane-tethered ortho-IL-21.

Another aspect provides a method for treating a subject in need thereof, including introducing an engineered cell expressing an ortho-IL-21Rα to the subject and activating the cell by contacting it with an effective amount of an ortho-IL-21. In some aspects, the cell is a T cell, while in further aspects the cell is a CAR-T cell. In another aspect, the cell is a T cell expressing a native or modified TCR. In another aspect, the cell is an NK cell. In another aspect, the cell is a macrophage or other myeloid cell or a leukocyte.

In some aspects, the ortho-IL-21 is delivered as a fusion protein with a heterologous polypeptide. Suitable heterologous polypeptides are known in the art and include serum albumin, Fc fragments of IgG, single-chain Fc antibody fragments, ABD035, and the like. Fc fragments may be modified, for example, with electrostatic steering or other mutations, to prevent, or at least significantly limit, the formation of homodimers.

Another aspect provides a method for treating a subject in need thereof, including introducing an engineered cell expressing an ortho-IL-21Rα to the subject and introducing a second engineered cell expressing an ortho-IL-21. In some aspects, the cell is a T cell, while in further aspects the cell is a CAR-T cell.

A "subject," can be any mammal and may also be referred to as a "patient." Examples of mammalian subjects include research animals (e.g., a mouse or rat), domesticated farm animals (e.g., cow, horse, pig), pets (e.g., dog, cat), and humans. In some aspects, the subject is a human.

In some aspects, the subject being treated has been diagnosed as having cancer. "Cancer" and "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize), as well as any of a number of characteristic structural and molecular features. A "cancer cell" refers to a cell undergoing early, intermediate, or advanced stages of multi-step neoplastic progression. The features of early, intermediate, and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some aspects, the engineered cells are used to treat cancer selected from the group consisting of colon cancer, brain cancer, breast cancer, fibrosarcoma, and squamous carcinoma. In some aspects, the cancer is selected from the group consisting of melanoma, breast cancer, colon cancer, lung cancer, and ovarian cancer. In some aspects, the cancer being treated is metastatic cancer.

In case of cancer treatment, the method of treatment may further include the step of ablating the cancer. Ablating the cancer may be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

In some aspects, the subject being treated has been diagnosed as having an infection. As used herein, the term "infection" refers to infection of one or more cells of a subject by an infectious agent. Infectious agents include, but are not limited to, bacteria, viruses, protozoans, and fungi. Intracellular pathogens are of particular interest. Infectious diseases are disorders caused by infectious agents. Some infectious agents cause no recognizable symptoms or disease under certain conditions but have the potential to cause symptoms or disease under changed conditions. The subject methods may be used in the treatment of chronic pathogen infections, including but not limited to viral infections, e.g., retrovirus, lentivirus, hepadnavirus, herpes viruses, pox viruses, and human papilloma viruses; intracellular bacterial infections, e.g., *Mycobacterium, Chlamydia, Ehrlichia, Rickettsia, Brucella, Legionella, Francisella, Listeria, Coxiella, Neisseria, Salmonella, Yersinia* sp, and *Helicobacter pylori*; and intracellular protozoan pathogens, e.g., *Plasmodium* sp, *Trypanosoma* sp, Giardia sp, *Toxoplasma* sp, and *Leishmania* sp.

In some aspects, the subject being treated has been diagnosed as having an autoimmune disease. Autoimmune diseases are characterized by T and B lymphocytes that aberrantly target self-proteins, -polypeptides, -peptides, or other self-molecules, causing injury and/or malfunction of an organ, tissue, or cell-type within the body. Autoimmune diseases include diseases such as rheumatoid arthritis, systemic lupus erythematosus, multiple sclerosis, autoimmune hepatitis, insulin dependent diabetes mellitus, and degenerative diseases such as osteoarthritis, Alzheimer's disease, and macular degeneration.

To effect treatment, one or more engineered cells of the subject may be contacted with ortho-IL-21. Where the engineered cells are contacted with the ortho-IL-21 in vitro, the ortho-IL-21 may be added to the engineered cells in a dose and for a period of time sufficient to activate signaling from the ortho-IL-21Rα, which may utilize the native cellular machinery, e.g., accessory proteins, co-receptors, and the like. Any suitable culture medium may be used. The engineered cells thus activated may be used for any desired purpose, including experimental purposes relating to determination of antigen specificity, cytokine profiling, and the like, and for delivery in vivo.

Where the contacting is performed in vivo, an effective dose of engineered cells expressing ortho-IL-21Rα are infused to the recipient, in combination with or prior to administration of the ortho-IL-21. Dosage and frequency may vary depending on the agent, mode of administration, and the like. The dosage may also be varied for localized administration, e.g., intranasal, inhalation, and the like, or for systemic administration, e.g., i.m., i.p., i.v., and the like. Generally, at least about $10^4$ engineered cells/kg are administered, at least about $10^5$ engineered cells/kg, at least about $10^6$ engineered cells/kg, at least about $10^7$ engineered cells/kg, or more.

EXAMPLES

Example 1: Binding Assay for Identification of Candidate Ortho-IL-21Rα Molecules with Impaired Binding to Native IL-21

A direct interaction assay (quantifying the capacity of IL-21Rα to bind native or mutant forms of IL-21) provides an alternative to a cell-based assay for the identification of variants of IL-21Rα with compromised IL-21 binding activity (i.e., candidate orthogonal variants). The feasibility of exploiting such an assay is enhanced by the fact that the native interaction (IL-21Rα:IL-21) is avid (KD~70 pM). Of many possible forms of a binding assay, one involving luciferase fusion proteins is appealing because of its simplicity and the potential for it to be adapted to a medium- or high-throughput format.

One version of an IL-21Rα:IL-21 binding assay involves attaching the receptor ectodomain to a surface, bathing the coated surface in a solution of an IL-21-luciferase fusion protein, followed by quantitation of bound IL-21 based on luminescence when the relevant luciferase substrate is added. Alternatively, IL-21 may be immobilized, and an IL-21Rα-luciferase fusion protein may be used in solution.

In either form of the binding assay, a desirable orientation of the immobilized receptor or cytokine can be accomplished through use of an affinity tag such as Twin-Strep-Tag II, which is a high affinity peptide ligand for the Streptactin protein. The IL-21Rα ectodomain bearing a carboxy-terminal Twin-Strep-Tag II peptide can be efficiently and selectively immobilized on the surfaces of wells of 96-well plates that have been pre-coated with Streptactin protein. In this manner, the immobilized IL-21Rα should be oriented with its cytokine-binding domain distal from the plate surface. Similarly, IL-21 may be immobilized in a related fashion if it, too, bears an amino- or carboxy-terminal Twin-Strep-Tag II peptide tag.

An assay was established using plate-immobilized human IL-21Rα ectodomain (via a carboxy-terminal Twin-Strep-Tag II) and a fusion protein (SEQ ID NO: 34) ("IL-21-TLuc16" in FIG. 3) in which the 16KD Turbo-luciferase polypeptide (ThermoFisher) was linked (via a Glycine-Serine-containing peptide) to the carboxy-terminus of human IL-21. Bound IL-21 was detected using the Turbo-Luc Luciferase One-Step Glow Assay Kit (ThermoFisher) and standard luminometry. This assay could also be established with luciferase fused at the amino-terminus of IL-21 or with an alternative form of luciferase (e.g., NanoLuc; ThermoFisher).

Twenty candidate ortho-IL-21Rα molecules were tested for their capacity to bind IL-21-TLuc16. The wild-type human IL-21Rα ectodomain (mature form lacking the signal peptide) (RV0 (SEQ ID NO: 6)) and the 20 candidate ortho-IL-21Rα molecule ectodomains (mature form lacking the signal peptide) (SEQ ID NOs shown in Table 1) were expressed in HEK 293 cells as secreted proteins.

TABLE 1

| RV | SEQ ID NO: |
|---|---|
| RV1 (H68Q, E38D, Q33H) | 36 |
| RV2 (D72E, Y129F, D73E) | 37 |
| RV3 (Y129F, H68Q, Y191F) | 38 |
| RV4 (Y36F, H68Q, D73E) | 39 |
| RV5 (Y129F, F67Y, M130L) | 40 |
| RV6 | 5 |
| RV7 (D72E, L94V, Y191F) | 41 |

TABLE 1-continued

| RV | SEQ ID NO: |
|---|---|
| RV8 (L94V, Q33H, M130L) | 42 |
| RV9 (Y36F, F67Y, E38D) | 43 |
| RV10 (D72E, E38D, M130L) | 44 |
| RV11 (Y36F, M70I, L94V) | 45 |
| RV12 (M70I, F67Y, Y191F) | 46 |
| RV13 | 3 |
| RV14 (Y36H) | 47 |
| RV15 (F69L M70L D73I) | 48 |
| RV16 (Y129H M130F) | 49 |
| RV17 (Y129F, M130S) | 50 |
| RV18 (D72K, D73K) | 51 |
| RV19 (E38K) | 52 |
| RV20 (F67L) | 53 |

Clarified supernatant fluids from the transiently transfected cells were tested for the presence of IL-21Rα with an Enzyme-Linked Immunosorbent Assay ("ELISA") comprised of Streptactin-coated plates, dilutions of the supernatant fluids, and detection using the combination of a mouse monoclonal antibody specific for the human IL-21Rα, a horseradish peroxidase-conjugated rat antibody specific for mouse IgG, and a chromogenic substrate for the peroxidase. This ELISA established the dilutions required to ensure saturation of the Streptactin-coated wells with each of the candidate ortho-IL-21Rα molecules. Candidate ortho-IL-21Rα saturated wells were incubated with a solution of IL-21-TLuc16 for 1 h (or longer in some experiments) at 4° C. (or room temperature in some experiments). The wells were washed before addition of the luciferase substrate (Coelenterazine) solution and luminometry.

Figure 3:
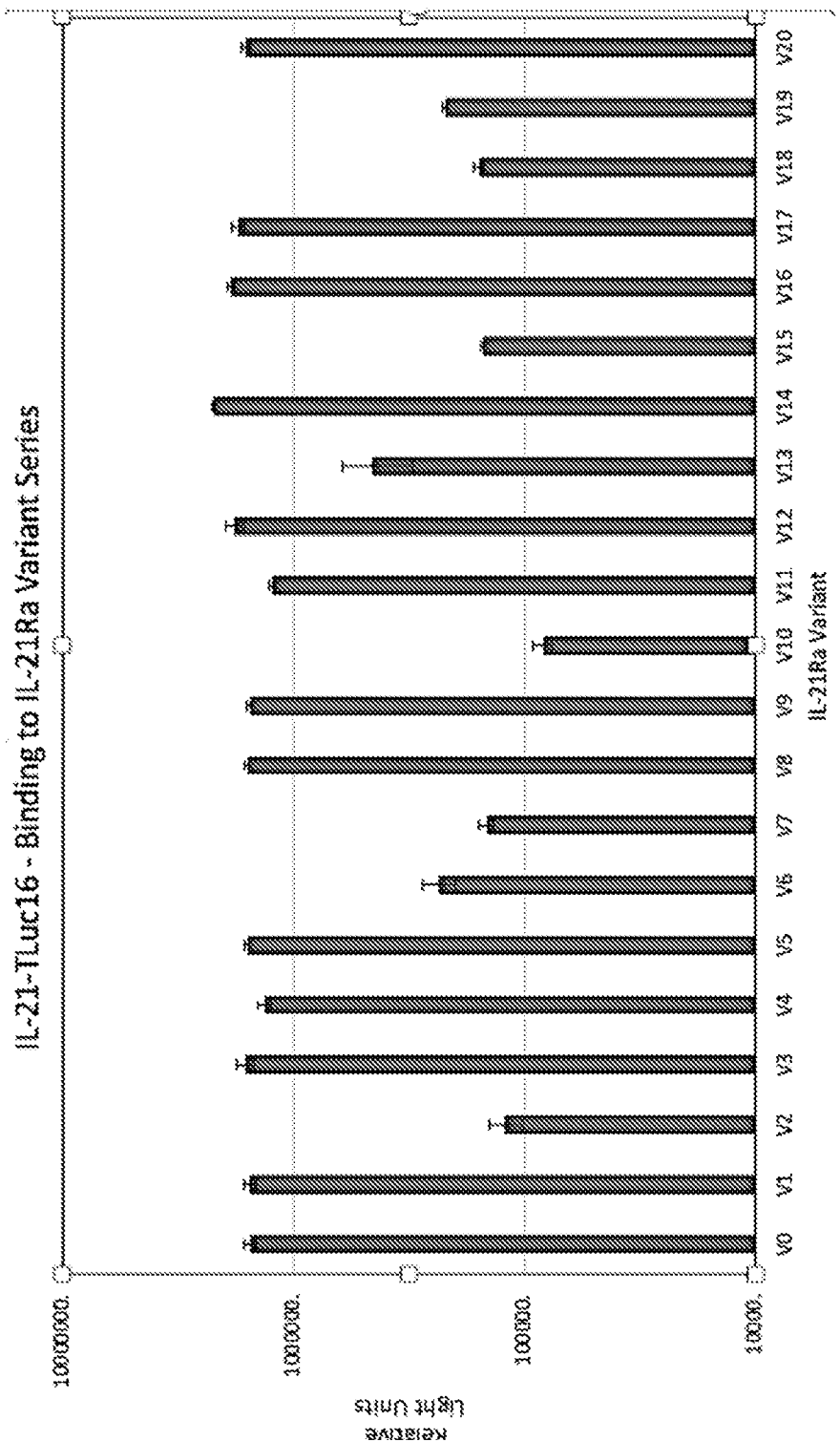
FIG. 3 shows the results of a representative assay in which a single (sub-saturating) concentration of IL-21-TLuc16 was tested for binding to a panel of 20 candidate ortho-IL-21Rα molecules (all of which had been bound to Streptactin-coated surfaces of wells at saturating concentrations), including RV6 and RV13. Eight of the 20 candidate ortho-IL-21Rα molecules showed diminished capacity to bind IL-21-TLuc16.

FIG. 3 shows the results of a representative assay in which a single (sub-saturating) concentration of IL-21-TLuc16 was tested for binding to the panel of 20 candidate ortho-IL-21Rα molecules (all of which had been bound to the Streptactin-coated surfaces of the wells at saturating concentrations). Eight of the candidate ortho-IL-21Rα molecules showed diminished capacity to bind IL-21-TLuc16. Repeat experiments (involving titrations of the IL-21-TLuc16) confirmed the results.

Additional candidate ortho-IL-21Rα molecules carrying alternative combinations of the amino acid substitutions present in the eight candidate ortho-IL-21Rα molecules were similarly tested for their capacity to bind IL-21-TLuc16. Certain of the additional candidate ortho-IL-21Rα molecule ectodomains (mature form lacking the signal peptide) (SEQ ID NOs shown in Table 2) were expressed in HEK 293 cells as secreted proteins.

TABLE 2

| RV | SEQ ID NO: |
|---|---|
| RV22 | 4 |
| RV23 (M70L) | 54 |
| RV24 (F69L) | 55 |
| RV25 (D73I) | 56 |
| RV28 (D73E) | 57 |
| RV29 (M70G,D73E) | 58 |
| RV30 (M70G, D73E, Q33H) | 59 |
| RV31 | 6 |
| RV32 (M70I, E38K) | 60 |

Figure 4A:
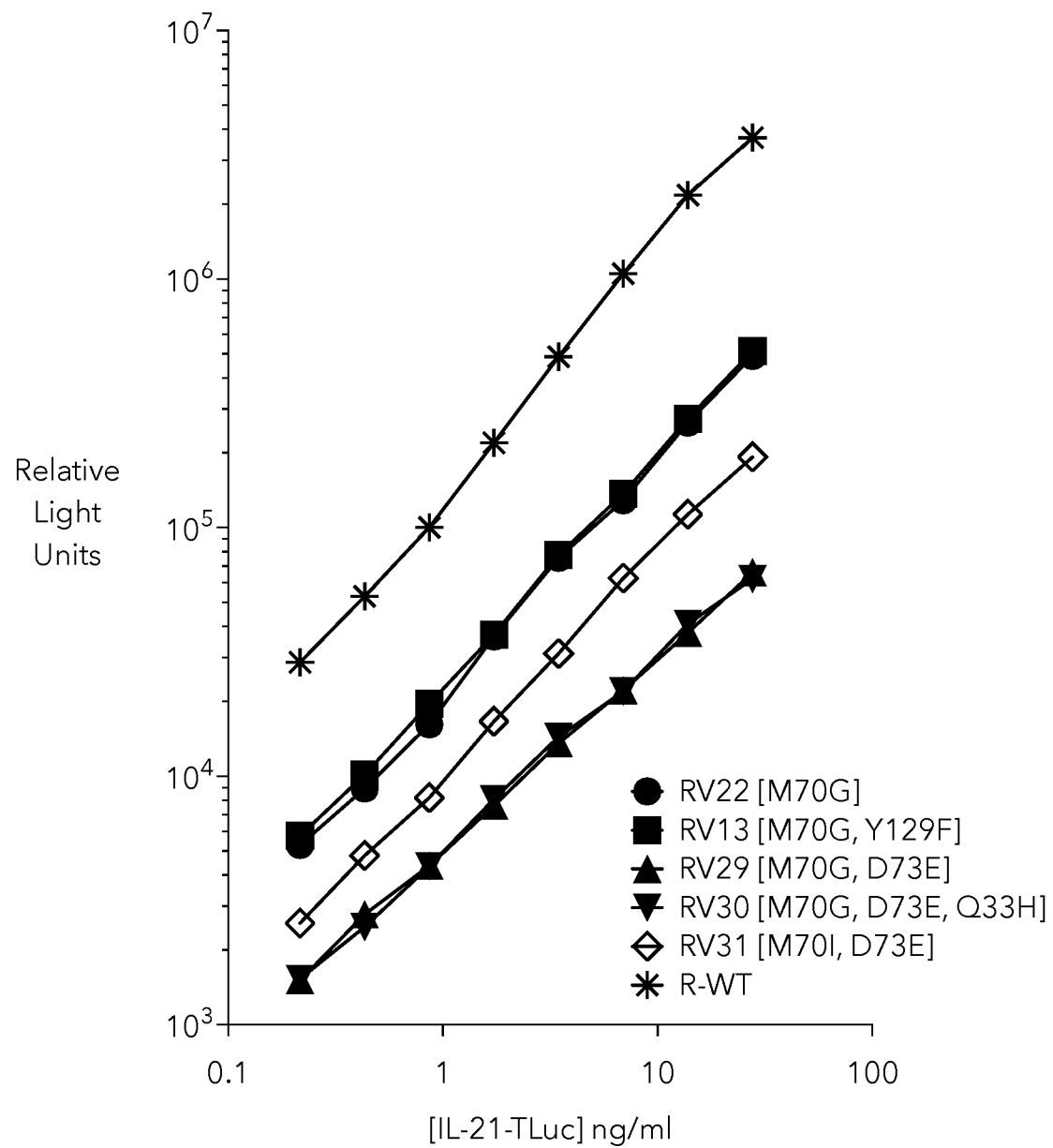
FIGS. 4A-C show the results of a representative assay in which a range of (sub-saturating) concentrations of IL-21-TLuc16 was tested for binding to a panel of candidate ortho-IL-21Rα molecules, including RV6, RV13, RV22, and RV31. The panel included a wild-type receptor as a control. The candidate ortho-IL-21Rα molecules were added to Streptactin-coated wells of 96-well plates at saturating concentrations.
Figure 4B:
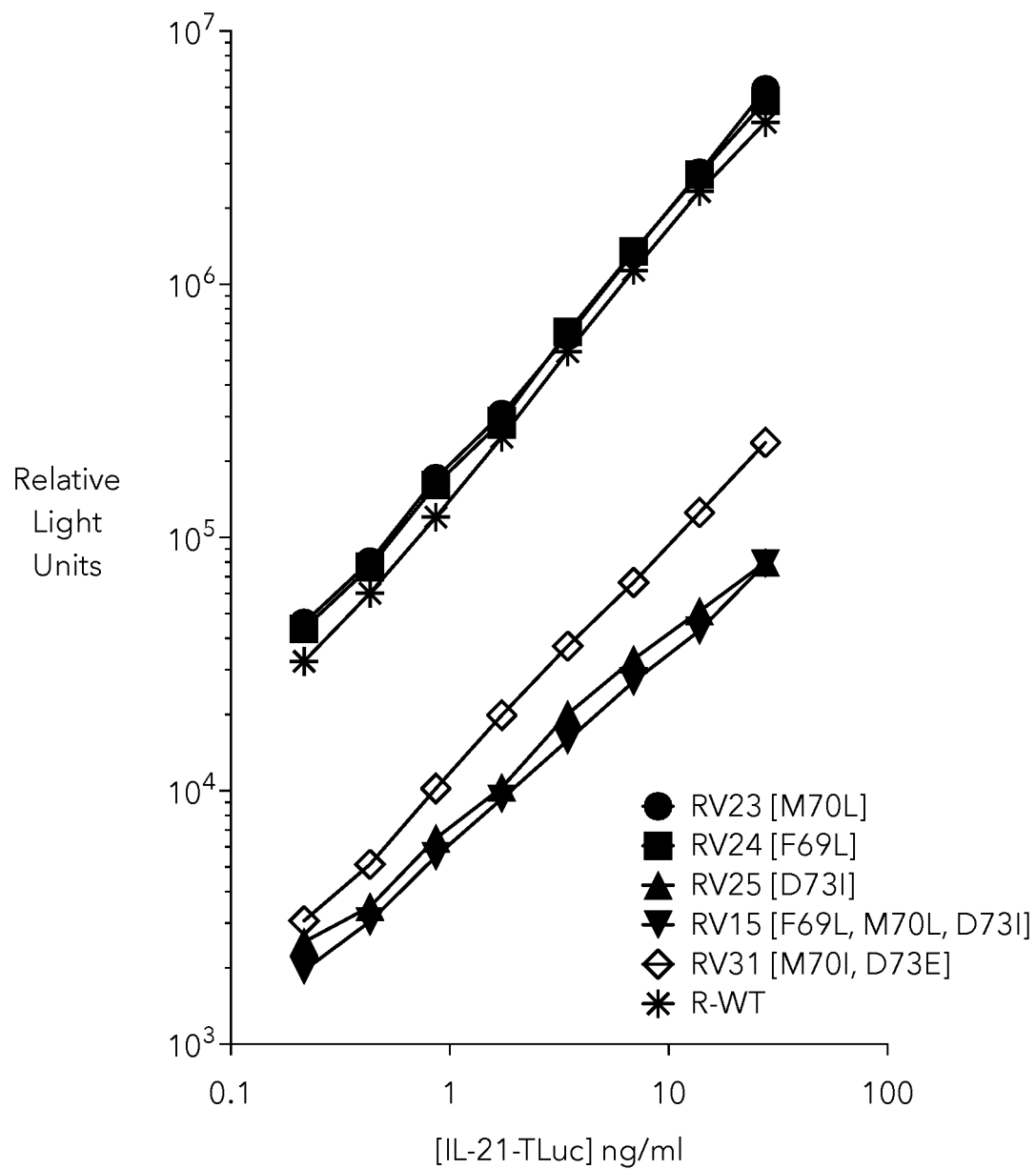
Figure 4C:
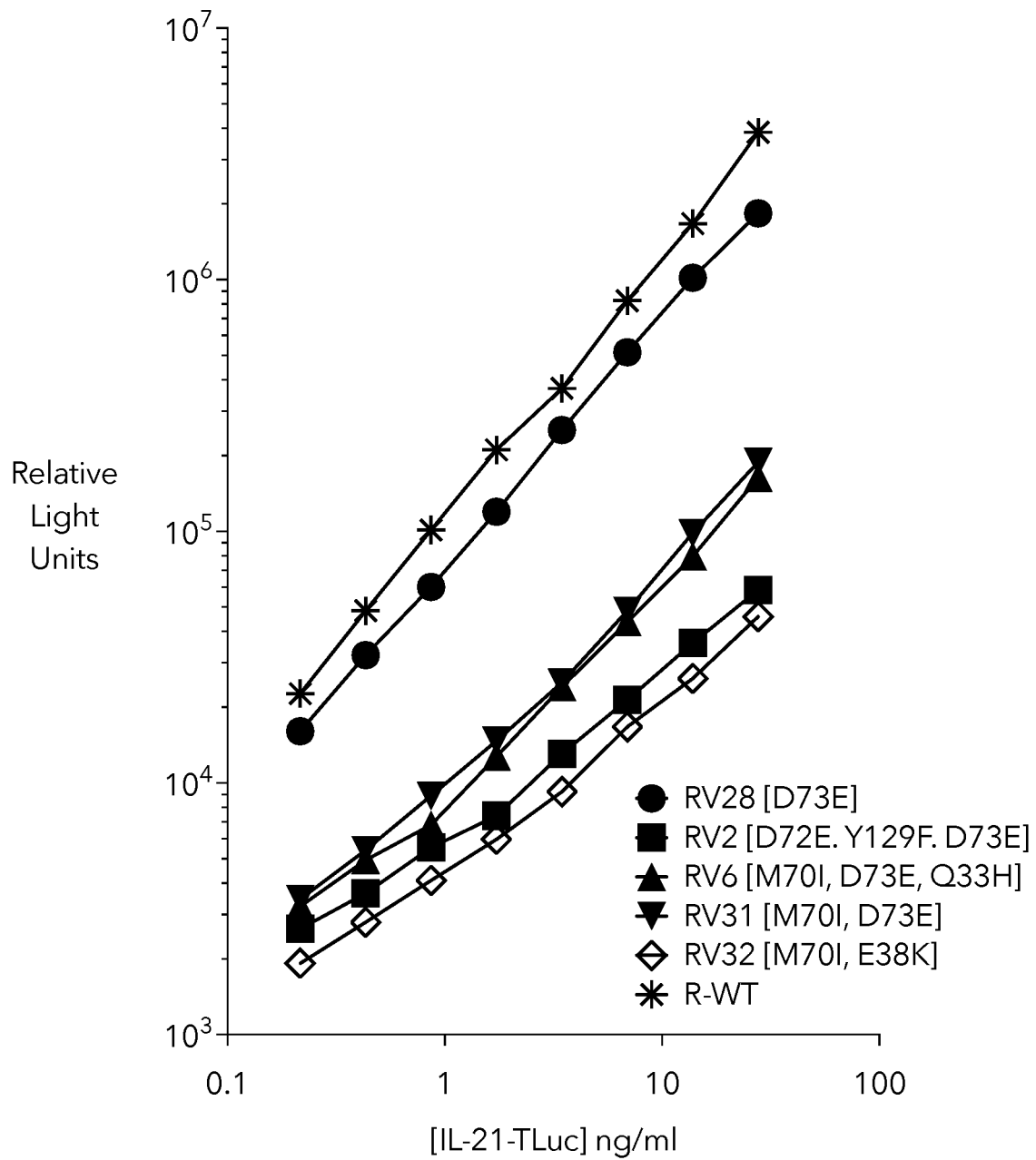
Figure 5A:
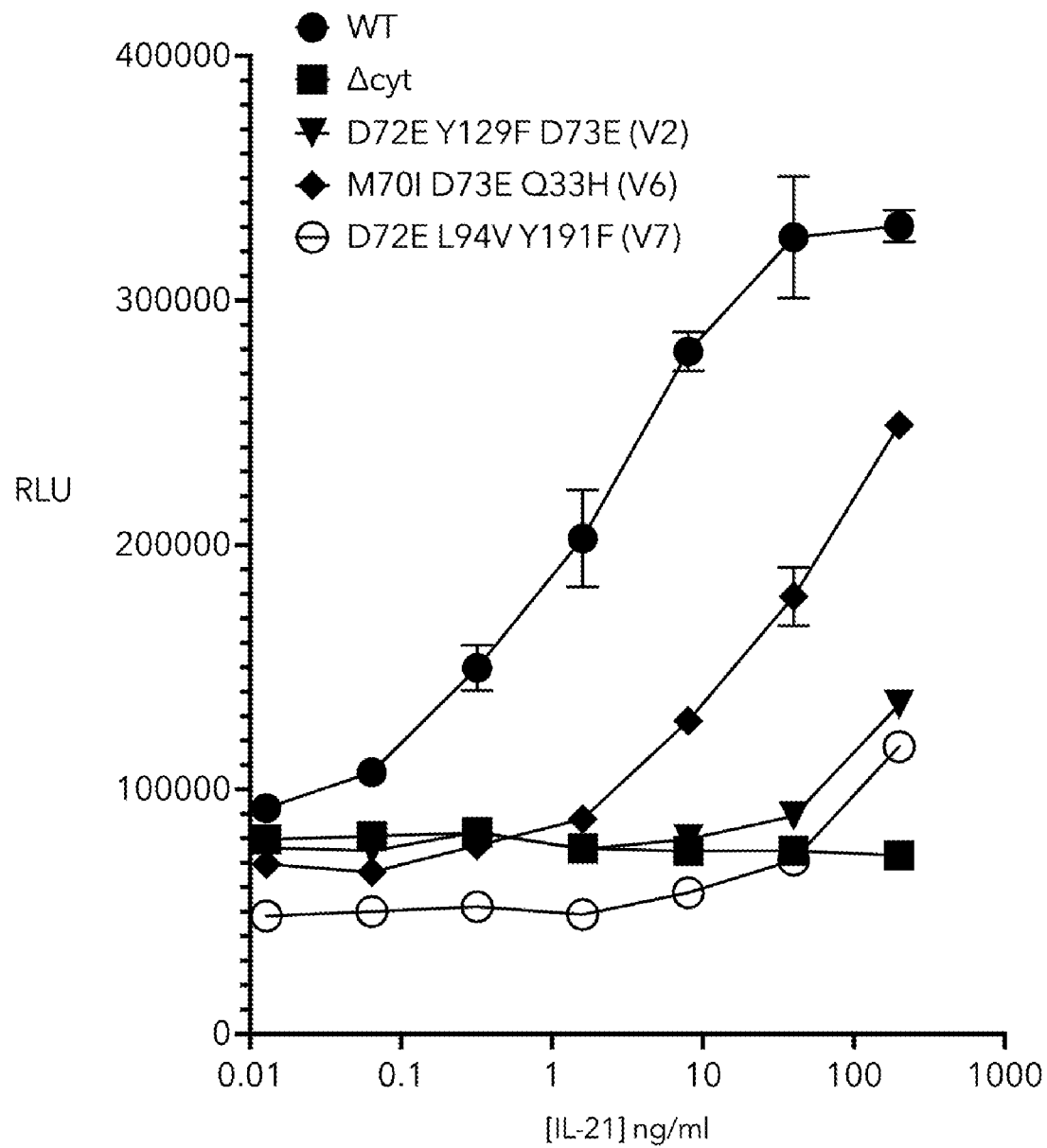
Figure 5B:
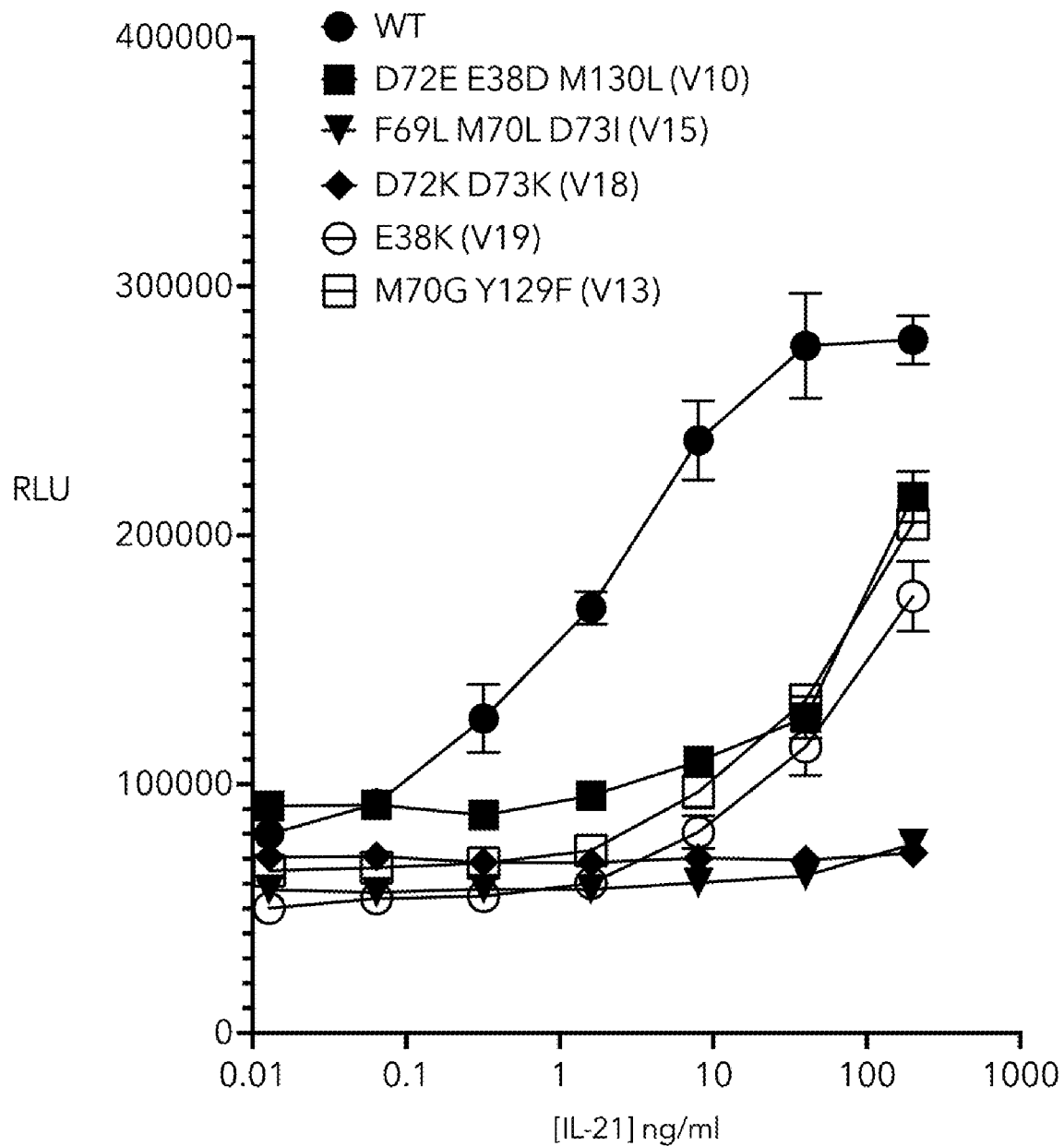
Figure 6A:
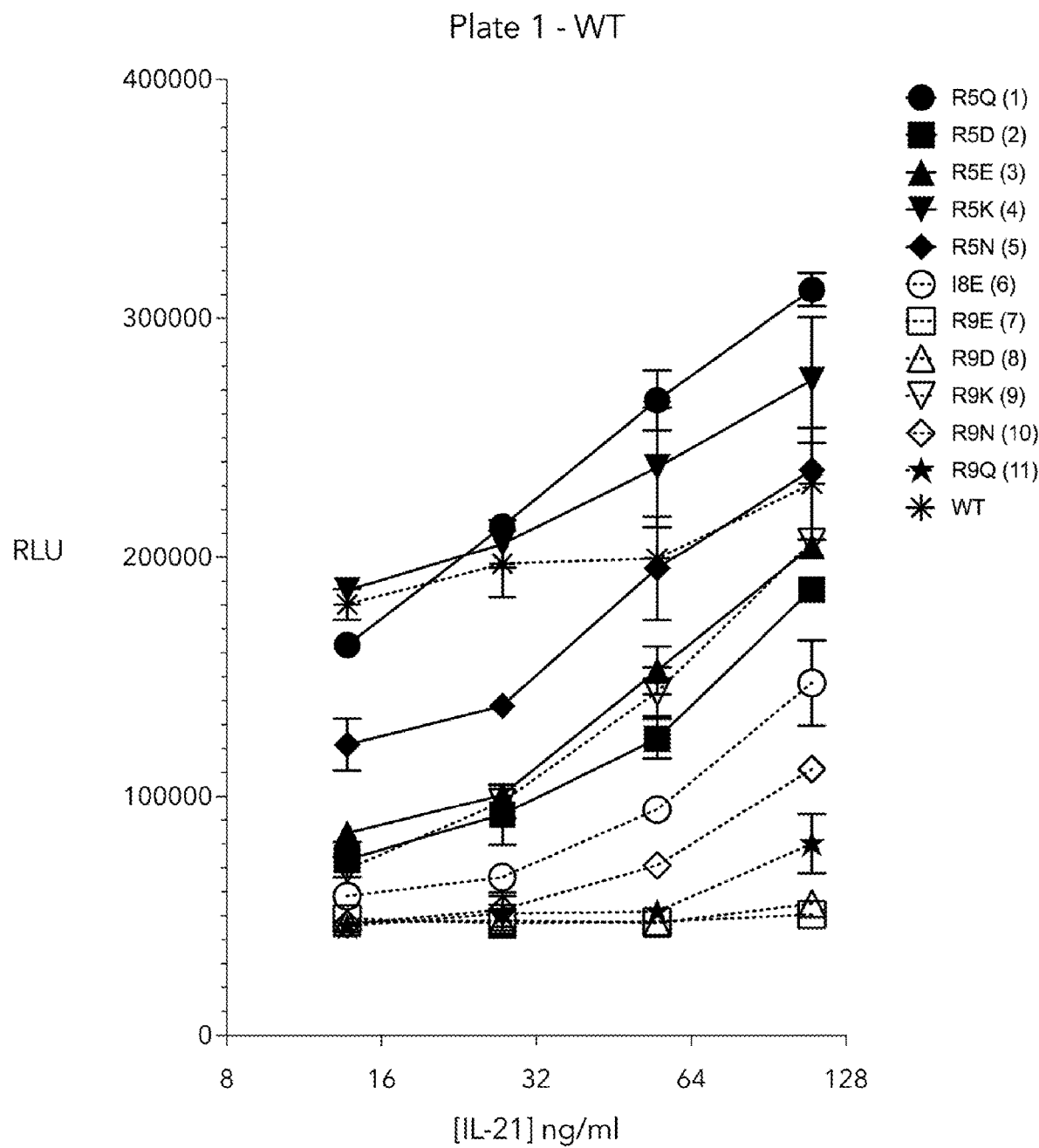
Figure 6B:
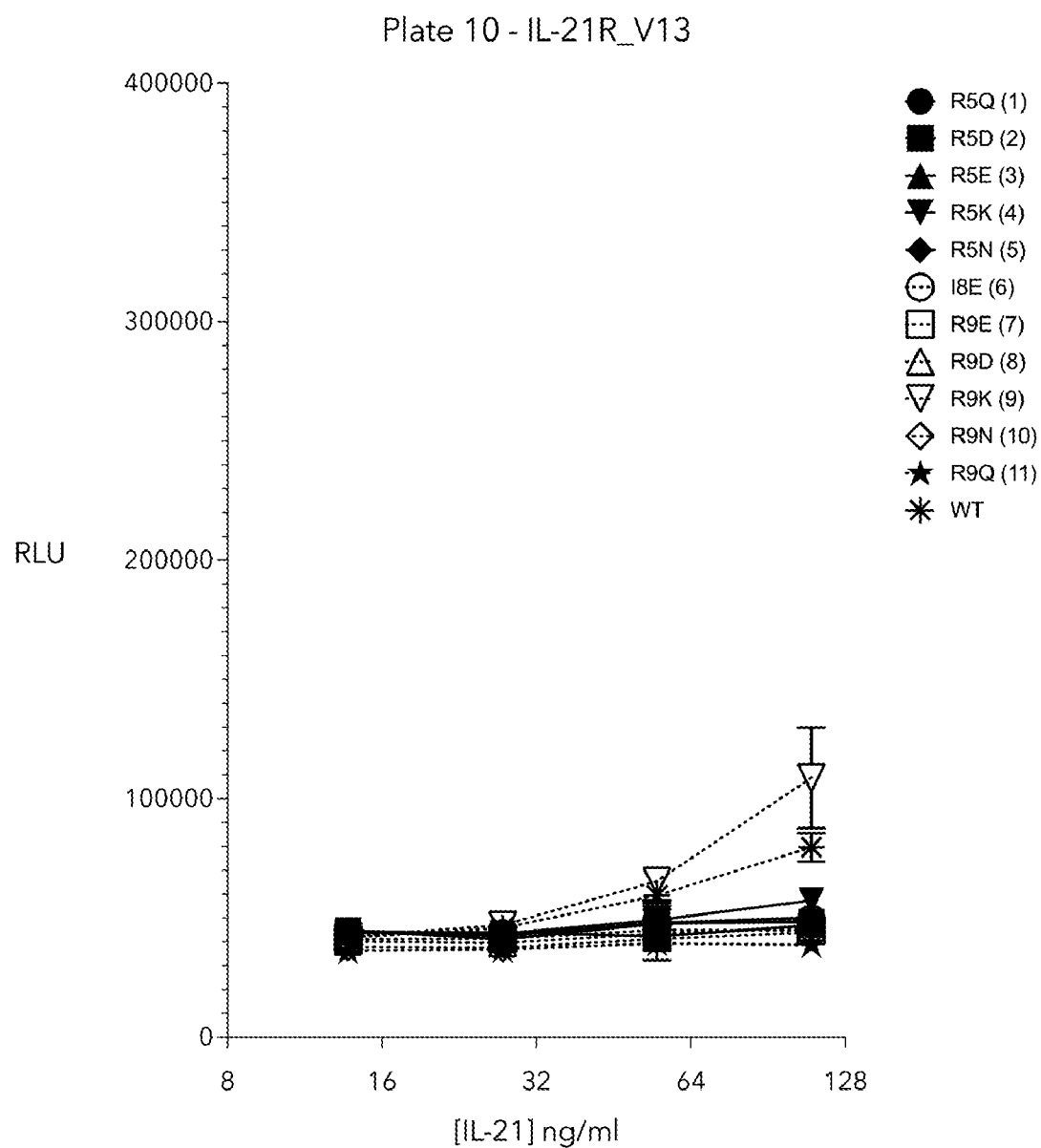
Figure 6C:
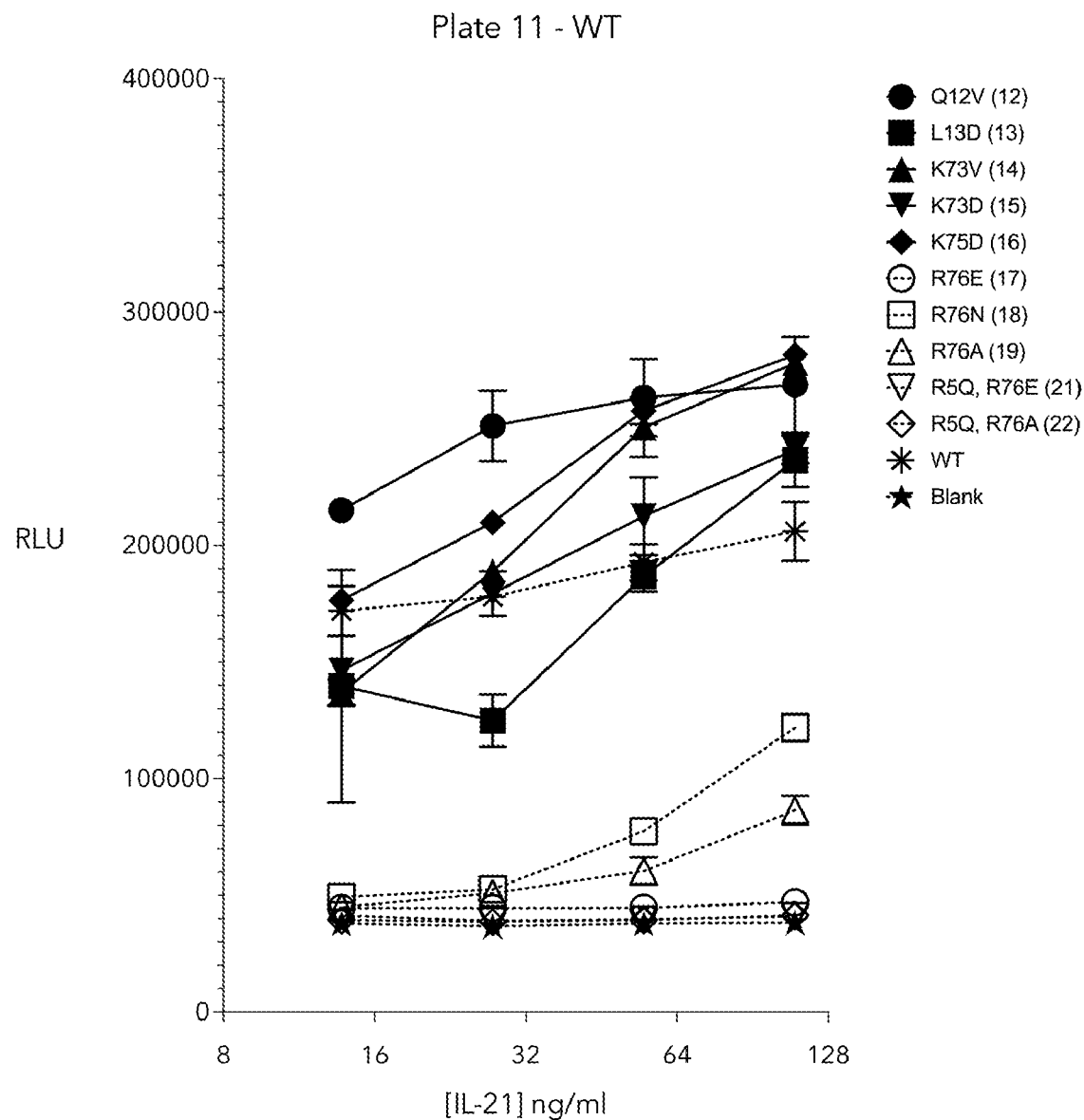
Figure 6D:
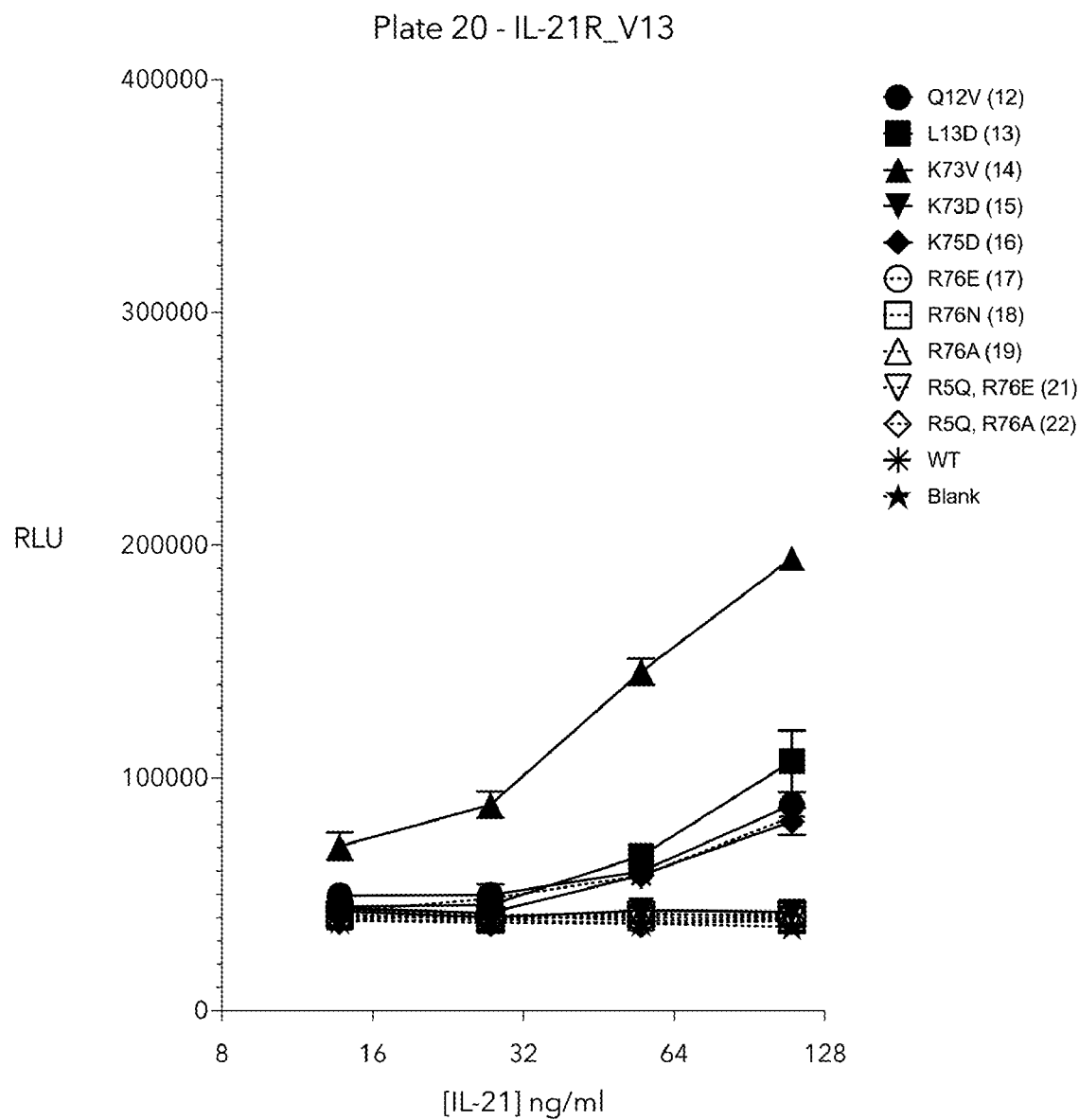
Figure 7A:
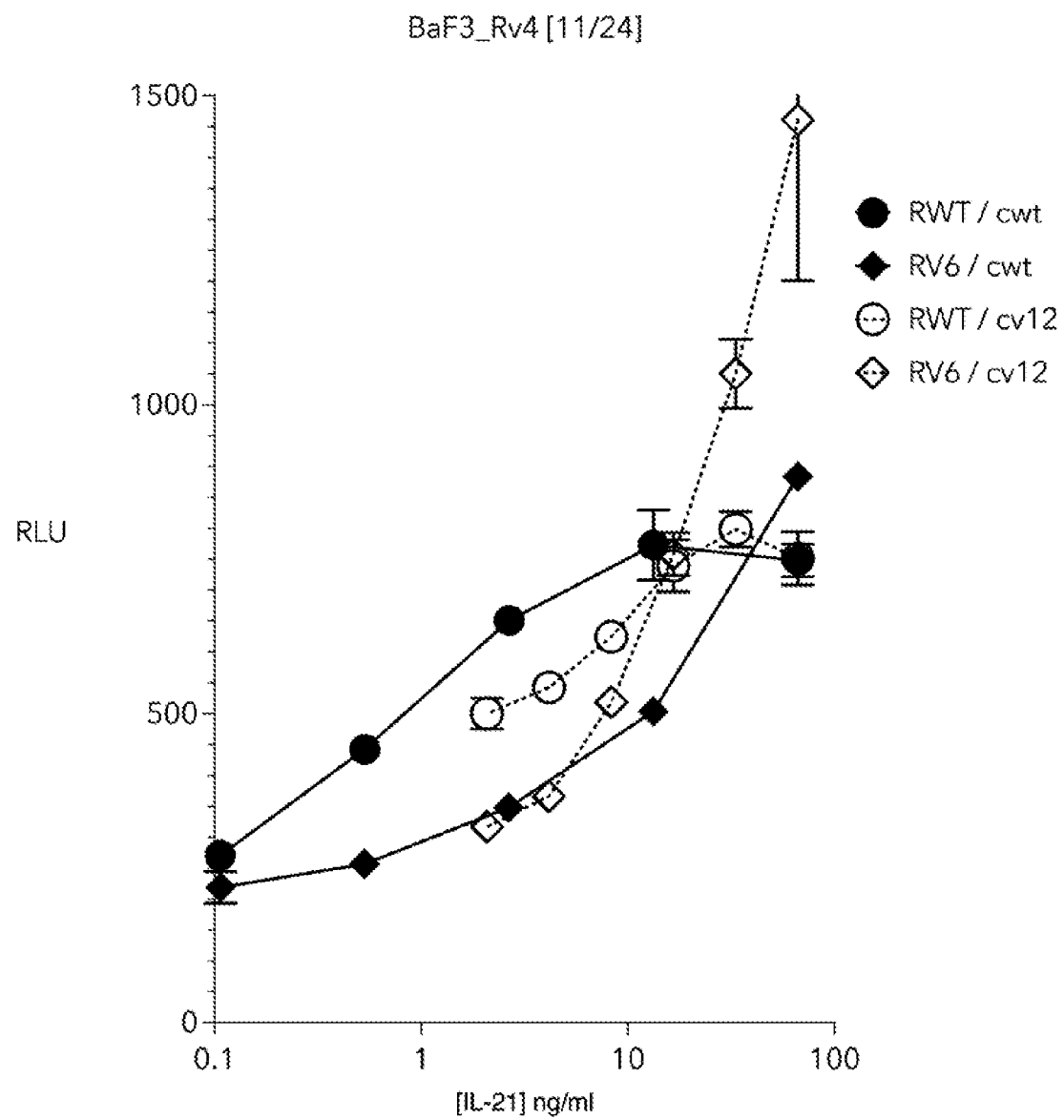
Figure 7B:
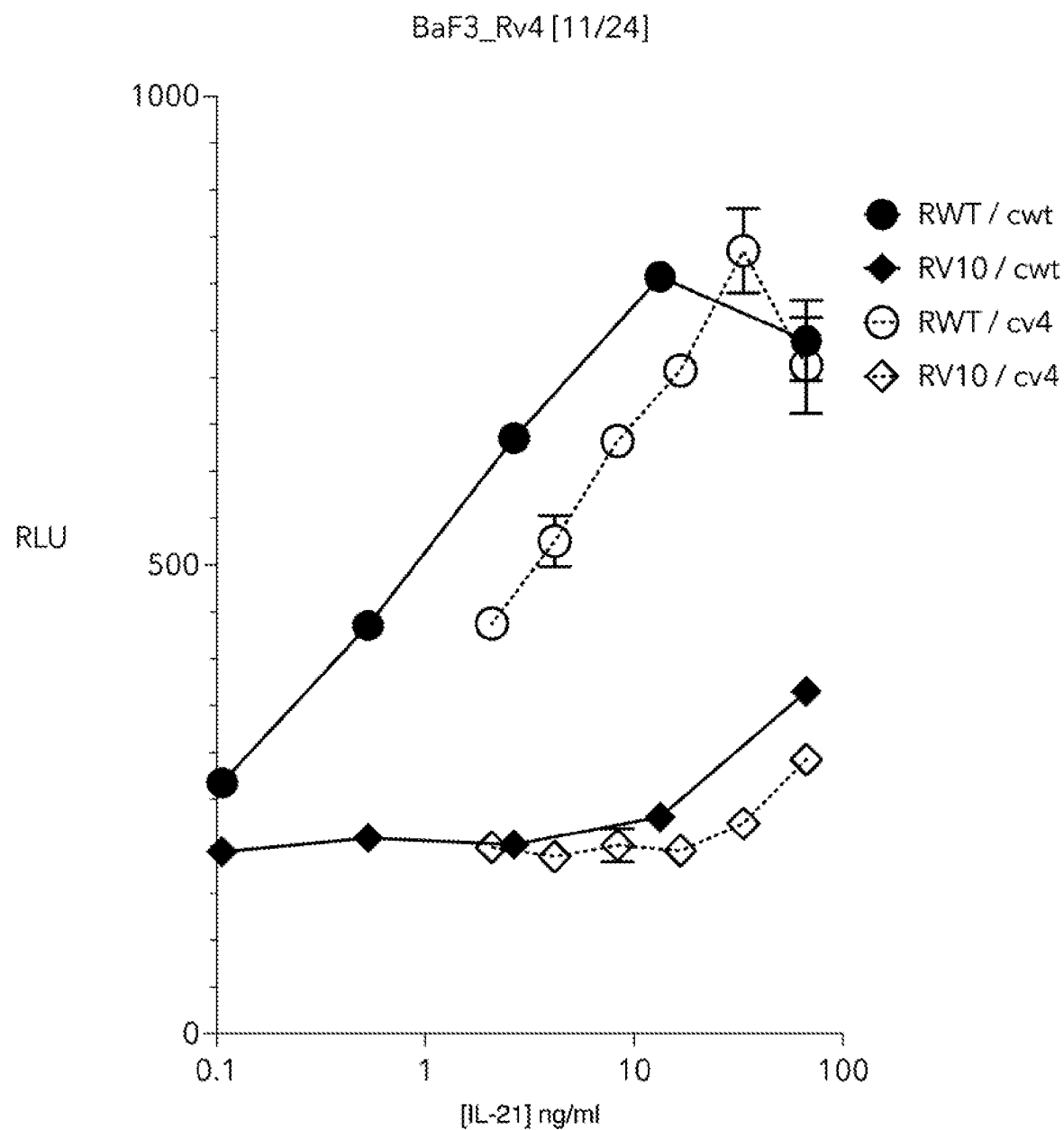
Figure 7C:
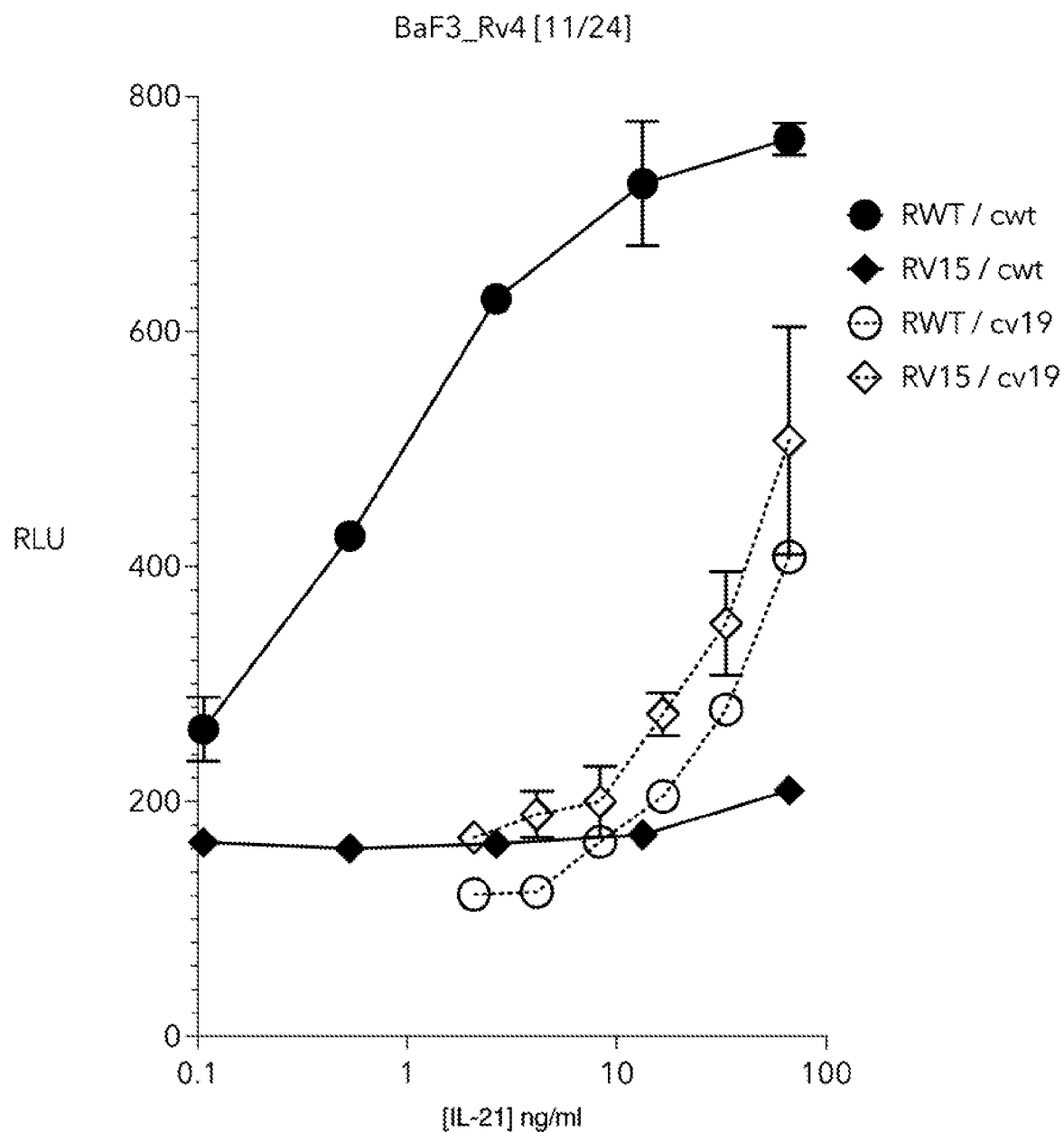
Figure 7D:
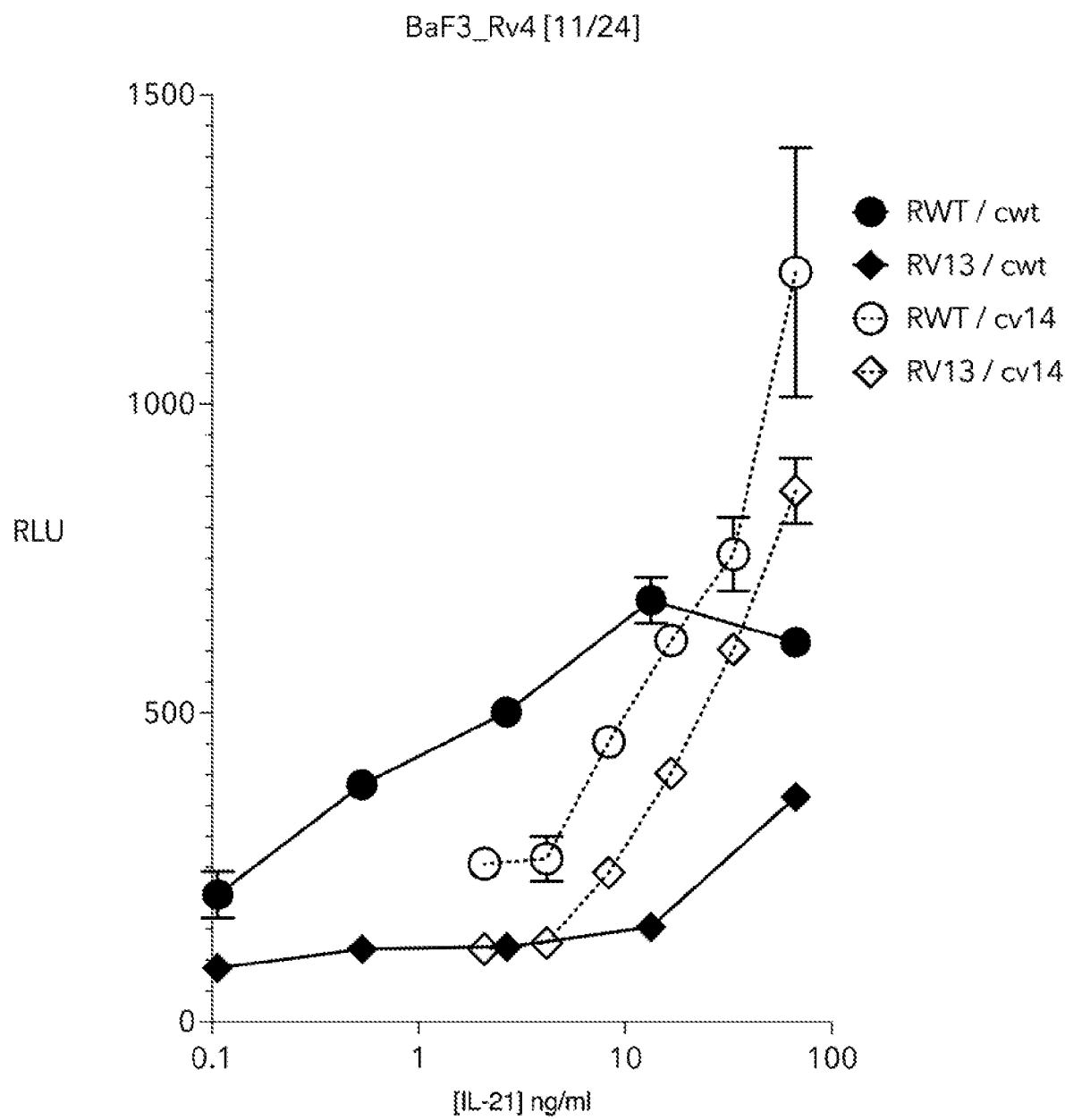

As shown in FIGS. 4A-4C, several of the candidate ortho-IL-21Rα molecules showed diminished capacity to bind IL-21-TLuc16 (i.e., ortho-IL-21Rα molecules RV23, RV24, and RV28 showed binding that was equivalent or nearly equivalent to that of the wild-type receptor, whereas all the other ortho-IL-21Rα molecules showed significantly more impaired binding).

Example 2: Attenuated IL-21-Mediated Signaling Mediated by Candidate Ortho-IL-21Rα Molecules To test further the extent to which the ortho-IL-21Rα candidates were compromised in their capacity to bind IL-21, the eight candidates from Example 1 and FIG. 3 were expressed in a lymphoid cell line, namely Ba/F3 cells (a mouse pre-B cell lymphoma line). Ba/F3 cells are dependent on the cytokine IL-3 for growth but will also proliferate robustly in response to IL-21 if first rendered positive for expression of IL-21Rα.

Ba/F3 cells were electroporated with LeapIn Transposase® mRNA and transposons encoding wild-type or ortho-IL-21Rα candidates RV2, RV6, RV7, RV10, RV13, RV15, RV18, and RV19; and Δcyt, which is a form of IL-21Rα lacking almost all of its cytoplasmic tail. The transposons also carried a STAT-3-regulated gene encoding the secreted *Cypridina noctiluca* luciferase, a constitutively expressed cytosolic click beetle luciferase, and a constitutively expressed gene encoding puromycin N-acetyl transferase.

As an example, the RV13-expression construct was prepared by oligonucleotide-dependent DNA synthesis by ATUM (www.atum.bio). This plasmid is over 13 Kb in size and comprises four independent genes within a piece of DNA that is flanked first by genomic insulator sequences (from the human D4Z4 locus on one side and from the chicken locus encoding (3-globin on the other), then by transposon inverted terminal repeat ("ITR") sequences. The insulator sequences are intended to protect the genes within the transposon from position effects (i.e., effects dependent on the site of transposon integration in the genome) that might reduce or variegate expression. The ITR sequences are recognized by ATUM's proprietary LeapIn® transposase enzymes that mediate integration of the transposon into genomic DNA. The four genes present inside the transposon are described in Table 3 (in the order they occur within the transposon). The genes and the transposon that contains them were designed according to standard molecular biology principles compatible with the construct assembly methodology used routinely by ATUM. Variants of this vector encoding wild-type or other candidate ortho-IL-21Rα molecules were generated by making appropriate changes in the fourth gene listed in Table 3.

TABLE 3

| | Promoter | Open Reading Frame | Terminator | Relative orientation |
|---|---|---|---|---|
| PGK-puro | Human PGK | *Streptomyces* Puromycin-N-actely transferase | Human beta-globin | Antisense |
| STAT3-cLuc | Minimal promoter from the cytomegalovirus immediate early gene 1, preceded by six STAT3 binding sites | *Cypridina noctiluca* luciferase | Human alpha-globin | Sense |
| EEF2-eLuc | Mouse EEF2 | *Pyrearinus termitilluminans* luciferase | *Bos taurus* growth hormone | Sense |
| HSV-IL-21R-RV13 | Attenuated promoter from herpes simplex virus 1 | Human IL-21Ra RV13 (M70G/Y129F) | *Oryctolagus cuniculus* beta-globin | Sense |

The transposon vector encoding wild-type IL-21Rα or any one of the candidate ortho-IL-21Rα molecules was co-transfected into Ba/F3 cells together with in vitro-transcribed mRNA encoding the relevant LeapIn® transposase using either the MaxCyte ATx or ThermoFisher Neon instruments according to the manufacturer's instructions. Puromycin selection (1 μg/ml or higher) was imposed at 48 hours after transfection and continued for at least a week after all the cells in an untransfected control culture had died. Flow cytometry was used to confirm that the puromycin-selected cells showed uniform expression of IL-21Rα.

To assay IL-21 responses, the Ba/F3 cells were first incubated for 20-24 hours in RPMI-1640 medium lacking serum and exogenous cytokines. After washing, they were stimulated with IL-21 (in the presence of 0.4% [vol/vol] serum) for a further 20-24 hours with varying concentrations of IL-21 (or candidate ortho-IL-21) in round-bottom 96-well plates (~100,000 cells per well) before assaying secreted luciferase (from the STAT3-cLuc gene in the transposon), intracellular luciferase (from the constitutively expressed EEF2-eLuc gene in the transposon), or ATP accumulation. The secreted luciferase assay was used to inform on STAT3-dependent signaling in the cells, as occurs when IL-21 engages its receptor. The other two assays (monitoring cytoplasmic eLuc or ATP accumulation) were used to inform on cell number (i.e., proliferation).

As expected, Ba/F3 cells failed to proliferate if they were not provided IL-3. When expressing the wild-type form of IL-21Rα, they showed IL-21-dose-dependent proliferation (by ATP or eLuc assay as mentioned above). There was also IL-21-dose-dependent accumulation of *Cypridina* luciferase (from the STAT3-regulated reporter gene) in the supernatant fluids from treated cultures (FIGS. 5A-B). The secretion of *Cypridina* luciferase depended on the IL-21Rα cytoplasmic domain (because a tailless form of IL-21Rα [Δcyt] did not induce proliferation in response to IL-21; FIG. 5A); the secretion was also significantly impaired when the tyrosine residues in the cytoplasmic domain were replaced with phenylalanine residues (not shown).

*Cypridina noctiluca* luciferase activity was readily detected by adding the relevant luciferase substrate (Vargulin) to samples of supernatant fluids from the cells and measuring light emission using a luminometer. FIGS. 5A and 5B show luciferase activity detected as light emission (relative light units or RLU) following admixture of 20 μL of the supernatant fluid from each of the wells with 50 μL of VLAR-2 reagent buffer (Targeting Systems) containing Vargulin at the manufacturer's recommended concentration.

The results confirmed the findings of the binding assays described and shown in Example 1 and FIG. 3 with respect to impaired IL-21-dependent signaling mediated by the eight candidate ortho-IL-21Rα molecules.

Example 3: Screening of Candidate Ortho-IL-21 Molecules: Testing for STAT3-Dependent Signaling Responses in Cells Expressing RV13 or Wild-Type IL-21Rα

Wild-type or candidate ortho-IL-21 molecules were produced from transiently transfected HEK-293 cells according to procedures that are routinely used at ATUM (www.atum.bio). Expression vectors for this purpose carried the IL-21 open reading frame downstream of an optimized cytomegalovirus Immediate Early Gene 1 promoter. A signal peptide from the human IL-2 gene was used in place of the native one. Epitope tags for detection, quantitation, immobilization, or purification were fused to the amino- or carboxy-termini of the IL-21 coding sequence. In one series of vectors (including those encoding the forms of IL-21 specified as CV1-CV19, CV21, CV22, and CV204 in Table 4), the element fused to the amino terminus was a Twin-Strep-Tag followed by three copies of a Glycine-Glycine-Glycine-Glycine-Serine linker moiety, while the element fused to the carboxy terminus comprised two copies of the same Glycine-Glycine-Glycine-Glycine-Serine linker followed by an N-Myc epitope tag (recognized by the 9E10 monoclonal antibody). A second series of vectors (including those encoding the forms of IL-21 specified as CV374 and CV388 in Table 4) featured no tags at the carboxy terminus but had the following element at the amino-terminus of IL-21: Twin-Strep-Tag followed immediately by the N-Myc epitope tag then three copies of the Glycine-Glycine-Glycine-Glycine-Serine linker moiety.

Cultures (10 mL) of transfected cells were maintained for approximately five days (until viability dropped below about 50%). The supernatant fluids were harvested, filtered, and aliquoted. Quantitation of the IL-21 present in the supernatant fluids was accomplished using ELISAs (and in some cases Biolayer interferometry assays) directed against the various epitope tags or specific for the IL-21 moiety.

The candidate ortho-IL-21 molecules (mature protein sequences, including epitope tags but absent the signal peptide) are shown in Table 4.

TABLE 4

| CV | SEQ ID NO: |
|---|---|
| CV1 (RQ5) | 61 |
| CV2 (R5D) | 62 |
| CV3 (R5E) | 63 |
| CV4 (R5K) | 64 |
| CV5 (R5N) | 65 |
| CV6 (I8E) | 66 |
| CV7 (R9E) | 67 |
| CV8 (R9D) | 68 |
| CV9 (R9K) | 69 |
| CV10 (R9N) | 70 |
| CV11 (R9Q) | 71 |
| CV12 (Q12V) | 72 |
| CV13 (L13D) | 73 |
| CV14 (K73V) | 74 |
| CV15 (K73D) | 75 |
| CV16 (K75D) | 76 |
| CV17 (R76E) | 77 |
| CV18 (R76N) | 78 |

TABLE 4-continued

| CV | SEQ ID NO: |
|---|---|
| CV19 (R76A) | 79 |
| CV21 (R5Q, R76E) | 80 |
| CV22 (R5Q, R76A) | 81 |
| CV204 | |
| CV374 | |
| CV388 | |

Ba/F3 cells expressing wild-type IL-21Rα or RV13 were stimulated with candidate ortho-IL-21 molecules CV1-CV19, CV21, and CV22. The signaling responses of the Ba/F3 cells to the ortho-IL-21 molecules were monitored as above using the STAT3-luciferase assay.

Ba/F3 cells were exposed to four concentrations (100, 50, 25, and 12.5 ng/mL) of the indicated candidate ortho-IL-21 molecules (FIGS. 6A and 6B: candidate ortho-IL-21 molecules CV1-CV11 and wild-type IL-21; FIGS. 6C and 6D: candidate ortho-IL-21 molecules CV12-CV19, CV21, CV22, and wild-type IL-21). The cells were placed in serum-free medium for 24 hours before a subsequent overnight incubation (~20 hours) with the candidate ortho-IL-21 molecules in round-bottom 96-well plates (~100,000 cells per well). As described above, the transposon conferring expression of WT and RV13 also carried a STAT3-regulated gene encoding the secreted *Cypridina noctiluca* luciferase. FIGS. 6A-6D show activity of this luciferase detected as light emission (relative light units) following admixture of 20 μL of the supernatant fluid from each of the wells with 50 μL of VLAR-2 reagent buffer (Targeting Systems) containing the *Cypridina noctiluca* luciferase substrate (Vargulin) at the manufacturer's recommended concentration.

As shown in FIGS. 6A-6D, RV13 made measurable responses to at least CV9 (bearing an R9K substitution) and C14 (bearing a K73V substitution).

Cells expressing IL-21Rα (the wild-type receptor) made measurable responses to the majority of variant cytokines, though importantly, the design of the experiment (featuring only four relatively high concentrations of the variant cytokines) precluded the possibility of quantifying the extent of their signaling activity relative to wild-type IL-21.

Selected candidate ortho-IL-21 molecules from the collection represented in FIGS. 6A-6D and Table 4 (namely CV4, CV12, CV19, and CV14) were re-tested with Ba/F3 cells expressing wild-type IL-21Rα or candidate ortho-IL-21Rα molecules RV6, RV10, RV13, or RV15. The results of this experiment are shown in FIGS. 7A-7D. As expected, when exposed to wild-type IL-21, cells expressing the candidate ortho-IL-21Rα molecules made diminished signaling responses compared to those expressing wild-type IL-21Rα (solid lines with filled symbols in each graph). Furthermore, as predicted by the results in FIGS. 6A-6D, in three cases (for cells expressing candidate ortho-IL-21Rα molecules RV6, RV19, or RV13) the cells made stronger responses when they were exposed to the candidate ortho-IL-21 molecules (CV12, CV19, or CV14, respectively) than to wild-type IL-21 (open versus closed diamond symbols in FIGS. 7A, C, and D, respectively). All four candidate ortho-IL-21 molecules were impaired to varying extents in their capacity to cause responses via wild-type IL-21Rα, with candidate ortho-IL-21 molecule CV19 being the most severely compromised in this respect (open versus closed circle symbols in FIG. 7C).

The results of these experiments identified IL-21 substitutions associated with impaired capacity to signal via wild-type IL-21Rα with—in some cases—low-level capacity to induce signaling via specific candidate ortho-IL-21Rα molecules.

Figure 8A:
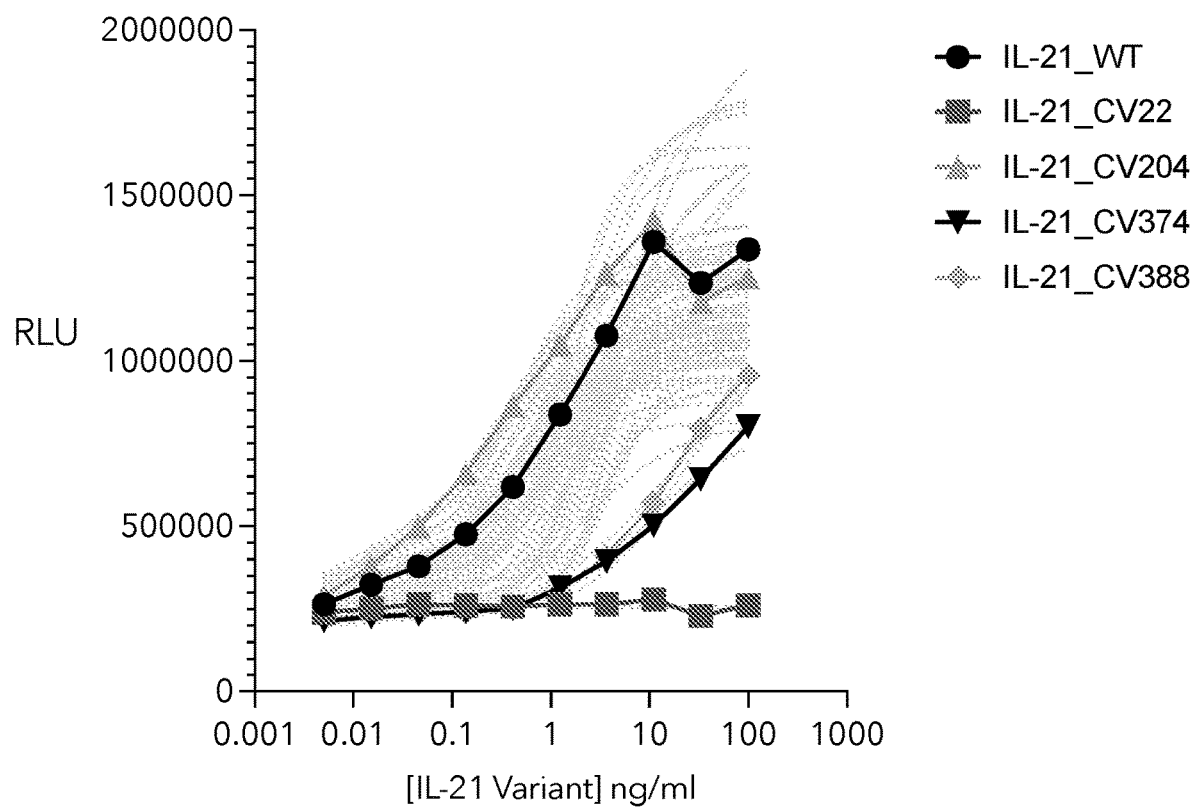
Figure 8B:
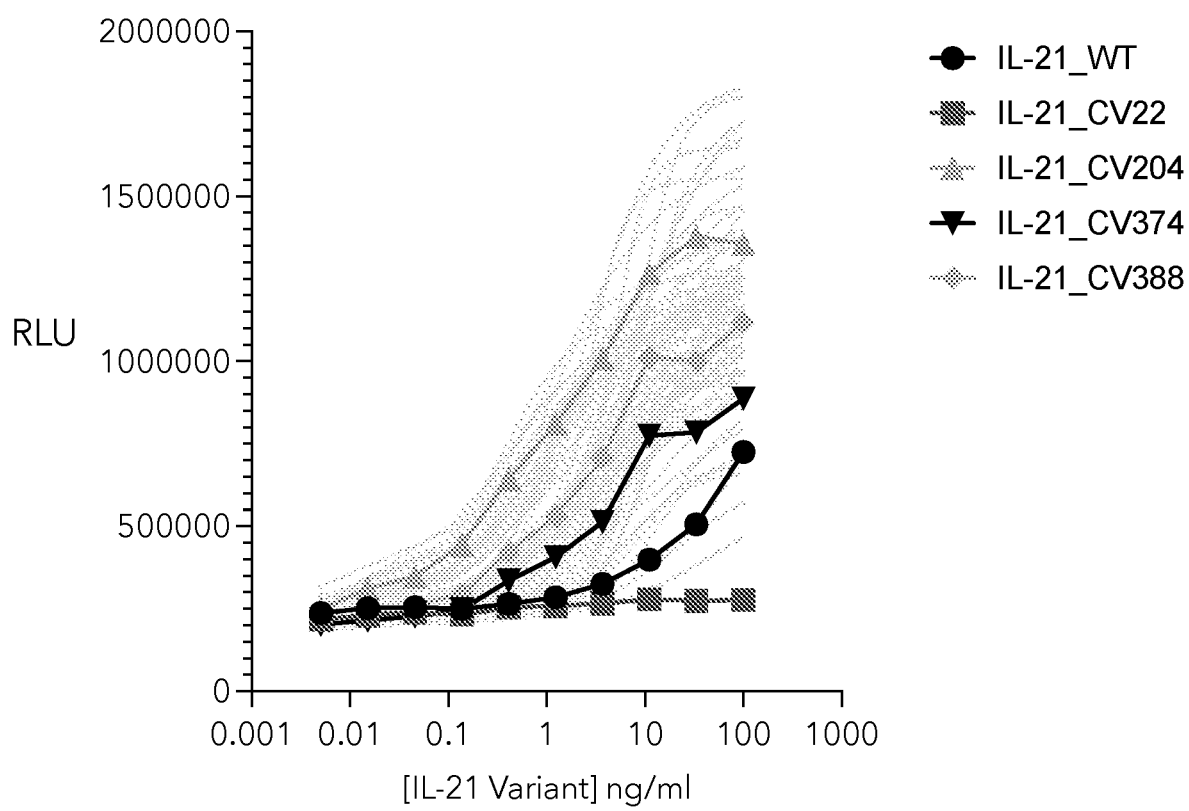
Figure 8C:
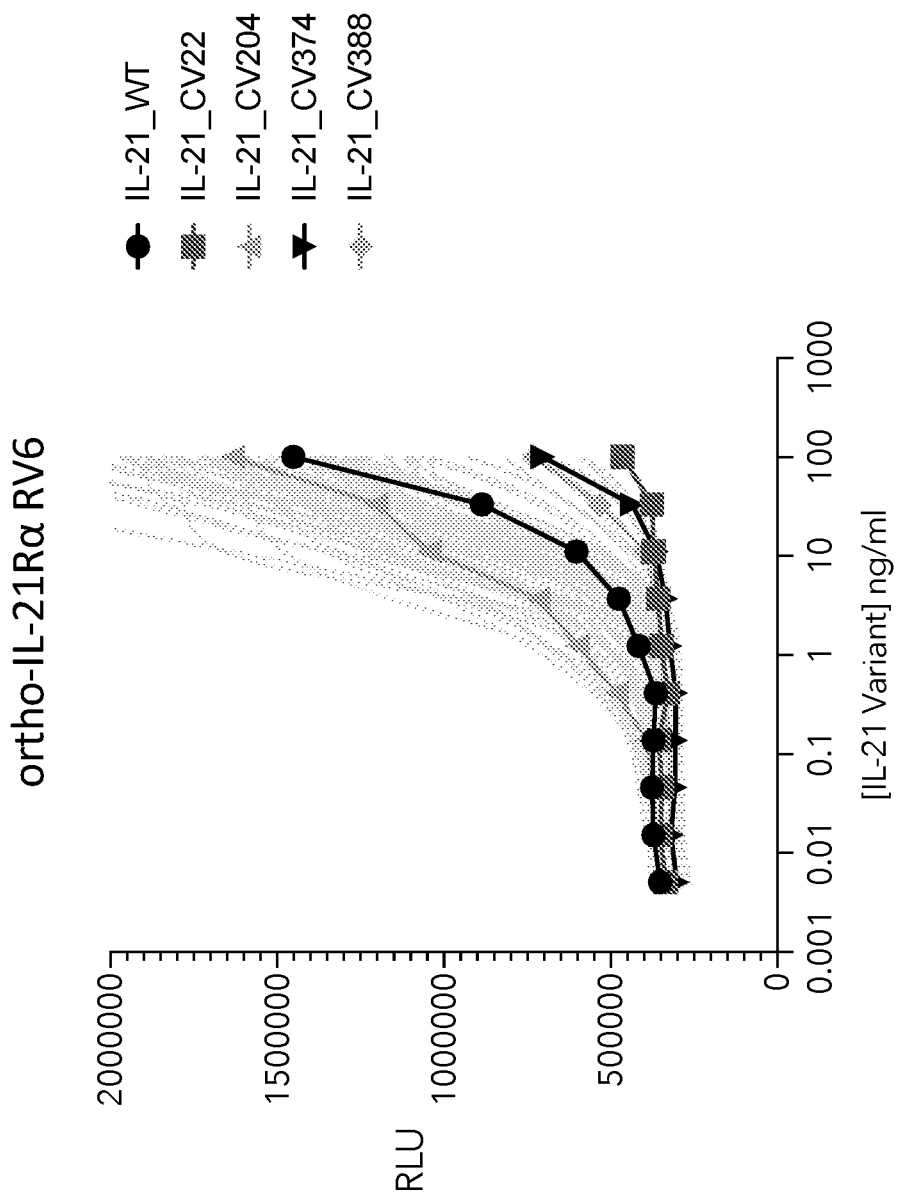

Infolog variants of IL-21 were generated according to the principles described in Govindarajan S, Mannervik B, Silverman J A, et al. Mapping of amino acid substitutions conferring herbicide resistance in wheat glutathione transferase. A CS Synth Biol. 2015; 4(3):221-227. Doi:10.1021/sb500242x and Musdal Y, Govindarajan S, Mannervik B. Exploring sequence-function space of a poplar glutathione transferase using designed information-rich gene variants. *Protein Eng Des Sel.* 2017; 30(8):543-549. Doi:10.1093/protein/gzx045. These Infolog variants of IL-21 were screened for their capacity to induce signaling in Ba/F3 cells expressing wild-type IL-21Rα or candidate ortho-IL-21Rα molecules as described. Representative data from one such screening experiment are provided in FIGS. 8A-8C. The experimental results depicted in FIGS. 8A-8C derived from the analysis of 96 cytokines, one of which comprised the wild-type form of IL-21, another comprised a negative control variant (CV22, which bears two disabling substitutions [R5Q/R76A]), and 94 Infolog variants, each of which was a candidate ortho-IL-21 molecule. FIG. 8A shows the STAT3 responses elicited in cells expressing wild-type IL-21Rα exposed to the cytokine collection, whereas FIGS. 8B and 8C show responses made by cells expressing the candidate ortho-IL-21Rα molecules RV13 and RV6, respectively. The highlighted curves in the three figures show responses made by the three kinds of cells to five selected cytokines, namely, wild-type IL-21, CV22, CV204, CV374, and CV388.

Figure 9A:
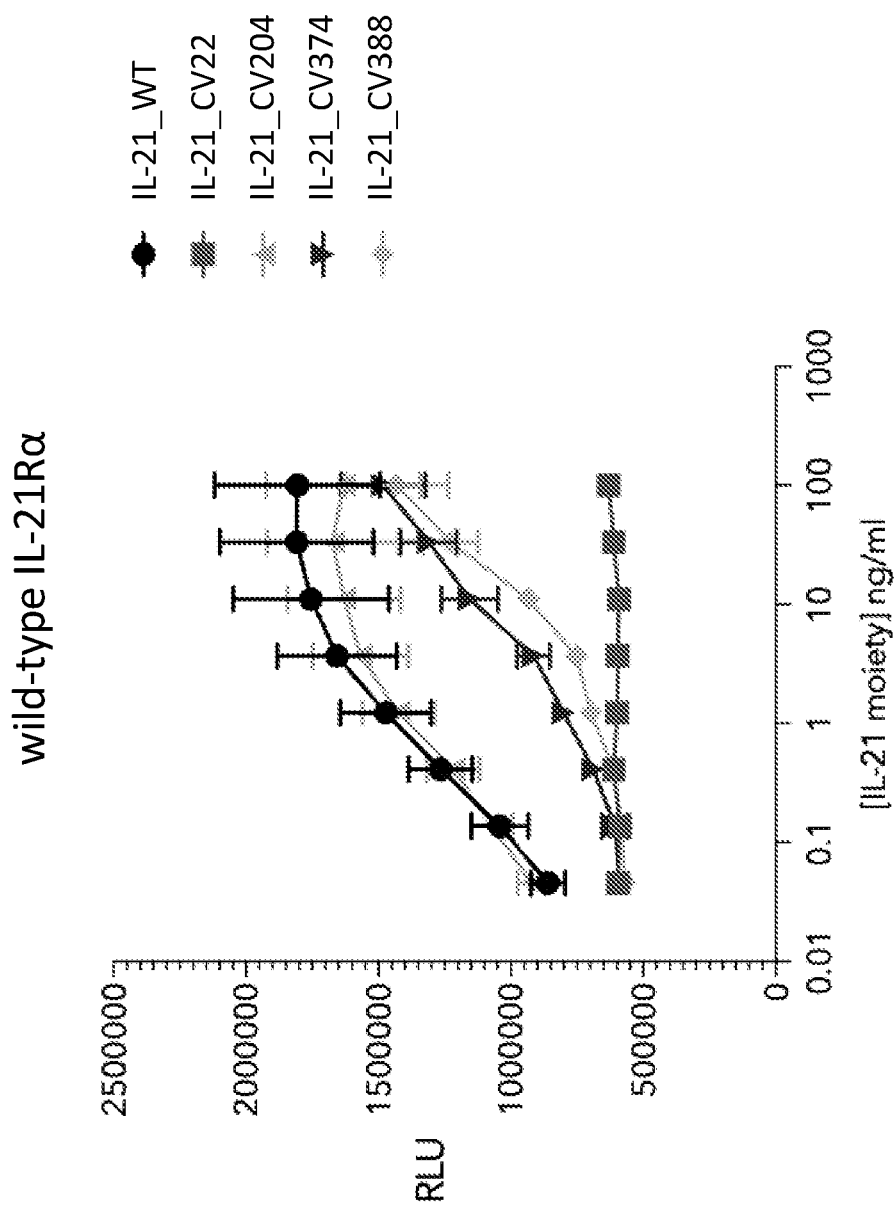

The highlighted cytokines were subsequently retested in an independent, focused experiment of a similar design (involving Ba/F3 cells expressing wild-type IL-21Rα (FIG. 9A) or the candidate ortho-IL-21Rα RV13 (FIG. 9B)). As in the screening experiment (FIGS. 8A-8C), CV22, the negative control cytokine, failed to elicit a signaling response in cells expressing either form of IL-21Rα. By contrast, wild-type IL-21 induced a strong response in cells expressing the wild-type form of IL-21Rα, but a much weaker response in the RV13-expressing cells. CV204 elicited a response in cells expressing wild-type IL-21Rα (FIGS. 8A and 9A) or either of the candidate ortho-IL-21Rα molecules (FIGS. 8B, 8C, and 9B).

Figure 9B:
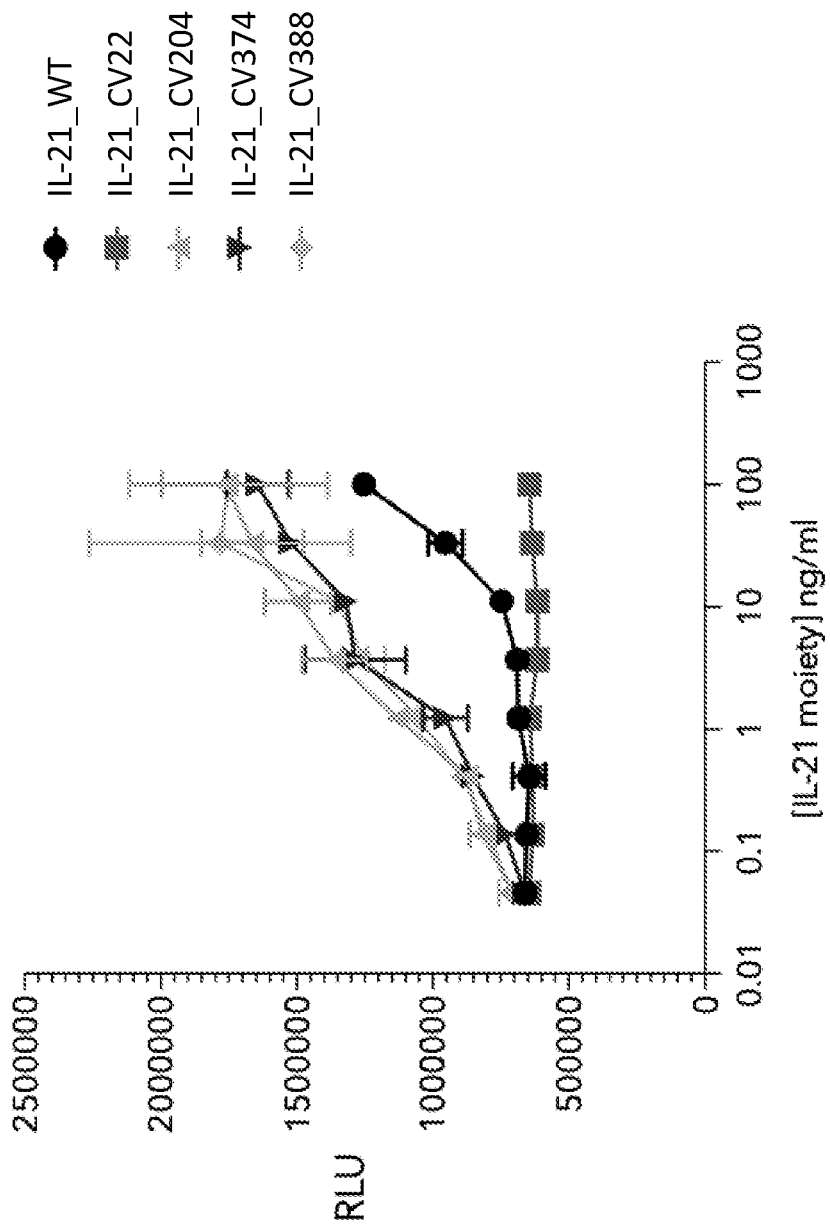

Strikingly, CV374 and CV388 were significantly compromised in their capacity to induce signaling in cells expressing wild-type IL-21Rα (FIGS. 8A and 9A) but, like CV204, demonstrated good activity with cells expressing RV13 (FIGS. 8B and 9B). In this Ba/F3 assay, therefore, ortho-IL-21 molecules CV374 and CV388 showed the kind of signaling selectivity expected of cytokines that have orthogonal functionality to native IL-21.

Figure 10B:
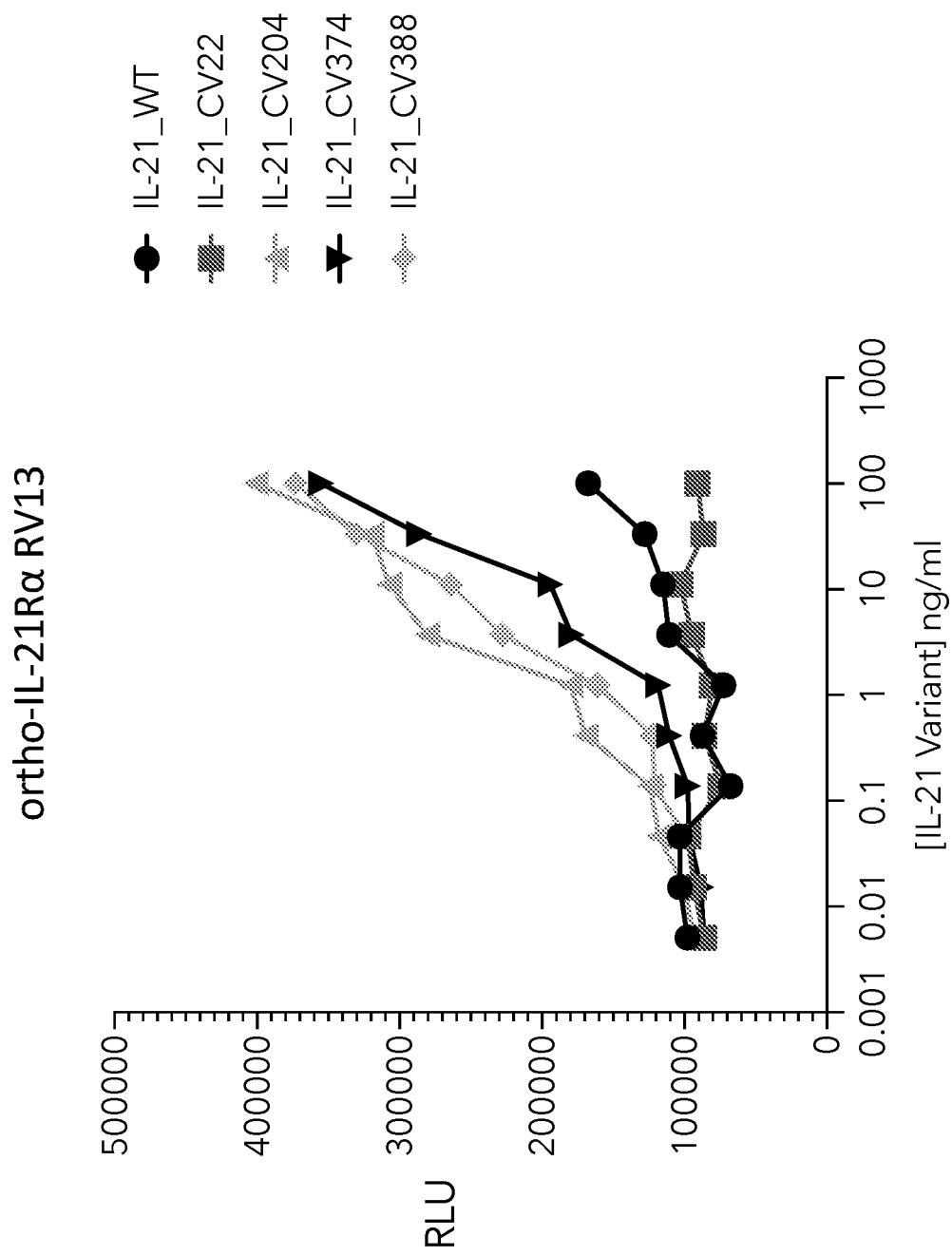
Figure 10C:
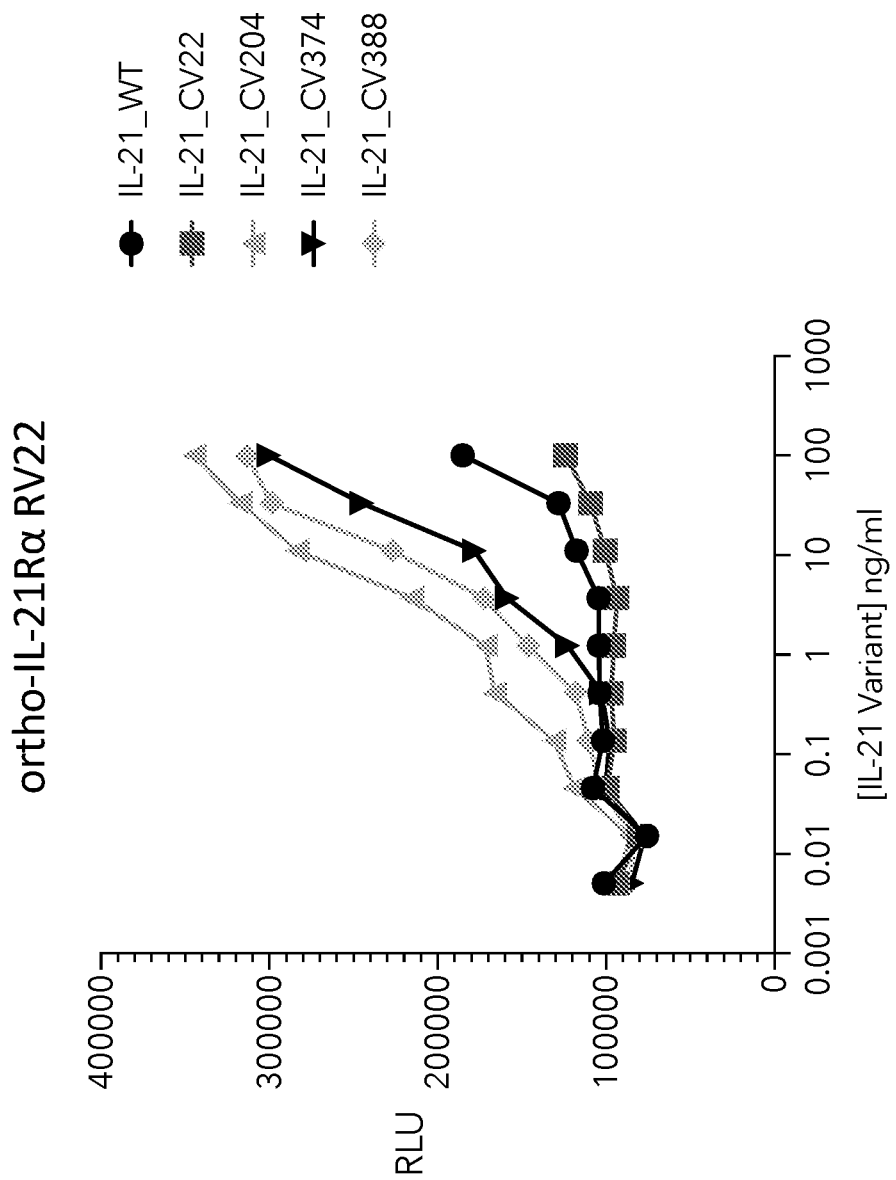

RV13 carries two substitutions relative to wild-type IL-21Rα, namely M70G and Y129F, whereas RV22 carries just M70G. These two variant receptors appear to be equivalently compromised in their capacity to bind native IL-21 (FIG. 4A). They also accounted for a similar pattern of reactivity to the collection of IL-21 molecules used in FIGS. 9A and 9B. Specifically, like RV13 (FIG. 10B), RV22 mediated significantly impaired signaling responses to wild-type IL-21 (and the negative control molecule CV22) but conferred good responses to CV204, CV374, and CV388 (FIG. 10C). As in FIG. 9A, both CV374 and CV388 showed impaired responses with cells expressing wild-type IL-21Rα, while CV204 behaved similarly to wild-type IL-21 (FIG. 10A). These results replicate the key observations made from the data in FIGS. 9A and 9B, while also showing that RV22 may be interchangeable with RV13.

An additional series of candidate ortho-IL-21 molecules was generated. These variants included a majority that were based on CV374 and CV388 but carried alternative substitutions predicted to impact binding to wild-type IL-21Rα and the candidate ortho-IL-21Rα molecule RV22, either on the basis of prior screening data (e.g., FIGS. 8A-8C) or from the published crystal structure of the IL-21 cytokine-receptor complex. As an example, candidate ortho-IL-21 variant CV414 resembles CV388, differing only in the absence of a substitution at position 104. Similarly, candidate ortho-IL-21 variant CV415 resembles CV388 but includes the G84E substitution present in CV374 and P104V.

Figure 11A:
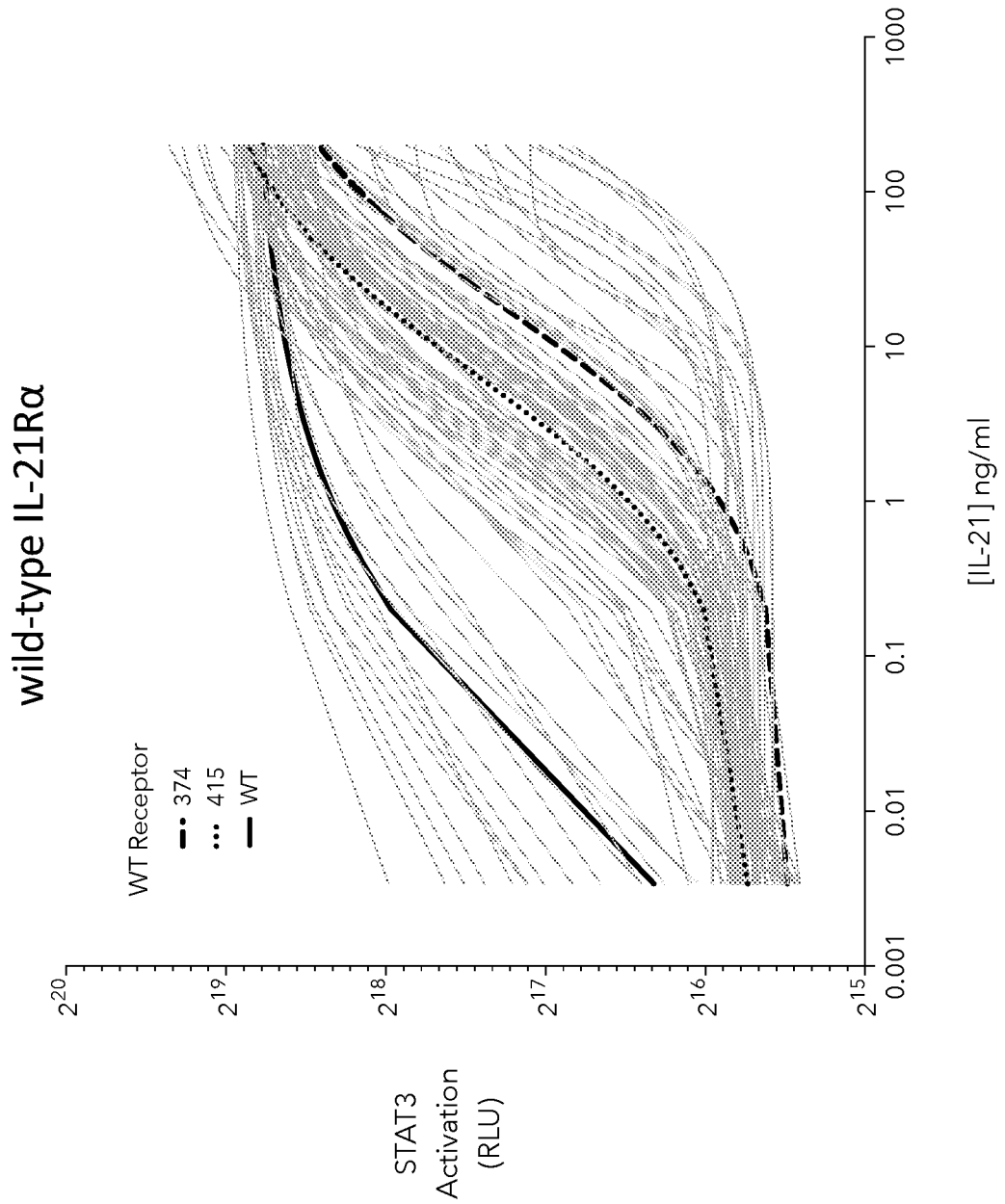
Figure 11B:
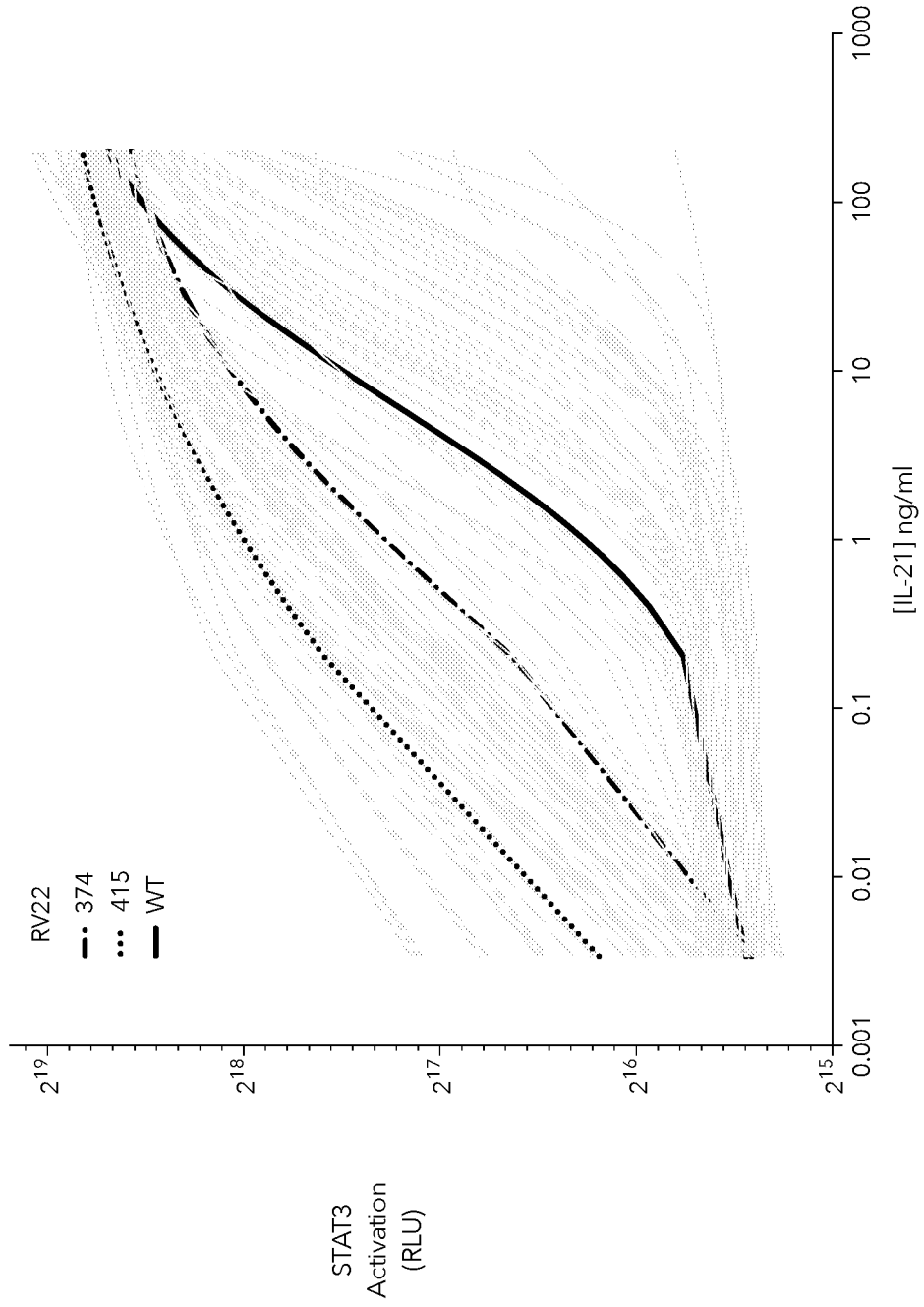
Figure 11C:
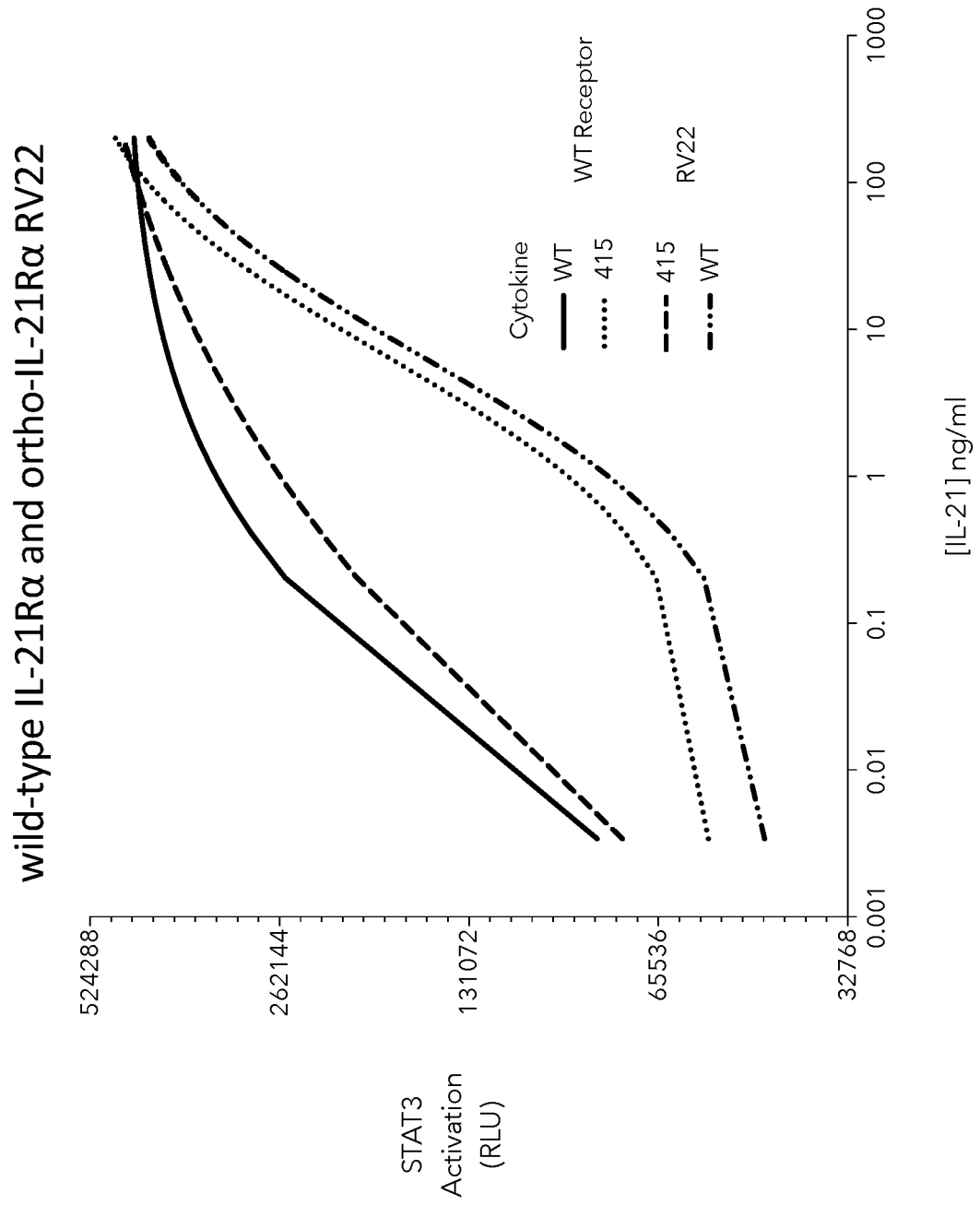

The new series of candidate ortho-IL-21 molecules were screened for their capacity to induce signaling in Ba/F3 cells expressing wild-type IL-21Rα or RV22 as described. Representative data from one such screening experiment are provided in FIGS. 11A-11C. The experimental results depicted in FIGS. 11A-11C derived from the analysis of 96 cytokines, 92 of which were candidate ortho-IL-21 molecules, and four of which were controls including the wild-type form of IL-21. FIG. 11A shows the STAT3 responses elicited in cells expressing wild-type IL-21Rα exposed to the cytokine collection (with the responses to CV374, CV415, and wild-type IL-21 highlighted). Similarly, FIG. 11B shows the STAT3 responses elicited in cells expressing RV22. FIG. 11C shows a comparison of the STAT3 responses elicited by wild-type IL-21 and CV415 on cells expressing either the wild-type IL-21Rα or RV22.

The results in FIGS. 11A-11C show that candidate ortho-IL-21 variant CV415 is active on cells expressing the candidate orthogonal form of IL-21Rα (RV22) but retains low activity on cells expressing wild-type IL-21Rα. As such, CV415 is another candidate for use in an orthogonal IL-21 system.

Example 4: Screening of Candidate Ortho-IL-21 Molecules: Testing for STAT3-Dependent Signaling Responses in Cells Expressing RV6, RV31, or Wild-Type IL-21Rα

The screening strategy described in Example 3 was partially replicated to create a second orthogonal system. Optimally, this second system is orthogonal not just to the native IL-21 system but also to the system described above involving candidate ortho-IL-21Rα molecules comprised of an M70G substitution (including RV13 and RV22). Candidate ortho-IL-21Rα molecules RV6 and RV31 were selected for the creation of such a mutually orthogonal system. RV6 and RV13 RV31 are both comprised of M70I and D73E mutations, but Q33H is also present in RV6.

Figure 12A:
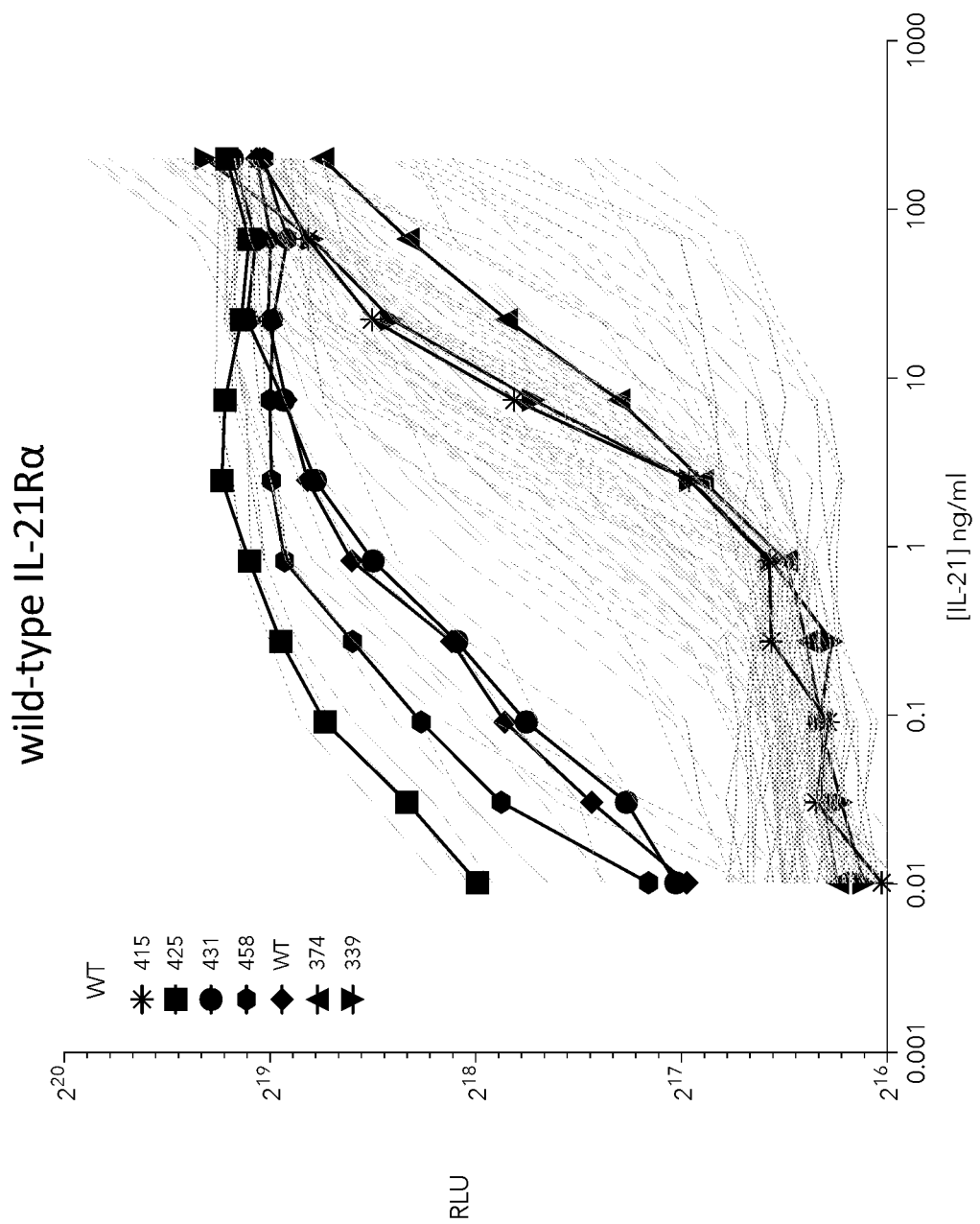
Figure 12B:
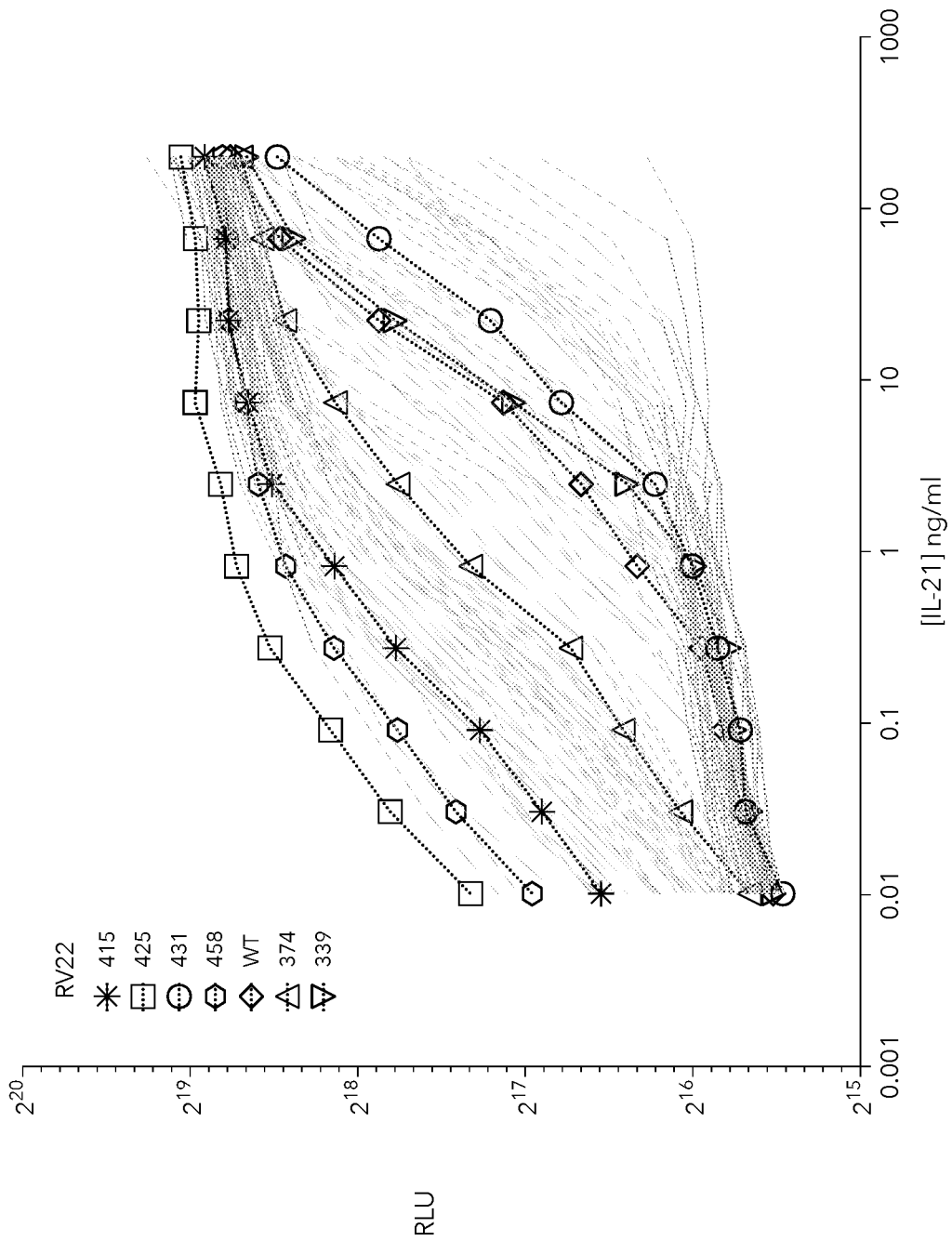
Figure 12C:
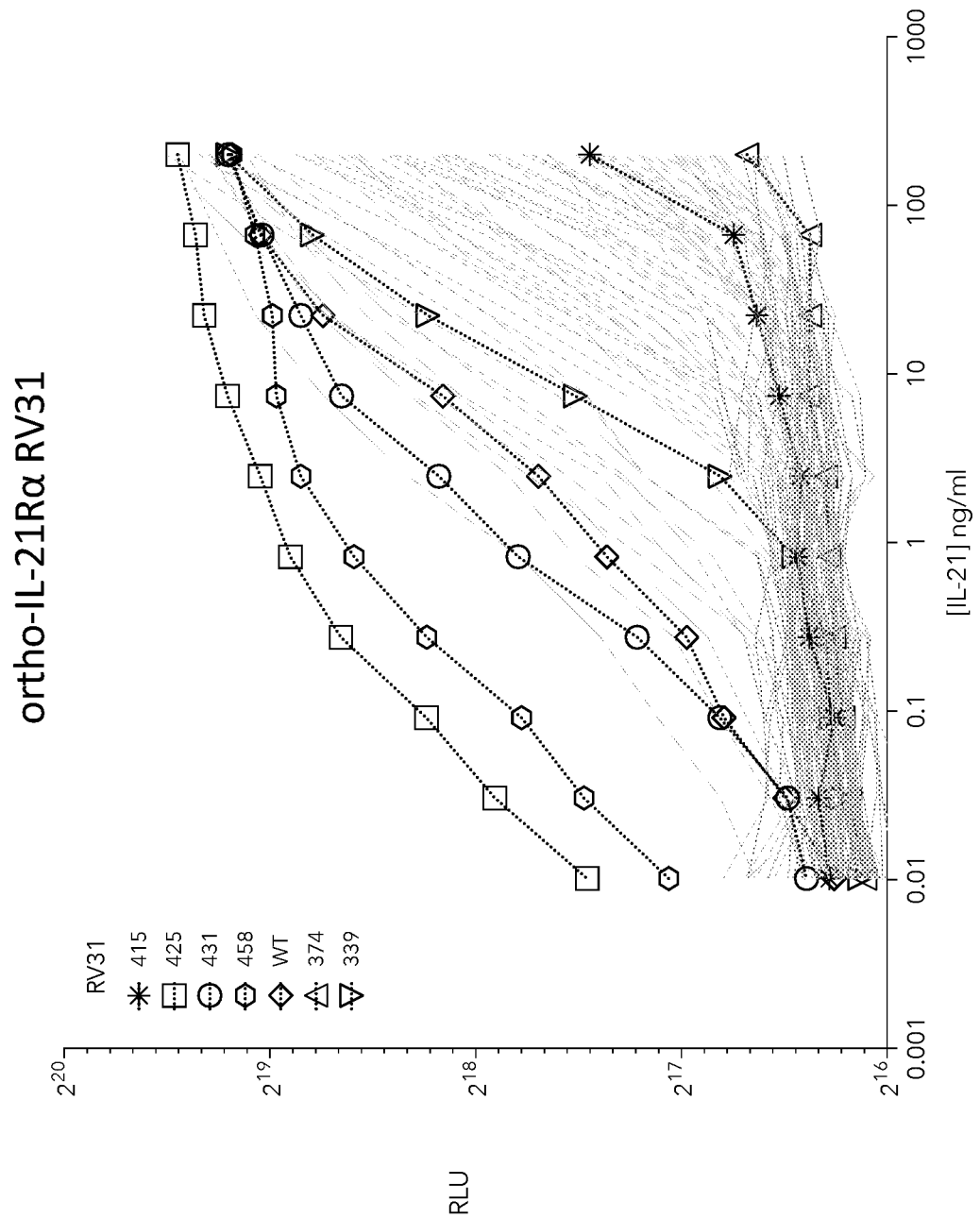

Ba/F3 cells expressing RV6 were tested for responses to the panel of Infolog cytokine variants described above. Data from one such screening experiment are provided in FIG. 8C. Additional cytokine variants were generated based on these data and included in the collection of variants that was the basis of the data shown in FIGS. 11A-11C. The entire collection was then tested for its capacity to induce signaling in BA/F3 cells expressing RV22, RV31, or the wild-type form of IL-21Rα. As shown in FIGS. 12A-C, cytokine variants CV425 and CV458 were notable because they elicited strong responses in all three kinds of cells. By contrast, variant CV431 caused a strong response in cells expressing wild-type IL-21Rα or RV31, but it was comparatively less active against cells expressing RV22. Variant CV339 was weakly active against all three kinds of cells.

Figure 12D:
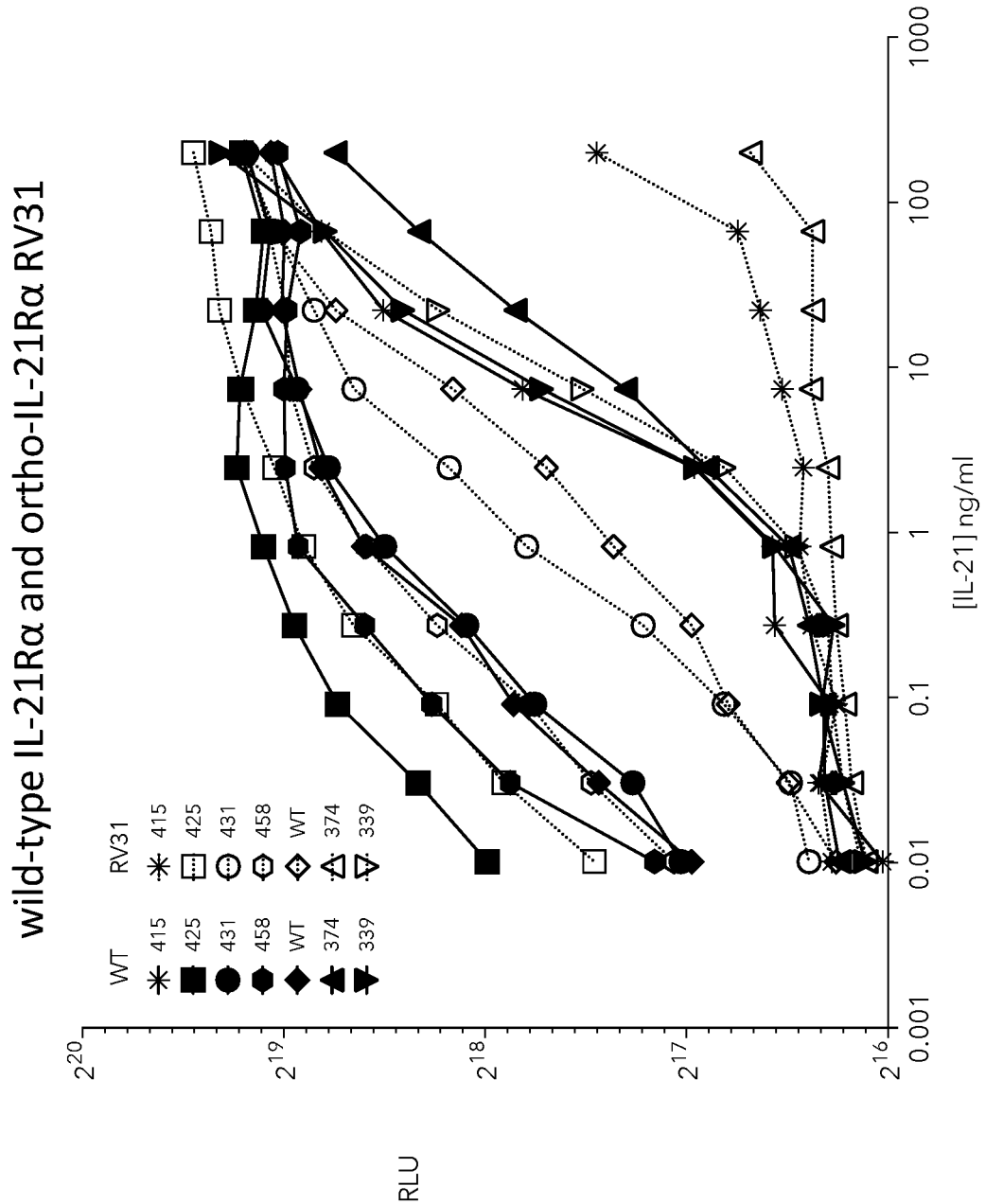

FIG. 12D provides a comparison between responses by selected cytokines (including CV339, CV425, CV431, and CV458) on cells expressing either the wild-type form of IL-21Rα or RV31.

Two additional series of Infolog cytokine variants were generated based on the screening results represented in FIGS. 12A-C and based on relevant aspects of the published IL-21 cytokine-receptor crystal structure. Increased emphasis was placed on using substitutions in cytokine residues that made direct contact with the receptor, and the screens also incorporated receptor variants carrying substitutions in selected relevant contact residues.

Figure 13B:
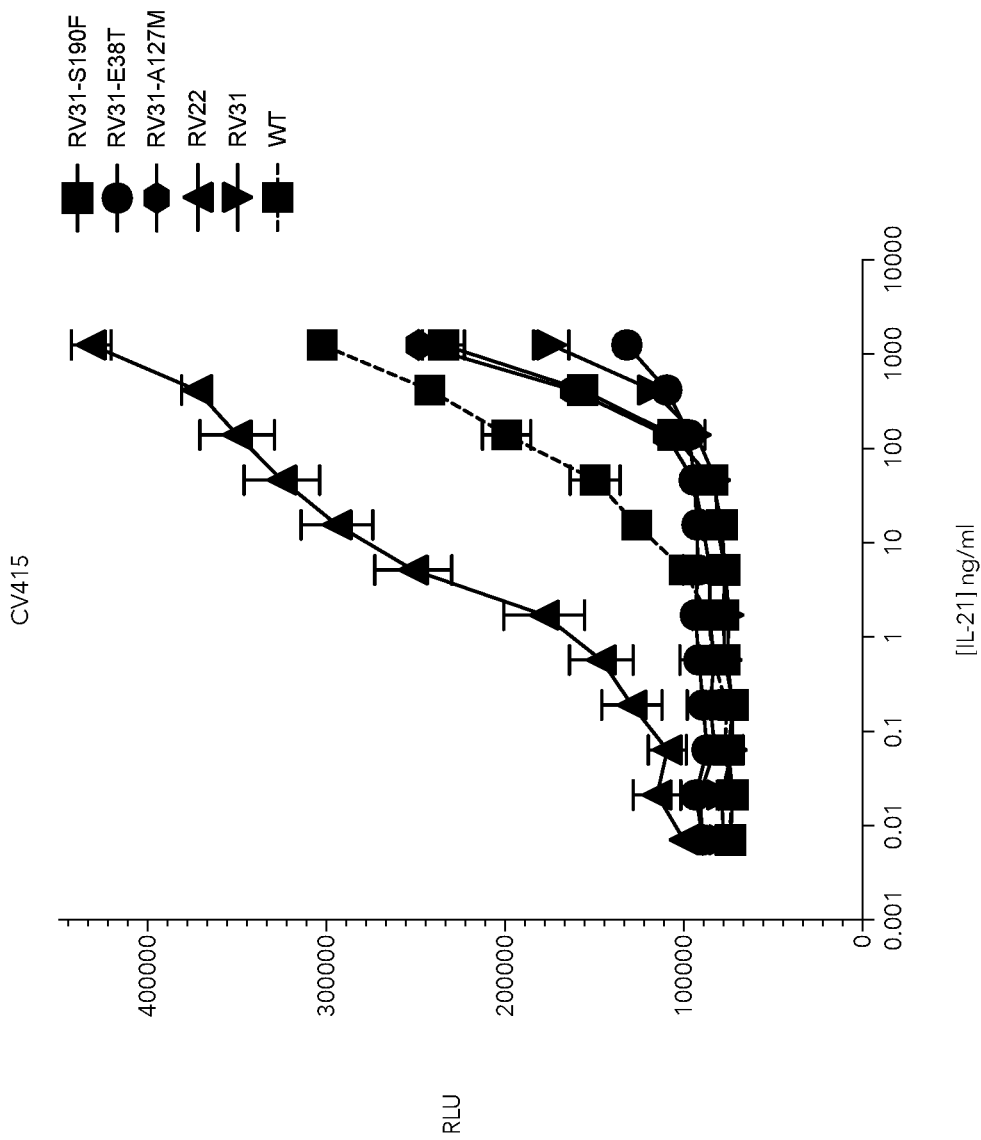
Figure 13C:
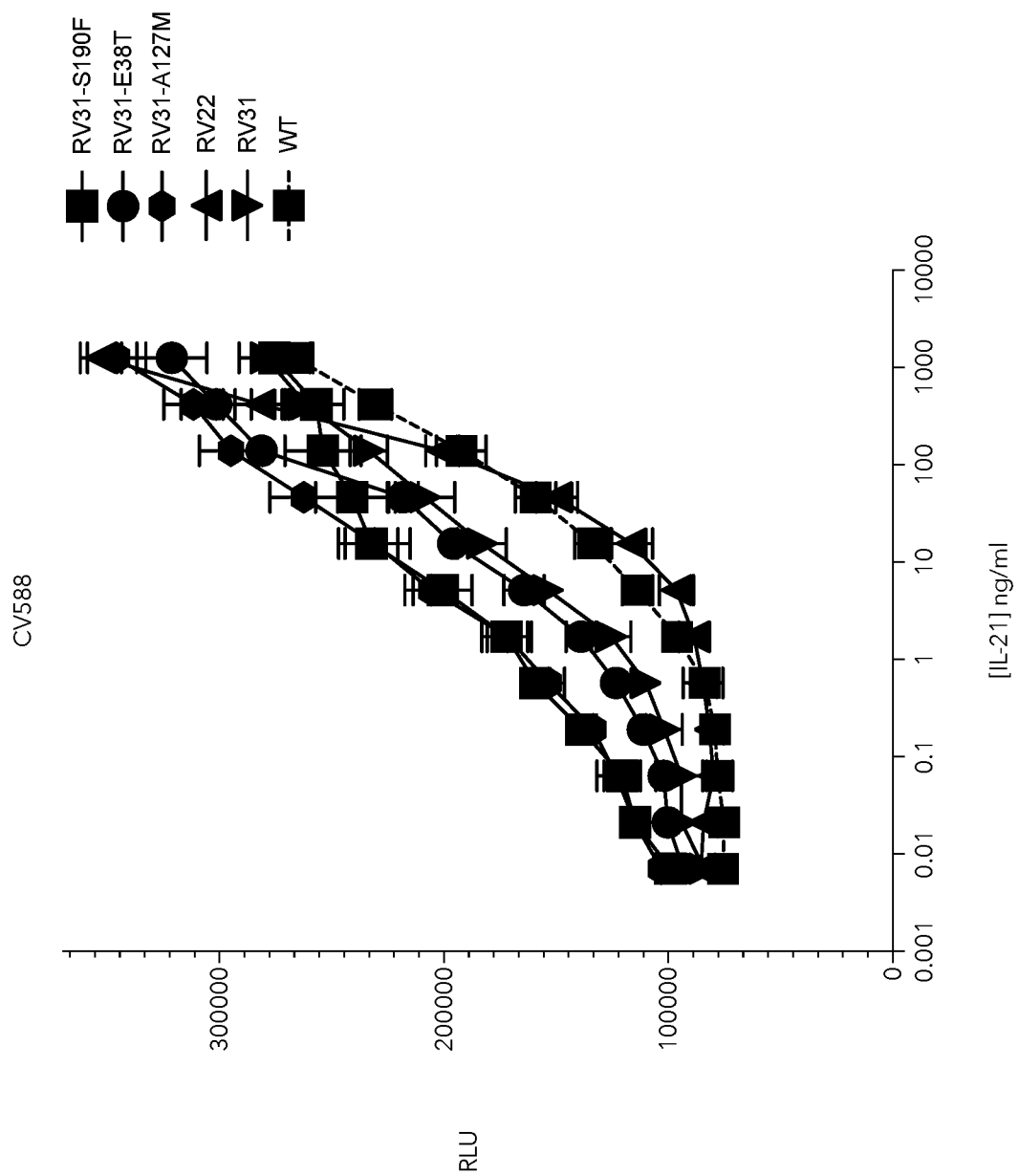
Figure 13D:
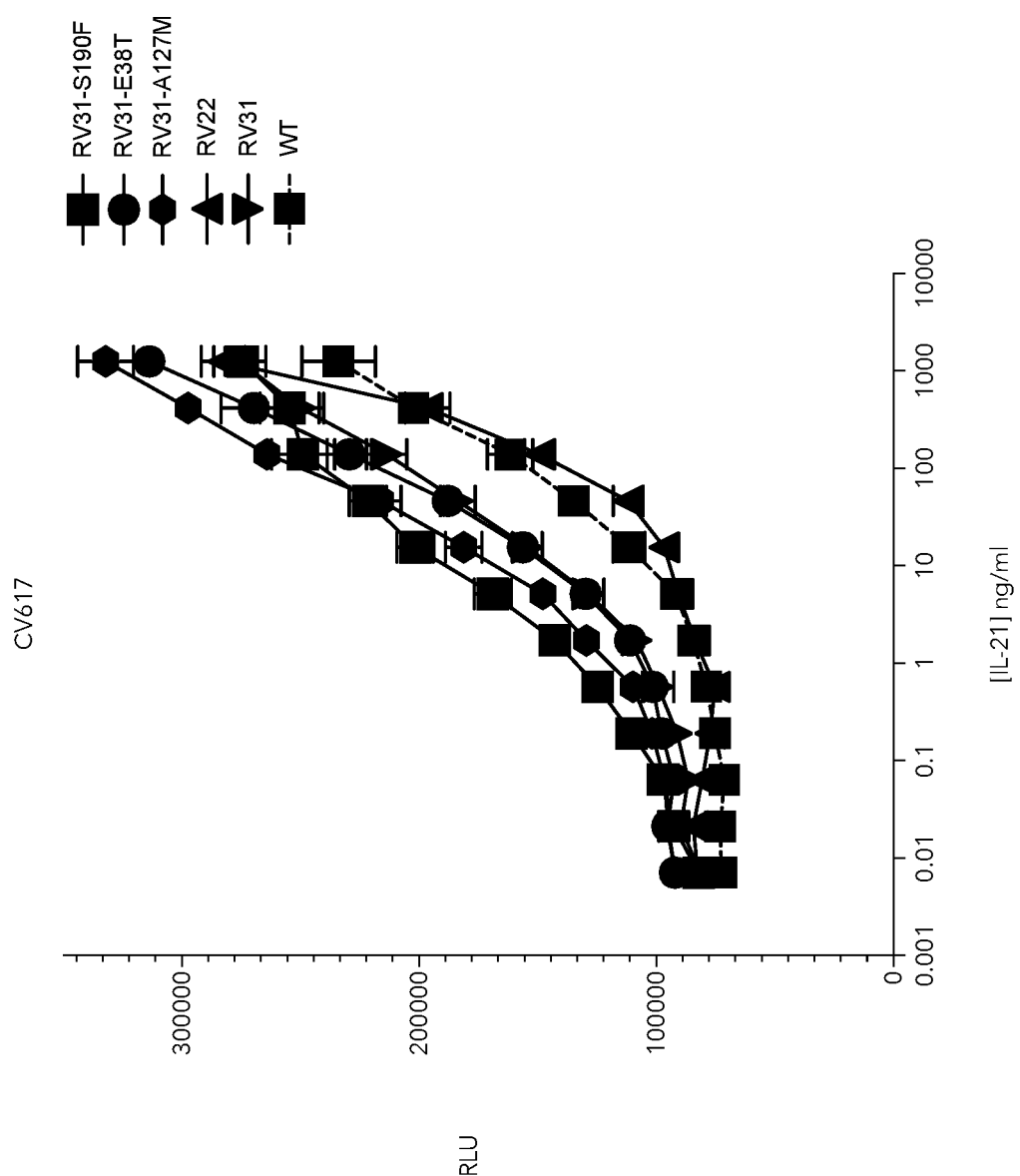
Figure 13E:
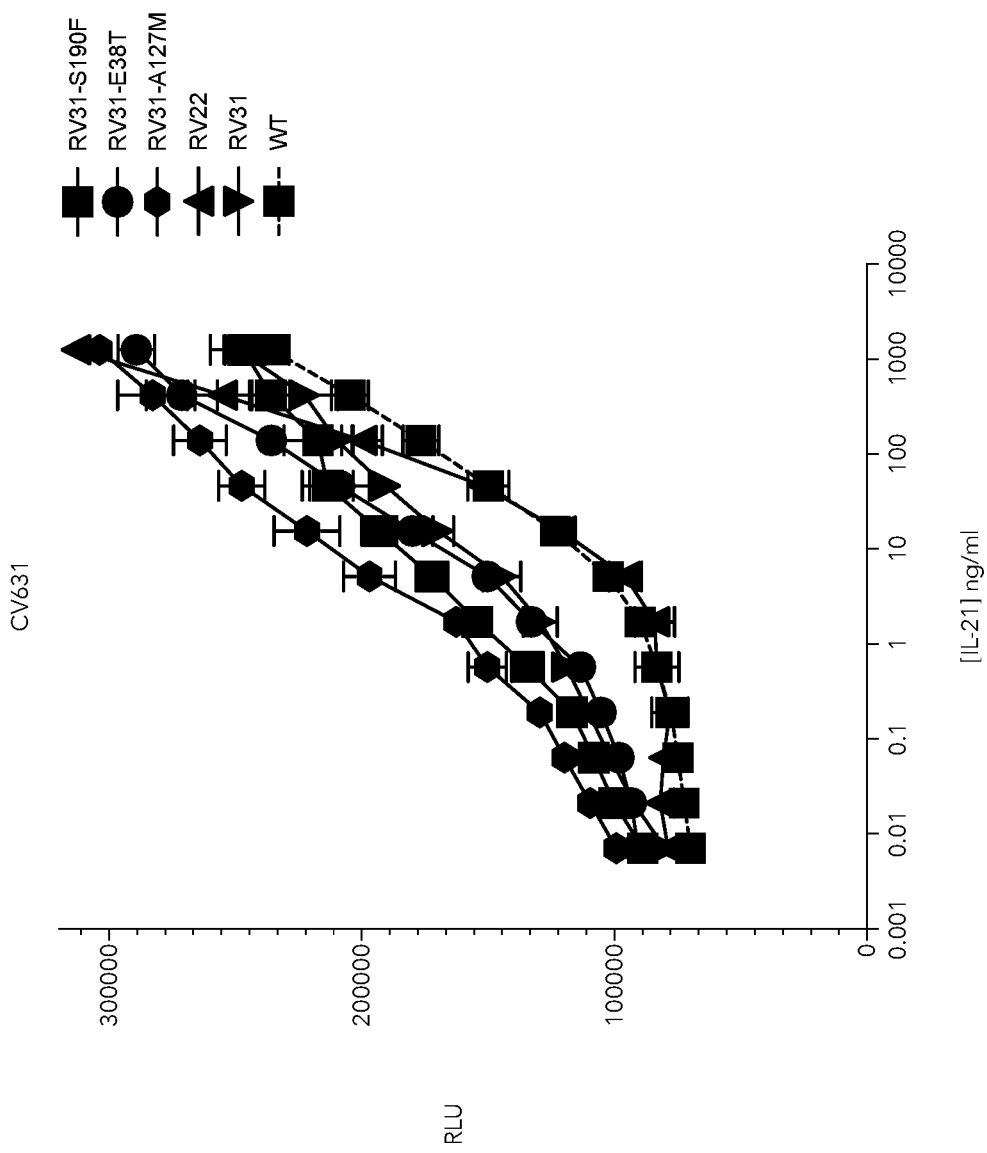

Cytokine variant CV588 showed a preference for RV31 over the wild-type form of IL-21Rα (FIG. 13C). This preference was also apparent for cytokine variants CV617 and CV631 (FIGS. 13D and 13E).

Receptor variants RV31-S190F and RV31-A127M both afforded improved responsiveness to CV588 relative to RV31 (FIG. 13C). A similar improvement in responsiveness was seen with cytokine variants CV617 and CV631 (FIGS. 13D and 13E). These receptor variants conferred impaired responses to wild-type IL-21 (FIG. 13A).

Figure 13F:
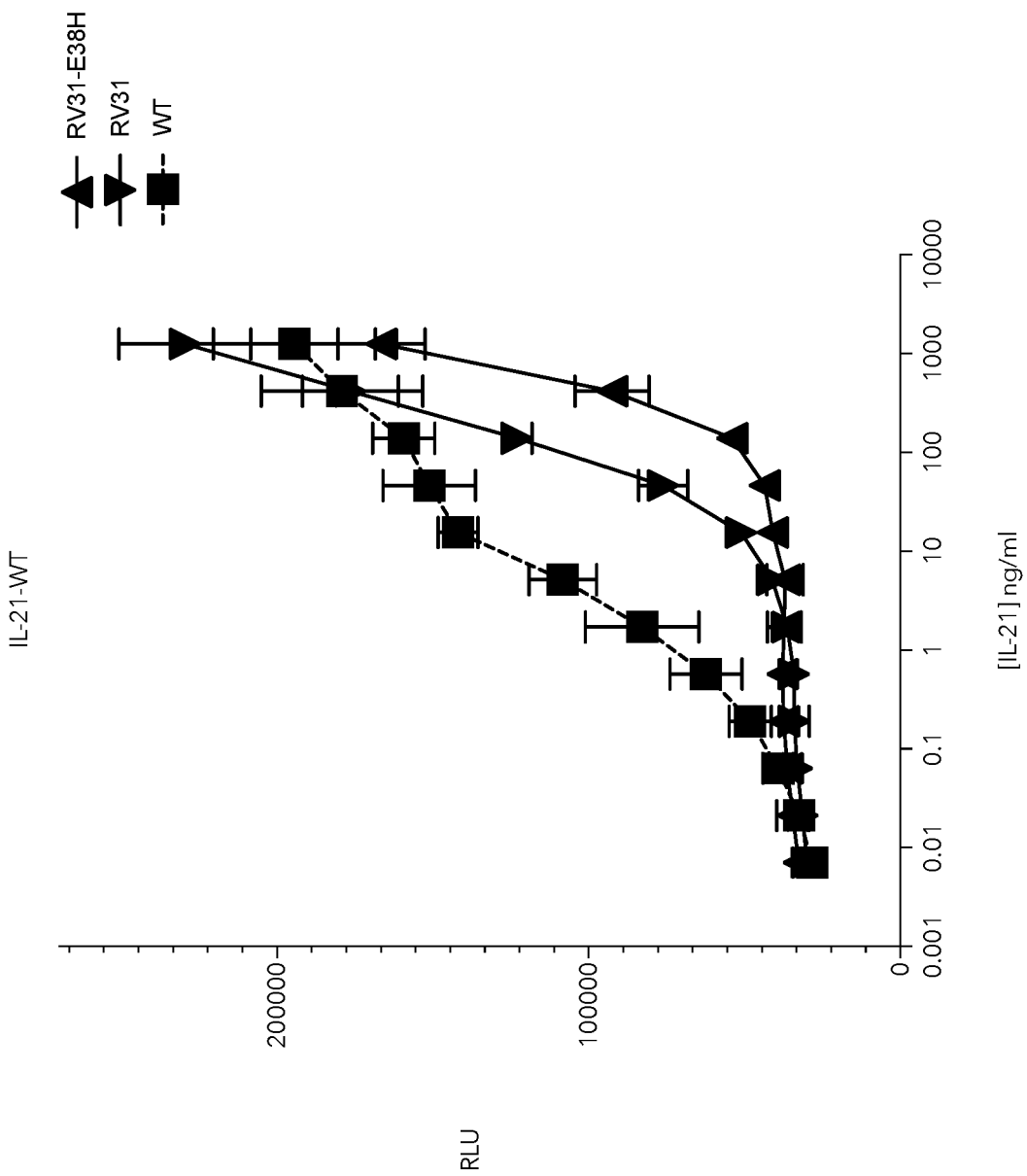

Receptor variants RV31-E38T and RV31-E38H were both associated with decreased responsiveness to wild-type IL-21 relative to the parent RV31 receptor (FIGS. 13A and 13F). Strikingly, both receptor variants retained equivalent responsiveness to CV588, CV617, and CV631 as RV31 (FIGS. 13C-E and FIGS. 13H-I).

Figure 13G:
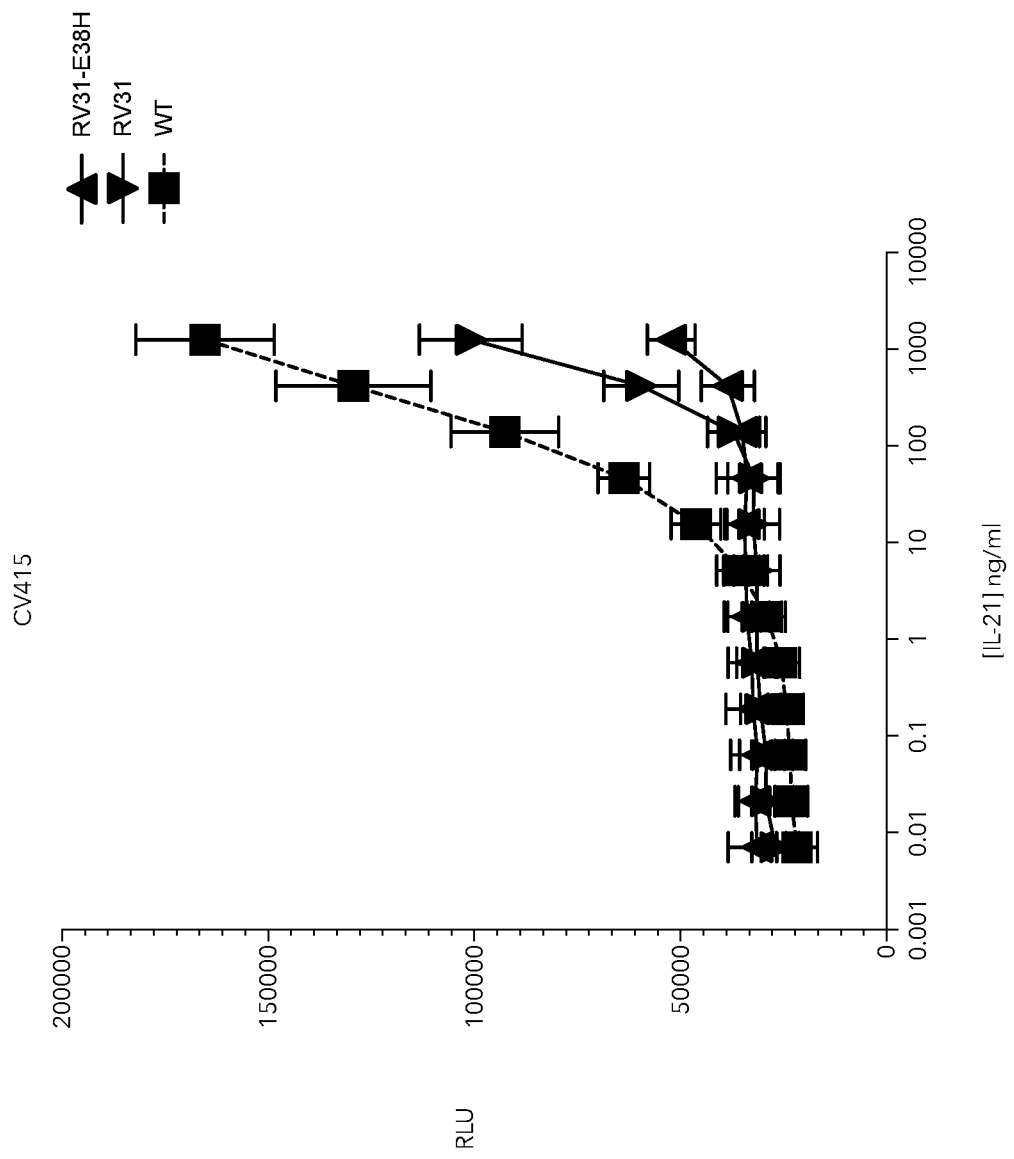
Figure 13H:
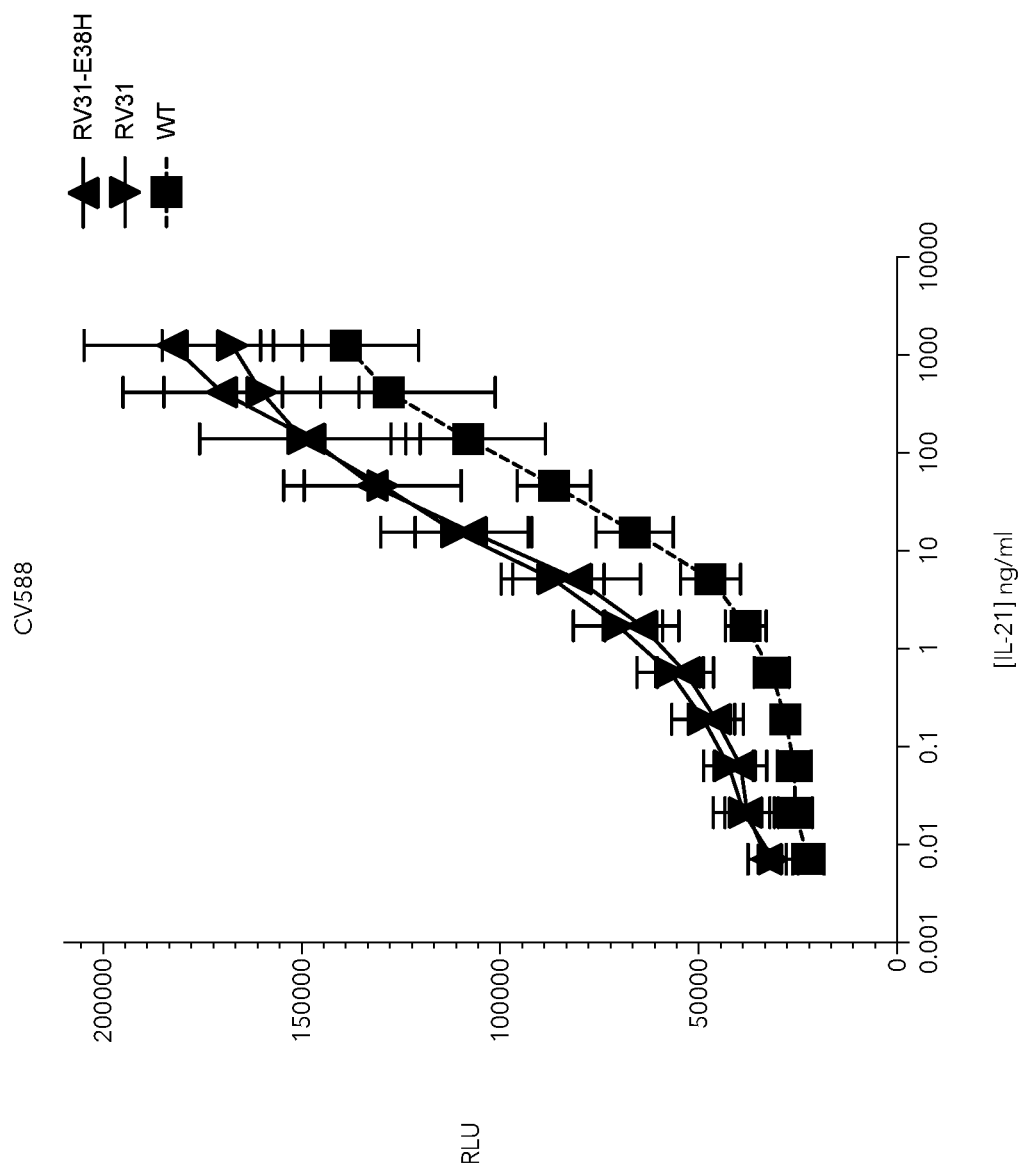
Figure 13I:
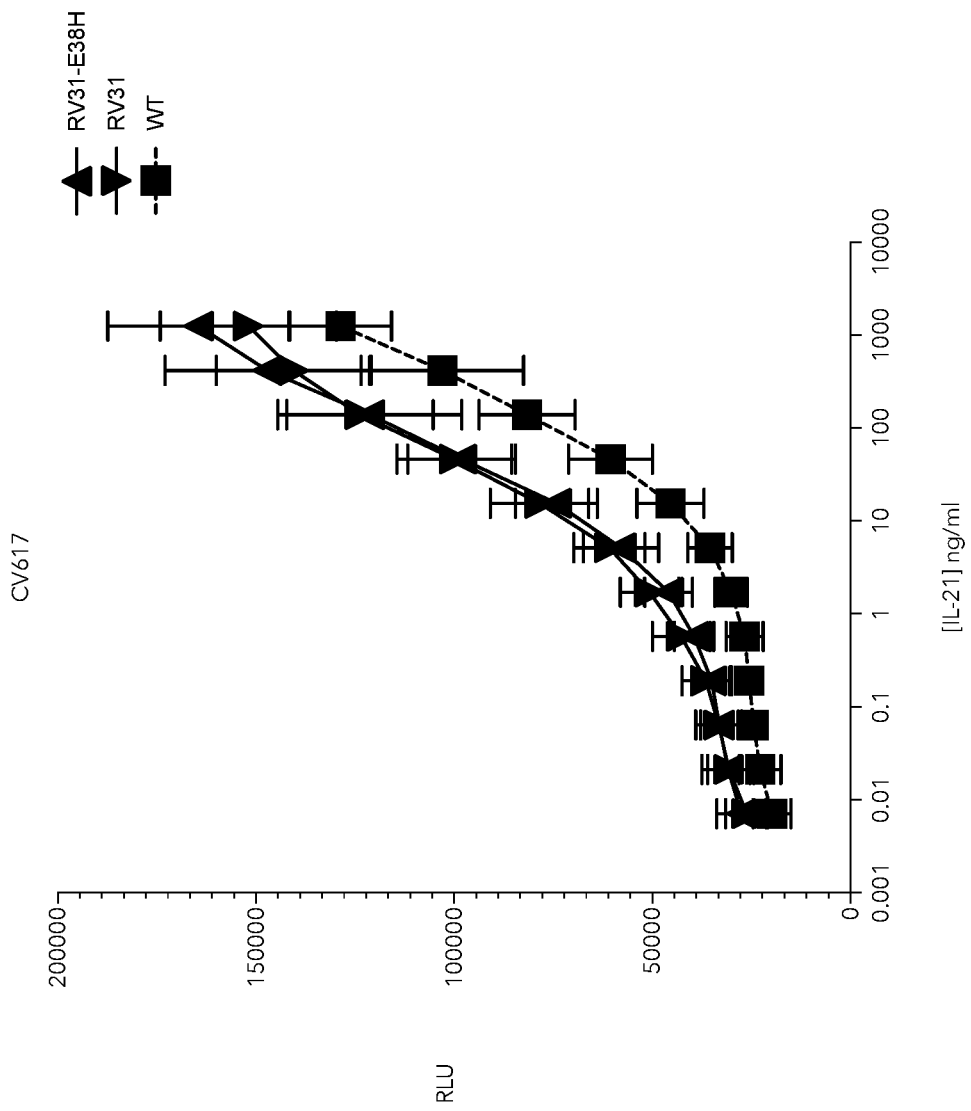
Figure 13J:
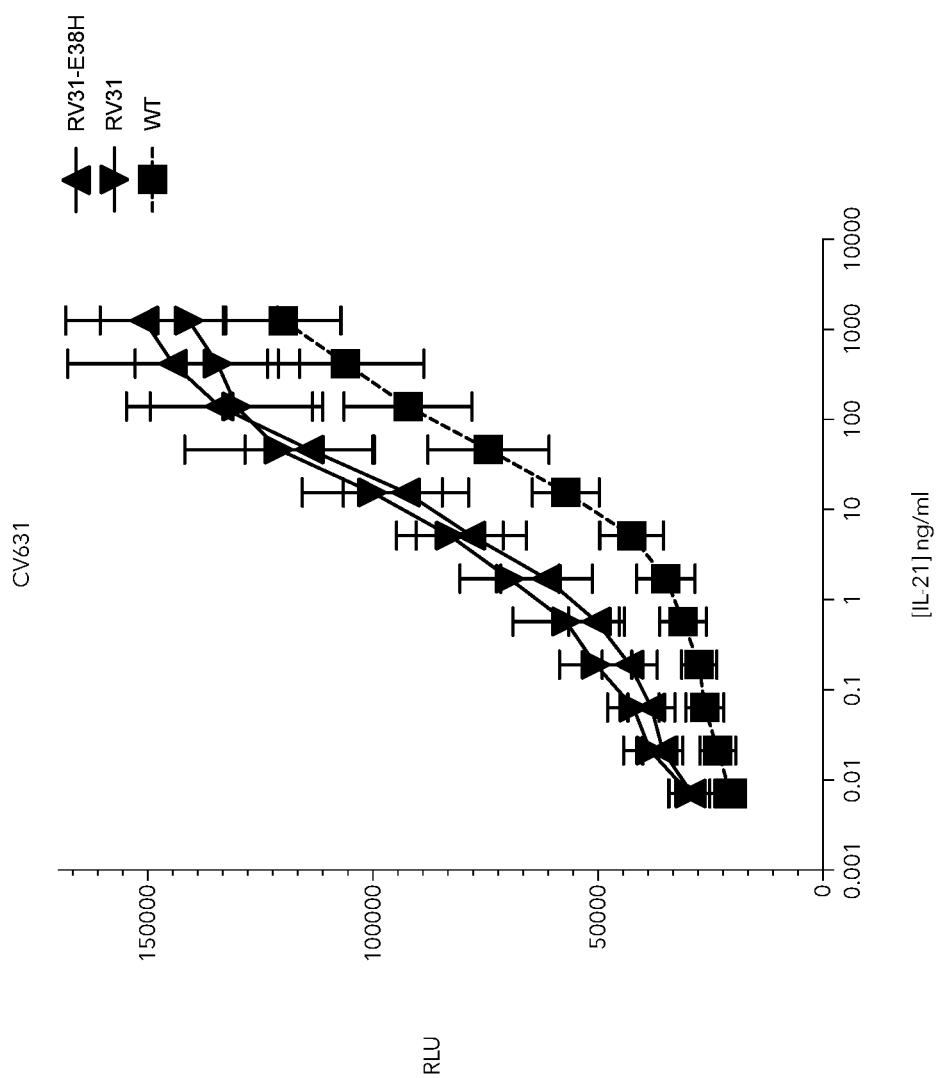

Cytokine variant CV588 showed a similarly weak capacity to stimulate cells expressing RV22 or wild-type IL-21Rα relative to cells expressing RV31 or RV31-S190F (FIG. 13C). By contrast, CV415 showed a much-enhanced preference for cells expressing RV22 than for cells expressing RV31 or RV31-S190F (FIG. 13B). The E38T (FIG. 13B) or E38H (FIG. 13G) substitutions improved this preference by impairing responses to CV415. Although not explicitly shown, the data in FIGS. 13A-13J clearly support other combinations of the amino acid substitutions shown therein, including, for example, RV31-S190F/A127M/E38T, RV31-S190F/A127M/E38H, RV31-S190F/E38T, RV31-S190F/E38T, RV31-A127M/E38T, RV31-A127M/E38H, or RV31-S190F/A127M.

The results just summarized show that substitutions present in CV588, CV617, and CV631 improve the capacity of variant IL-21 to stimulate cells expressing RV31 while decreasing its capacity to stimulate cells expressing the wild-type receptor. This kind of preference is enhanced by the S190F or A127M substitutions in RV31, while the E38T or E38H substitutions can be used to impair the capacity of the receptor to respond to wild-type IL-21. Collectively, these substitutions provide the basis for a cytokine receptor system that functions in an orthogonal fashion to both the native and CV415-RV22 systems.

In most settings, in vitro assays will have only very limited predictive value of the effects of a therapeutic in vivo: many therapeutic targets are expressed in multiple cell types (often having opposing effects on the response in vivo), or the therapeutic effect of a given target is dependent on other auxiliary cells. In such situations, an in vitro model, which by its very nature is simplistic, is not a particularly good proxy for the much more complicated situation in vivo. This is not the case in the instant application: the target receptor is synthetic and will only be expressed in cells specifically engineered to do so. Given the specificity of the orthogonal cytokine-receptor system, this significantly reduces the complexity, giving an in vitro assay a better predictive value.

The complete disclosure of all patents, patent applications, and publications, and electronically available materials cited herein are incorporated by reference. The foregoing detailed description and examples have been given for clarity of understanding only. No unnecessary limitations are to be understood therefrom. While theories may be presented describing possible mechanisms through which the compounds are effective, the inventors are not bound by theories described herein. The invention is not limited to the exact details shown and described, for variations obvious to one skilled in the art will be included within the invention defined by the claims.

What is claimed is:

1. An engineered human IL-21 polypeptide, wherein the amino acid sequence of the polypeptide is derived from SEQ ID NO: 7 and comprises the following amino acid substitutions:
   H6L;
   M10L;
   P78L;
   at position K73;
   R11S or R11T;
   I16V; and
   at position R76,
   wherein the engineered human IL-21 polypeptide exhibits reduced IL-21 activity compared to the wild-type human IL-21 of SEQ ID NO: 7 in a STAT3 activity assay.

2. The engineered human IL-21 polypeptide of claim 1, further comprising an amino acid substitution at S80.

3. The engineered human IL-21 polypeptide of claim 1, further comprising an amino acid substitution at P104.

4. A fusion protein comprising:
   (1) the engineered human IL-21 polypeptide of claim 1; and
   (2) a polypeptide selected from the group consisting of serum albumin, an Fc fragment of IgG, a single-chain Fc antibody fragment, and ABD035.

5. A pharmaceutical composition comprising the engineered human IL-21 polypeptide of claim 1.

6. A polynucleotide comprising a nucleotide sequence encoding for the engineered human IL-21 polypeptide of claim 1.

7. An expression vector comprising the polynucleotide of claim 6.

8. A host cell comprising the expression vector of claim 7.

9. An engineered human IL-21 polypeptide, wherein the amino acid sequence of the polypeptide is derived from SEQ ID NO: 7 and comprises the following amino acid substitutions:
   H6L;
   M10L;
   P78L;
   at position K73;
   R9K; and
   one of: G84E; G84E and P104V; or P104A,
   wherein the engineered human IL-21 polypeptide exhibits reduced IL-21 activity compared to the wild-type human IL-21 of SEQ ID NO: 7 in a STAT3 activity assay.

10. The engineered human IL-21 polypeptide of claim 9 comprising amino acid substitution G84E.

11. The engineered human IL-21 polypeptide of claim 9 comprising amino acid substitution P104A.

12. The engineered human IL-21 polypeptide of claim 9 comprising amino acid substitutions G84E and P104V.

13. The engineered human IL-21 polypeptide of claim 9, wherein the engineered human IL-21 polypeptide comprises the amino acid sequence of SEQ ID NO: 11.

14. A fusion protein comprising:
  (1) the engineered human IL-21 polypeptide of claim 9; and
  (2) a polypeptide selected from the group consisting of serum albumin, an Fc fragment of IgG, a single-chain Fc antibody fragment, and ABD035.

15. A pharmaceutical composition comprising the engineered human IL-21 polypeptide of claim 9.

16. A polynucleotide comprising a nucleotide sequence encoding for the engineered human IL-21 polypeptide of claim 9.

17. An expression vector comprising the polynucleotide of claim 16.

18. A host cell comprising the expression vector of claim 17.

* * * * *

SEQUENCE LISTING

```
Sequence total quantity: 108
SEQ ID NO: 1            moltype = AA  length = 519
FEATURE                 Location/Qualifiers
REGION                  1..519
                        note = Synthetic sequence
source                  1..519
                        mol_type = protein
                        organism = synthetic construct
SEQUENCE: 1
CPDLVCYTDY LQTVICILEM WNLHPSTLTL TWQDQYEELK DEATSCSLHR SAHNATHATY   60
TCHMDVFHFM ADDIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKEGWNPHLL LLLLLVIVFI PAFWSLKTHP  240
LWRLWKKIWA VPSPERFFMP LYKGCSGDFK KWVGAPFTGS SLELGPWSPE VPSTLEVYSC  300
HPPRSPAKRL QLTELQEPAE LVESDGVPKP SFWPTAQNSG GSAYSEERDR PYGLVSIDTV  360
TVLDAEGPCT WPCSCEDDGY PALDLDAGLE PSPGLEDPLL DAGTTVLSCG CVSAGSPGLG  420
GPLGSLLDRL KPPLADGEDW AGGLPWGGRS PGGVSESEAG SPLAGLDMDT FDSGFVGSDC  480
SSPVECDFTS PGDEGPPRSY LRQWVVIPPP LSSPGPQAS                        519

SEQ ID NO: 2            moltype = AA  length = 213
FEATURE                 Location/Qualifiers
REGION                  1..213
                        note = Synthetic sequence
source                  1..213
                        mol_type = protein
                        organism = synthetic construct
SEQUENCE: 2
CPDLVCYTDY LQTVICILEM WNLHPSTLTL TWQDQYEELK DEATSCSLHR SAHNATHATY   60
```

```
TCHMDVFHFM ADDIFSVNIT DQSGNYSQEC GSFLLAESIK PAPPFNVTVT FSGQYNISWR    120
SDYEDPAFYM LKGKLQYELQ YRNRGDPWAV SPRRKLISVD SRSVSLLPLE FRKDSSYELQ    180
VRAGPMPGSS YQGTWSEWSD PVIFQTQSEE LKE                                 213

SEQ ID NO: 3              moltype = AA   length = 213
FEATURE                   Location/Qualifiers
REGION                    1..213
                          note = Synthetic sequence
source                    1..213
                          mol_type = protein
                          organism = synthetic construct
SEQUENCE: 3
CPDLVCYTDY LQTVICILEM WNLHPSTLTL TWQDQYEELK DEATSCSLHR SAHNATHATY     60
TCHMDVFHFG ADDIFSVNIT DQSGNYSQEC GSFLLAESIK PAPPFNVTVT FSGQYNISWR    120
SDYEDPAFFM LKGKLQYELQ YRNRGDPWAV SPRRKLISVD SRSVSLLPLE FRKDSSYELQ    180
VRAGPMPGSS YQGTWSEWSD PVIFQTQSEE LKE                                 213

SEQ ID NO: 4              moltype = AA   length = 213
FEATURE                   Location/Qualifiers
REGION                    1..213
                          note = Synthetic sequence
source                    1..213
                          mol_type = protein
                          organism = synthetic construct
SEQUENCE: 4
CPDLVCYTDY LQTVICILEM WNLHPSTLTL TWQDQYEELK DEATSCSLHR SAHNATHATY     60
TCHMDVFHFG ADDIFSVNIT DQSGNYSQEC GSFLLAESIK PAPPFNVTVT FSGQYNISWR    120
SDYEDPAFYM LKGKLQYELQ YRNRGDPWAV SPRRKLISVD SRSVSLLPLE FRKDSSYELQ    180
VRAGPMPGSS YQGTWSEWSD PVIFQTQSEE LKE                                 213

SEQ ID NO: 5              moltype = AA   length = 213
FEATURE                   Location/Qualifiers
REGION                    1..213
                          note = Synthetic sequence
source                    1..213
                          mol_type = protein
                          organism = synthetic construct
SEQUENCE: 5
CPDLVCYTDY LQTVICILEM WNLHPSTLTL TWHDQYEELK DEATSCSLHR SAHNATHATY     60
TCHMDVFHFI ADEIFSVNIT DQSGNYSQEC GSFLLAESIK PAPPFNVTVT FSGQYNISWR    120
SDYEDPAFYM LKGKLQYELQ YRNRGDPWAV SPRRKLISVD SRSVSLLPLE FRKDSSYELQ    180
VRAGPMPGSS YQGTWSEWSD PVIFQTQSEE LKE                                 213

SEQ ID NO: 6              moltype = AA   length = 213
FEATURE                   Location/Qualifiers
REGION                    1..213
                          note = Synthetic sequence
source                    1..213
                          mol_type = protein
                          organism = synthetic construct
SEQUENCE: 6
CPDLVCYTDY LQTVICILEM WNLHPSTLTL TWQDQYEELK DEATSCSLHR SAHNATHATY     60
TCHMDVFHFI ADEIFSVNIT DQSGNYSQEC GSFLLAESIK PAPPFNVTVT FSGQYNISWR    120
SDYEDPAFYM LKGKLQYELQ YRNRGDPWAV SPRRKLISVD SRSVSLLPLE FRKDSSYELQ    180
VRAGPMPGSS YQGTWSEWSD PVIFQTQSEE LKE                                 213

SEQ ID NO: 7              moltype = AA   length = 133
FEATURE                   Location/Qualifiers
REGION                    1..133
                          note = Synthetic sequence
source                    1..133
                          mol_type = protein
                          organism = synthetic construct
SEQUENCE: 7
QGQDRHMIRM RQLIDIVDQL KNYVNDLVPE FLPAPEDVET NCEWSAFSCF QKAQLKSANT     60
GNNERIINVS IKKLKRKPPS TNAGRRQKHR LTCPSCDSYE KKPPKEFLER FKSLLQKMIH    120
QHLSSRTHGS EDS                                                       133

SEQ ID NO: 8              moltype = AA   length = 189
FEATURE                   Location/Qualifiers
REGION                    1..189
                          note = Synthetic sequence
source                    1..189
                          mol_type = protein
                          organism = synthetic construct
SEQUENCE: 8
APWSHPQFEK GGGSGGGSGG SSAWSHPQFE KEQKLISEED LGGGGSGGGG SGGGGSQGQD     60
RLMIKLRQLI DIVDQLKNYV NDLVPEFLPA PEDVETNCEW SAFSCFQKAQ LKSANTGNNE    120
RIINVSIKVL KRKLPSTNAE RRQKHRLTCP SCDSYEKKPP KEFLERFKSL LQKMIHQHLS    180
```

```
SRTHGSEDS                                                                       189

SEQ ID NO: 9               moltype = AA   length = 189
FEATURE                    Location/Qualifiers
REGION                     1..189
                           note = Synthetic sequence
source                     1..189
                           mol_type = protein
                           organism = synthetic construct
SEQUENCE: 9
APWSHPQFEK GGGSGGGSGG SSAWSHPQFE KEQKLISEED LGGGGSGGGG SGGGGSQGQD    60
RLMIKLRQLI DIVDQLKNYV NDLVPEFLPA PEDVETNCEW SAFSCFQKAQ LKSANTGNNE   120
RIINVSIKIL KRKLPSTNAG RRQKHRLTCP SCDSYEKKPA KEFLERFKSL LQKMIHQHLS   180
SRTHGSEDS                                                           189

SEQ ID NO: 10              moltype = AA   length = 189
FEATURE                    Location/Qualifiers
REGION                     1..189
                           note = Synthetic sequence
source                     1..189
                           mol_type = protein
                           organism = synthetic construct
SEQUENCE: 10
APWSHPQFEK GGGSGGGSGG SSAWSHPQFE KEQKLISEED LGGGGSGGGG SGGGGSQGQD    60
RLMIKLRQLI DIVDQLKNYV NDLVPEFLPA PEDVETNCEW SAFSCFQKAQ LKSANTGNNE   120
RIINVSIKIL KRKLPSTNAG RRQKHRLTCP SCDSYEKKPP KEFLERFKSL LQKMIHQHLS   180
SRTHGSEDS                                                           189

SEQ ID NO: 11              moltype = AA   length = 189
FEATURE                    Location/Qualifiers
REGION                     1..189
                           note = Synthetic sequence
source                     1..189
                           mol_type = protein
                           organism = synthetic construct
SEQUENCE: 11
APWSHPQFEK GGGSGGGSGG SSAWSHPQFE KEQKLISEED LGGGGSGGGG SGGGGSQGQD    60
RLMIKLRQLI DIVDQLKNYV NDLVPEFLPA PEDVETNCEW SAFSCFQKAQ LKSANTGNNE   120
RIINVSIKIL KRKLPSTNAE RRQKHRLTCP SCDSYEKKPV KEFLERFKSL LQKMIHQHLS   180
SRTHGSEDS                                                           189

SEQ ID NO: 12              moltype = AA   length = 189
FEATURE                    Location/Qualifiers
REGION                     1..189
                           note = Synthetic sequence
source                     1..189
                           mol_type = protein
                           organism = synthetic construct
SEQUENCE: 12
APWSHPQFEK GGGSGGGSGG SSAWSHPQFE KEQKLISEED LGGGGSGGGG SGGGGSQGQD    60
RLMIRLRQLI DIVDQLKNYV NDLVPEFLPA PEDVETNCEW SAFSCFQKAQ LKSANTGNNE   120
RIINVSIKVL KKKPPSTNAG RRQKHRLTCP SCDSYEKKPA KEFLERFKSL LQKMIHQHLS   180
SRTHGSEDS                                                           189

SEQ ID NO: 13              moltype = AA   length = 189
FEATURE                    Location/Qualifiers
REGION                     1..189
                           note = Synthetic sequence
source                     1..189
                           mol_type = protein
                           organism = synthetic construct
SEQUENCE: 13
APWSHPQFEK GGGSGGGSGG SSAWSHPQFE KEQKLISEED LGGGGSGGGG SGGGGSQGQD    60
RLMIRLRQLI DIVDQLKNYV NDLVPEFLPA PEDVETNCEW SAFSCFQKAQ LKSANTGNNE   120
RIINVSIKLL KRKLPSTNAG RRQKHRLTCP SCDSYEKKPP KEFLERFKSL LQKMIHQHLS   180
SRTHGSEDS                                                           189

SEQ ID NO: 14              moltype = AA   length = 189
FEATURE                    Location/Qualifiers
REGION                     1..189
                           note = Synthetic sequence
source                     1..189
                           mol_type = protein
                           organism = synthetic construct
SEQUENCE: 14
APWSHPQFEK GGGSGGGSGG SSAWSHPQFE KEQKLISEED LGGGGSGGGG SGGGGSQGQD    60
RLMIRLRQLI DIVDQLKNYV NDLVPEFLPA PEDVETNCEW SAFSCFQKAQ LKSANTGNNE   120
RIINVSIKML KHKLPSTNAE RRQKHRLTCP SCDSYEKKPP KEFLERFKSL LQKMIHQHLS   180
SRTHGSEDS                                                           189
```

```
SEQ ID NO: 15            moltype = AA   length = 189
FEATURE                  Location/Qualifiers
REGION                   1..189
                         note = Synthetic sequence
source                   1..189
                         mol_type = protein
                         organism = synthetic construct
SEQUENCE: 15
APWSHPQFEK GGGSGGGSGG SSAWSHPQFE KEQKLISEED LGGGGSGGGG SGGGGSQGQD    60
RLMIRLRQLI DIVDQLKNYV NDLVPEFLPA PEDVETNCEW SAFSCFQKAQ LKSANTGNNE   120
RIINVSIKLL KRKLPPTNAG RRQKHRLTCP SCDSYEKKPA KEFLERFKSL LQKMIHQHLS   180
SRTHGSEDS                                                           189

SEQ ID NO: 16            moltype = AA   length = 199
FEATURE                  Location/Qualifiers
REGION                   1..199
                         note = Synthetic sequence
source                   1..199
                         mol_type = protein
                         organism = synthetic construct
SEQUENCE: 16
APWSHPQFEK GGGSGGGSGG SSAWSHPQFE KGGGGSGGGG SGGGGSQGQD RHMIKMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGSE QKLISEEDL                                                 199

SEQ ID NO: 17            moltype = AA   length = 199
FEATURE                  Location/Qualifiers
REGION                   1..199
                         note = Synthetic sequence
source                   1..199
                         mol_type = protein
                         organism = synthetic construct
SEQUENCE: 17
APWSHPQFEK GGGSGGGSGG SSAWSHPQFE KGGGGSGGGG SGGGGSQGQD RHMIRMRQLI    60
DIVDQLKNYV NDLVPEFLPA PEDVETNCEW SAFSCFQKAQ LKSANTGNNE RIINVSIKVL   120
KRKPPSTNAG RRQKHRLTCP SCDSYEKKPP KEFLERFKSL LQKMIHQHLS SRTHGSEDSG   180
GGGSGGGSE QKLISEEDL                                                 199

SEQ ID NO: 18            moltype = AA   length = 199
FEATURE                  Location/Qualifiers
REGION                   1..199
                         note = Synthetic sequence
source                   1..199
                         mol_type = protein
                         organism = synthetic construct
SEQUENCE: 18
APWSHPQFEK GGGSGGGSGG SSAWSHPQFE KGGGGSGGGG SGGGGSQGQD QHMIRMRQLI    60
DIVDQLKNYV NDLVPEFLPA PEDVETNCEW SAFSCFQKAQ LKSANTGNNE RIINVSIKKL   120
KAKPPSTNAG RRQKHRLTCP SCDSYEKKPP KEFLERFKSL LQKMIHQHLS SRTHGSEDSG   180
GGGSGGGSE QKLISEEDL                                                 199

SEQ ID NO: 19            moltype = AA   length = 199
FEATURE                  Location/Qualifiers
REGION                   1..199
                         note = Synthetic sequence
source                   1..199
                         mol_type = protein
                         organism = synthetic construct
SEQUENCE: 19
APWSHPQFEK GGGSGGGSGG SSAWSHPQFE KGGGGSGGGG SGGGGSQGQD RLMIRLRQLI    60
DIVDQLKNYV NDLVPEFLPA PEDVETNCEW SAFSCFQKAQ LKSANTGNNE RIINVSIKVL   120
KRKLPSTNAG RRQKHRLTCP SCDSYEKKPA KEFLERFKSL LQKMIHQHLS SRTHGSEDSG   180
GGGSGGGSE QKLISEEDL                                                 199

SEQ ID NO: 20            moltype = AA   length = 538
FEATURE                  Location/Qualifiers
REGION                   1..538
                         note = Synthetic sequence
source                   1..538
                         mol_type = protein
                         organism = synthetic construct
SEQUENCE: 20
MPRGWAAPLL LLLLQGGWGC PDLVCYTDYL QTVICILEMW NLHPSTLTLT WQDQYEELKD    60
EATSCSLHRS AHNATHATYT CHMDVFHFMA DDIFSVNITD QSGNYSQECG SPLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
```

```
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS     538

SEQ ID NO: 21              moltype = AA  length = 162
FEATURE                    Location/Qualifiers
REGION                     1..162
                           note = Synthetic sequence
source                     1..162
                           mol_type = protein
                           organism = synthetic construct
SEQUENCE: 21
MRSSPGNMER IVICLMVIFL GTLVHKSSSQ GQDRHMIRMR QLIDIVDQLK NYVNDLVPEF    60
LPAPEDVETN CEWSAFSCFQ KAQLKSANTG NNERIINVSI KKLKRKPPST NAGRRQKHRL   120
TCPSCDSYEK KPPKEFLERF KSLLQKMIHQ HLSSRTHGSE DS                      162

SEQ ID NO: 22              moltype = DNA  length = 1617
FEATURE                    Location/Qualifiers
misc_feature               1..1617
                           note = Synthetic sequence
source                     1..1617
                           mol_type = other DNA
                           organism = synthetic construct
SEQUENCE: 22
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcatgacc agtacgaaga actgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccacctt tcaacgtcac cgtgactttt agcggacagt acaacatctc tggcggagc   420
gactacgagg atccggcctt ctacatgctg aagggaaagc tgcagtacga actgcagtat   480
aggaatcgcg gggacccgtg ggctgtctcc cctcggcgga agctgatttc cgtggattcg   540
agatccgtgt ccctgctccc actgaattc agaaaagatt cgtcctacga actccagtc   600
cgcgcaggac ccatgcctgg aagctctac cagggaacct ggtccgagtg gtcggatccc   660
gtgatcttcc aaaacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttttaagaa tgggtcggag cccccttcac cggatcgagc   900
ctcgagctgg gccctggtc cccgaagtg ccttcgaccc tggaggtgta cagctgccac   960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
agcgcatact ccgaagagag ggacaggcc tacggactcg tgtccatcga taccgtgacc  1140
gtgctgacg ctgagggacc gtgcacttgg ccgtgttcgt gcgaggacga cggatacccg  1200
gcgctggatc tggatgctgg tctggagccg tccccggac tggaagatcc gctgctggac  1260
gccggggacca ccgtgctgtc gtgcggatgc gtgtccgccg ggtcctgg tctgggcggg  1320
cctcttggtt ccctcctgga ccggcttaag cccccgctgg ctgacggaga ggactgggc  1380
ggggactgc cttgggcgg acgctcacct ggggagtgt cggaatcga agccggctcc  1440
cctttggccg gactggacat ggacacattc gatagcggtt tcgtgggatc cgactgttct  1500
agccccgtgg agtgcgattt cacctccccg ggcgacgagg gtccgccgag atcctacttg  1560
cgccaatggg tggtcattcc ccctccactg tcctcccccg ggcacaggc gtcttga     1617

SEQ ID NO: 23              moltype = DNA  length = 1617
FEATURE                    Location/Qualifiers
misc_feature               1..1617
                           note = Synthetic sequence
source                     1..1617
                           mol_type = other DNA
                           organism = synthetic construct
SEQUENCE: 23
atgccgcgtg gctgggccgc ccccttgctc ctgctgctgc tccagggagg ctggggctgc    60
cctgacctcg tgtgctacac tgactacctc caaaccgtga tctgcatcct tgagatgtgg   120
aacttgcacc cttcgactct gactctgacg tggcaggaca gtacgaaga actgaaggat   180
gaagccacct cctgttccct gcaccggtcc gcgcataacg ccacccacgc cacctacact   240
tgccacatgg acgtgttcca cttcggcgcc gatgacatct ctccgtgaa cataccgac   300
cagtccggga actacagcca ggagtgtggt tcatttcttc tggcggagtc catcaagccc   360
gccccaccgt tcaacgtgac cgtgactttc tcggggcagt acaacatcag ctggcgcatc   420
gactacgaag atccggcatt ctttatgctc aagggcaaac tgcagtacga acttcagtac   480
cgcaaccggg gcgatccctg ggccgtcagc cctcggcgga agctgattag cgtcgactcc   540
cggtccgtgt cactgctccc gctgaattc cggaaggata gctcgtatga actccaagtc   600
cgcgccggac ctatgccggg atcaagctac cagggaacct ggtcggaatg gtccgaccct   660
gtgattttcc aaactcagtc cgaagaactc aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttttaagaa tgggtcggag cccccttcac cggatcgagc   900
ctcgagctgg gccctggtc cccgaagtg ccttcgaccc tggaggtgta cagctgccac   960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
```

```
agcgcatact ccgaagagag ggacaggccg tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtcccctgg tctgggcggg  1320
cctcttggtt ccctcctgga ccggcttaag ccccgctgg ctgacggaga ggactgggcc  1380
gggggactgc cttggggcgg acgctcacct gggggagtgt cggaatccga agccggctcc  1440
cctttggccg gactggacat ggacacattc gatagcggtt tcgtgggatc cgactgttct  1500
agccccgtgg agtgcgattt cacctccccg ggcgacgagg gtccgccgag atcctacttg  1560
cgccaatggg tggtcattcc ccctccactg tcctccccgg ggccacaggc gtcttga      1617

SEQ ID NO: 24           moltype = DNA  length = 1617
FEATURE                 Location/Qualifiers
misc_feature            1..1617
                        note = Synthetic sequence
source                  1..1617
                        mol_type = other DNA
                        organism = synthetic construct
SEQUENCE: 24
atgccgcgtg gctgggccgc ccccttgctc ctgctgctgc tccagggagg ctggggctgt  60
cctgaccttg tgtgctacac cgactatctg caaaccgtga tttgcattct cgagatgtgg  120
aacctccatc cgtcaaccct gaccctgacg tggcaggacc agtacgaaga actgaaggac  180
gaagccacct cctgttcact gcaccgctcc gcgcacaacg cgactcacgc gacctacact  240
tgccacatgg acgtgttcca cttcggggcc gacgacatct tctccgtgaa catcactgac  300
cagtcgggga actactccca agagtgcgga agctttcttc tggccgagag catcaagccc  360
gctccaccct tcaacgtcac cgtgacttt agcggacagt acaacatctc ctggcggagc  420
gactacgagg atccggcctt ctacatgctg aagggaaagc tgcagtacga actgcagtat  480
aggaatcgcg gggacccgtg ggctgtctcc cctcggcgga agctgatttc cgtggattcg  540
agatccgtgt ccctgctccc actggaattc agaaaagatt cgtcctacga actccaagtc  600
cgcgcaggac ccatgcctgg aagctcatac cagggaacct ggtccgagtg gtcggatccc  660
gtgatcttcc aaaacacagtc cgaagaattg aaggagggct ggaatcccca tctgctgctc  720
ctcctgttgc tggtcatcgt gttcattccg gcgttctggt cactcaagac tcaccctctg  780
tggagactgt ggaagaaaat ctgggcagtg cccagtcccg agcgcttttt catgcctctg  840
tataagggct gctccggaga ctttaagaaa tgggtcggag cccccttcac cggatcgagc  900
ctcgagctgg gcccctggtc ccccgaagtg ccttcgaccc tggaggtgta cagctgccac  960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
agcgcatact ccgaagagag ggacaggccg tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtcccctgg tctgggcggg  1320
cctcttggtt ccctcctgga ccggcttaag ccccgctgg ctgacggaga ggactgggcc  1380
gggggactgc cttggggcgg acgctcacct gggggagtgt cggaatccga agccggctcc  1440
cctttggccg gactggacat ggacacattc gatagcggtt tcgtgggatc cgactgttct  1500
agccccgtgg agtgcgattt cacctccccg ggcgacgagg gtccgccgag atcctacttg  1560
cgccaatggg tggtcattcc ccctccactg tcctccccgg ggccacaggc gtcttga      1617

SEQ ID NO: 25           moltype = DNA  length = 1617
FEATURE                 Location/Qualifiers
misc_feature            1..1617
                        note = Synthetic sequence
source                  1..1617
                        mol_type = other DNA
                        organism = synthetic construct
SEQUENCE: 25
atgccgcgtg gctgggccgc ccccttgctc ctgctgctgc tccagggagg ctggggctgt  60
cctgaccttg tgtgctacac cgactatctg caaaccgtga tttgcattct cgagatgtgg  120
aacctccatc cgtcaaccct gaccctgacg tggcaggacc agtacgaaga actgaaggac  180
gaagccacct cctgttcact gcaccgctcc gcgcacaacg cgactcacgc gacctacact  240
tgccacatgg acgtgttcca cttcatcgcc gacgagatct tctccgtgaa catcactgac  300
cagtcgggga actactccca agagtgcgga agctttcttc tggccgagag catcaagccc  360
gctccaccct tcaacgtcac cgtgactttt agcggacagt acaacatctc ctggcggagc  420
gactacgagg atccggcctt ctacatgctg aagggaaagc tgcagtacga actgcagtat  480
aggaatcgcg gggacccgtg ggctgtctcc cctcggcgga agctgatttc cgtggattcg  540
agatccgtgt ccctgctccc actggaattc agaaaagatt cgtcctacga actccaagtc  600
cgcgcaggac ccatgcctgg aagctcatac cagggaacct ggtccgagtg gtcggatccc  660
gtgatcttcc aaaacacagtc cgaagaattg aaggagggct ggaatcccca tctgctgctc  720
ctcctgttgc tggtcatcgt gttcattccg gcgttctggt cactcaagac tcaccctctg  780
tggagactgt ggaagaaaat ctgggcagtg cccagtcccg agcgcttttt catgcctctg  840
tataagggct gctccggaga ctttaagaaa tgggtcggag cccccttcac cggatcgagc  900
ctcgagctgg gcccctggtc ccccgaagtg ccttcgaccc tggaggtgta cagctgccac  960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
agcgcatact ccgaagagag ggacaggccg tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtcccctgg tctgggcggg  1320
cctcttggtt ccctcctgga ccggcttaag ccccgctgg ctgacggaga ggactgggcc  1380
gggggactgc cttggggcgg acgctcacct gggggagtgt cggaatccga agccggctcc  1440
cctttggccg gactggacat ggacacattc gatagcggtt tcgtgggatc cgactgttct  1500
```

```
agcccegtgg agtgcgattt cacctccccg ggcgacgagg gtccgccgag atcctacttg   1560
cgccaatggg tggtcattcc ccctccactg tcctccccgg ggccacaggc gtcttga     1617

SEQ ID NO: 27           moltype = DNA   length = 630
FEATURE                 Location/Qualifiers
misc_feature            1..630
                        note = Synthetic sequence
source                  1..630
                        mol_type = other DNA
                        organism = synthetic construct
SEQUENCE: 26
atgtacagga tgcaactcct gtcttgcatt gcactaagtc ttgcacttgt cacaaacagt    60
gcccccctggt cgcaccctca attcgaaaag ggtggcggat ccgggggagg cagcggtgga  120
agctcagcgt ggagccaccc gcagttcgag aaagaacaga agttgatttc agaagaagat  180
ctgggcggcg gcggatcggg tggcggggga tccggtggcg gcggaagcca aggacaggac  240
cggctcatga tcaagctccg gcagctcatt gatatcgtgg accagcttaa gaactacgtg  300
aatgacctgg tgccggaatt tctgccagca cccgaggacg tggagactaa ctgcgaatgg  360
tccgccttct cctgcttcca aaaggcccag ctgaagtccg ccaacaccgg aaacaacgag  420
aggatcatca atgtgtcgat caaggtgctt aagcgcaagc tcccttcgac taacgctgag  480
agacggcaga agcaccggct cacgtgccct tcgtgcgact cctacgagaa aaagccaccc  540
aaggaattcc tcgagcgctt caagtcactg ctgcaaaaga tgatccatca gcaccttttcc 600
tctcgcaccc atggatccga ggactcctga                                   630

SEQ ID NO: 27           moltype = DNA   length = 630
FEATURE                 Location/Qualifiers
misc_feature            1..630
                        note = Synthetic sequence
source                  1..630
                        mol_type = other DNA
                        organism = synthetic construct
SEQUENCE: 27
atgtacagga tgcaactcct gtcttgcatt gcactaagtc ttgcacttgt cacaaacagt    60
gcccccctggt cgcaccctca attcgaaaag ggtggcggat ccgggggagg cagcggtgga  120
agctcagcgt ggagccaccc gcagttcgag aaagaacaga agttgatttc agaagaagat  180
ctgggcggcg gcggatcggg tggcggggga tccggtggcg gcggaagcca aggacaggac  240
cggctcatga tcaagctccg gcagctcatt gatatcgtgg accagcttaa gaactacgtg  300
aatgacctgg tgccggaatt tctgccagca cccgaggacg tggagactaa ctgcgaatgg  360
tccgccttct cctgcttcca aaaggcccag ctgaagtccg ccaacaccgg aaacaacgag  420
aggatcatca atgtgtcgat caagatcctt aagcgcaagc tcccttcgac taacgctgag  480
agacggcaga agcaccggct cacgtgccct tcgtgcgact cctacgagaa aaagccagcg  540
aaggaattcc tcgagcgctt caagtcactg ctgcaaaaga tgatccatca gcaccttttcc 600
tctcgcaccc atggatccga ggactcctga                                   630

SEQ ID NO: 28           moltype = DNA   length = 630
FEATURE                 Location/Qualifiers
misc_feature            1..630
                        note = Synthetic sequence
source                  1..630
                        mol_type = other DNA
                        organism = synthetic construct
SEQUENCE: 28
atgtacagga tgcaactcct gtcttgcatt gcactaagtc ttgcacttgt cacaaacagt    60
gcccccctggt cgcaccctca attcgaaaag ggtggcggat ccgggggagg cagcggtgga  120
agctcagcgt ggagccaccc gcagttcgag aaagaacaga agttgatttc agaagaagat  180
ctgggcggcg gcggatcggg tggcggggga tccggtggcg gcggaagcca aggacaggac  240
cggctcatga tcaagctccg gcagctcatt gatatcgtgg accagcttaa gaactacgtg  300
aatgacctgg tgccggaatt tctgccagca cccgaggacg tggagactaa ctgcgaatgg  360
tccgccttct cctgcttcca aaaggcccag ctgaagtccg ccaacaccgg aaacaacgag  420
aggatcatca atgtgtcgat caagatcctt aagcgcaagc tcccttcgac taacgctgga  480
agacggcaga agcaccggct cacgtgccct tcgtgcgact cctacgagaa aaagccaccc  540
aaggaattcc tcgagcgctt caagtcactg ctgcaaaaga tgatccatca gcaccttttcc 600
tctcgcaccc atggatccga ggactcctga                                   630

SEQ ID NO: 29           moltype = DNA   length = 630
FEATURE                 Location/Qualifiers
misc_feature            1..630
                        note = Synthetic sequence
source                  1..630
                        mol_type = other DNA
                        organism = synthetic construct
SEQUENCE: 29
atgtacagga tgcaactcct gtcttgcatt gcactaagtc ttgcacttgt cacaaacagt    60
gcccccctggt cgcaccctca attcgaaaag ggtggcggat ccgggggagg cagcggtgga  120
agctcagcgt ggagccaccc gcagttcgag aaagaacaga agttgatttc agaagaagat  180
ctgggcggcg gcggatcggg tggcggggga tccggtggcg gcggaagcca aggacaggac  240
cggctcatga tcaagctccg gcagctcatt gatatcgtgg accagcttaa gaactacgtg  300
aatgacctgg tgccggaatt tctgccagca cccgaggacg tggagactaa ctgcgaatgg  360
tccgccttct cctgcttcca aaaggcccag ctgaagtccg ccaacaccgg aaacaacgag  420
aggatcatca atgtgtcgat caagatcctt aagcgcaagc tcccttcgac taacgctgag  480
```

```
agacggcaga agcaccggct cacgtgccct tcgtgcgact cctacgagaa aaagccagtg    540
aaggaattcc tcgagcgctt caagtcactg ctgcaaaaga tgatccatca gcacctttcc    600
tctcgcaccc atggatccga ggactcctga                                      630

SEQ ID NO: 30          moltype = DNA   length = 630
FEATURE                Location/Qualifiers
misc_feature           1..630
                       note = Synthetic sequence
source                 1..630
                       mol_type = other DNA
                       organism = synthetic construct
SEQUENCE: 30
atgtacagga tgcaactcct gtcttgcatt gcactaagtc ttgcacttgt cacaaacagt    60
gcccectggt cgcaccctca attcgaaaag ggtggcggat ccggggagg cagcggtgga    120
agctcagcgt ggagccaccc gcagttcgag aaagaacaga agttgatttc agaagaagat    180
ctgggcggcg gcggatcggg tggcggggga tccggtggcg gcggaagcca aggacaggac    240
cggctcatga tccgcctccg gcagctcatt gatatcgtgg accagcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
aggatcatca atgtgtcgat caaggtgctt aagaagaagc cccttcgac taacgctggc    480
agacggcaga agcaccggct cacgtgccct tcgtgcgact cctacgagaa aaagccagcg    540
aaggaattcc tcgagcgctt caagtcactg ctgcaaaaga tgatccatca gcacctttcc    600
tctcgcaccc atggatccga ggactcctga                                      630

SEQ ID NO: 31          moltype = DNA   length = 630
FEATURE                Location/Qualifiers
misc_feature           1..630
                       note = Synthetic sequence
source                 1..630
                       mol_type = other DNA
                       organism = synthetic construct
SEQUENCE: 31
atgtacagga tgcaactcct gtcttgcatt gcactaagtc ttgcacttgt cacaaacagt    60
gcccectggt cgcaccctca attcgaaaag ggtggcggat ccggggagg cagcggtgga    120
agctcagcgt ggagccaccc gcagttcgag aaagaacaga agttgatttc agaagaagat    180
ctgggcggcg gcggatcggg tggcggggga tccggtggcg gcggaagcca aggacaggac    240
cggctcatga tccggctccg gcagctcatt gatatcgtgg accagcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
aggatcatca atgtgtcgat caagctcctt aagcgcaagc tcccttcgac taacgctgga    480
agacggcaga agcaccggct cacgtgccct tcgtgcgact cctacgagaa aaagccaccc    540
aaggaattcc tcgagcgctt caagtcactg ctgcaaaaga tgatccatca gcacctttcc    600
tctcgcaccc atggatccga ggactcctga                                      630

SEQ ID NO: 32          moltype = DNA   length = 630
FEATURE                Location/Qualifiers
misc_feature           1..630
                       note = Synthetic sequence
source                 1..630
                       mol_type = other DNA
                       organism = synthetic construct
SEQUENCE: 32
atgtacagga tgcaactcct gtcttgcatt gcactaagtc ttgcacttgt cacaaacagt    60
gcccectggt cgcaccctca attcgaaaag ggtggcggat ccggggagg cagcggtgga    120
agctcagcgt ggagccaccc gcagttcgag aaagaacaga agttgatttc agaagaagat    180
ctgggcggcg gcggatcggg tggcggggga tccggtggcg gcggaagcca aggacaggac    240
cggctcatga tccggctccg gcagctcatt gatatcgtgg accagcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
aggatcatca atgtgtcgat caagatgctt aagcacaagc tcccttcgac taacgctgag    480
agacggcaga agcaccggct cacgtgccct tcgtgcgact cctacgagaa aaagccaccc    540
aaggaattcc tcgagcgctt caagtcactg ctgcaaaaga tgatccatca gcacctttcc    600
tctcgcaccc atggatccga ggactcctga                                      630

SEQ ID NO: 33          moltype = DNA   length = 630
FEATURE                Location/Qualifiers
misc_feature           1..630
                       note = Synthetic sequence
source                 1..630
                       mol_type = other DNA
                       organism = synthetic construct
SEQUENCE: 33
atgtacagga tgcaactcct gtcttgcatt gcactaagtc ttgcacttgt cacaaacagt    60
gcccectggt cgcaccctca attcgaaaag ggtggcggat ccggggagg cagcggtgga    120
agctcagcgt ggagccaccc gcagttcgag aaagaacaga agttgatttc agaagaagat    180
ctgggcggcg gcggatcggg tggcggggga tccggtggcg gcggaagcca aggacaggac    240
cggctcatga tccggctccg gcagctcatt gatatcgtgg accagcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
```

```
aggatcatca atgtgtcgat caagctcctt aagcgcaagc tccctcccac taacgctggc    480
agacggcaga agcaccggct cacgtgccct tcgtgcgact cctacgaaaa aaagccagcg    540
aaggaattcc tcgagcgctt caagtcactg ctgcaaaaga tgatccatca gcacctttcc    600
tctcgcaccc atggatccga ggactcctga                                    630

SEQ ID NO: 34           moltype = AA   length = 340
FEATURE                 Location/Qualifiers
REGION                  1..340
                        note = Synthetic sequence
source                  1..340
                        mol_type = protein
                        organism = synthetic construct
SEQUENCE: 34
MRSSPGNMER IVICLMVIFL GTLVHKSSSQ GQDRHMIRMR QLIDIVDQLK NYVNDLVPEF     60
LPAPEDVETN CEWSAFSCFQ KAQLKSANTG NNERIINVSI KKLKRKPPST NAGRRQKHRL    120
TCPSCDSYEK KPPKEFLERF KSLLQKMIHQ HLSSRTHGSE DSGGGGSGGG GSGGGGSMEA    180
EAERGKLPGK KLPLEVLIEL EANARKAGCT RGCLICLSKI KCTAKMKKYI PGRCADYGGD    240
KKTGQAGIVG AIVDIPEISG FKEMEPMEQF IAQVDRCADC TTGCLKGLAN VKCSDLLKKW    300
LPGRCATFAD KIQSEVDNIK GLAGDGGGGS GGGGSGGGGS                         340

SEQ ID NO: 35           moltype = DNA   length = 1617
FEATURE                 Location/Qualifiers
misc_feature            1..1617
                        note = Synthetic sequence
source                  1..1617
                        mol_type = other DNA
                        organism = synthetic construct
SEQUENCE: 35
atgccgcgtg gctgggccgc cccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaga actgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagcca   360
gctccaccct tcaacgtcac cgtgacttt agcggacagt acaacatctc ctggcgggag   420
gactacgagg atccgatgtt ctacatgctg aagggaaagc tgcagtacga actgcagtat   480
aggaatcgcg gggaccgtgg gctgtctcc ctcggcggaa gctgatttc cgtggattcg   540
agatccgtgt ccctgctccc actggaattc agaaaagatt cgtcctacga actccaagtc   600
cgcgcaggac ccatgcctgg aagctcatac cagggaacct ggtccgagtg gtcggatccc   660
gtgatcttcc aaacagtcc gaagaattg aaggaggct gaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgctttt catgcctctg   840
tataaggget gctccggaga ctttaagaaa tgggtcgtc ccccttcac cggatcgagc   900
ctcgagctgg gccctgtc ccccgaagtg ccttcgaccc tggaggtgta cagctgccac   960
ccgcaagaa gccccgctaa gcgctgcag ctgaccgagc tgcaggaacc agccgaactg  1020
gtcgagtcag acgcgtgcc aaagccatcc ttctggccca ccgcccaaaa ctcgggtgga  1080
agcgcatact ccgaagagag ggacaggcg tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtccctgg tctgggcggg  1320
cctcttggtt ccctcctgga ccggcttaag cccccgtcg tgacggaga ggactgggga  1380
gggggactgc cttggggcgg acgctcacct gggggagtgt cggaatccga agccggctgc  1440
cctttggccg gactggacat ggacacattc gatagcggtt tcgtgggatc cgactgttct  1500
agccccgtgg agtgcgattt cacctccccg ggcgacgagg tccgccgag atcctacttg  1560
cgccaatggg tggtcattcc ccctccactg tcctccccg ggcgacaggc gtcttga     1617

SEQ ID NO: 36           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 36
CPDLVCYTDY LQTVICILEM WNLHPSTLTL TWHDQYEDLK DEATSCSLHR SAHNATHATY     60
TCHMDVFQFM ADDIFSVNIT DQSGNYSQEC GSFLLAESIK PAPPFNVTVT FSGQYNISWR    120
SDYEDPAFYM LKGKLQYELQ YRNRGDPWAV SPRRKLISVD SRSVSLLPLE FRKDSSYELQ    180
VRAGPMPGSS YQGTWSEWSD PVIFQTQSEE LKE                                213

SEQ ID NO: 37           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 37
CPDLVCYTDY LQTVICILEM WNLHPSTLTL TWQDQYEELK DEATSCSLHR SAHNATHATY     60
TCHMDVFHFM AEEIFSVNIT DQSGNYSQEC GSFLLAESIK PAPPFNVTVT FSGQYNISWR    120
```

```
SDYEDPAFFM LKGKLQYELQ YRNRGDPWAV SPRRKLISVD SRSVSLLPLE FRKDSSYELQ     180
VRAGPMPGSS YQGTWSEWSD PVIFQTQSEE LKE                                 213

SEQ ID NO: 38            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 38
CPDLVCYTDY LQTVICILEM WNLHPSTLTL TWQDQYEELK DEATSCSLHR SAHNATHATY     60
TCHMDVFQFM ADDIFSVNIT DQSGNYSQEC GSFLLAESIK PAPPFNVTVT FSGQYNISWR     120
SDYEDPAFFM LKGKLQYELQ YRNRGDPWAV SPRRKLISVD SRSVSLLPLE FRKDSSYELQ     180
VRAGPMPGSS FQGTWSEWSD PVIFQTQSEE LKE                                 213

SEQ ID NO: 39            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 39
CPDLVCYTDY LQTVICILEM WNLHPSTLTL TWQDQFEELK DEATSCSLHR SAHNATHATY     60
TCHMDVFQFM ADEIFSVNIT DQSGNYSQEC GSFLLAESIK PAPPFNVTVT FSGQYNISWR     120
SDYEDPAFYM LKGKLQYELQ YRNRGDPWAV SPRRKLISVD SRSVSLLPLE FRKDSSYELQ     180
VRAGPMPGSS YQGTWSEWSD PVIFQTQSEE LKE                                 213

SEQ ID NO: 40            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 40
CPDLVCYTDY LQTVICILEM WNLHPSTLTL TWQDQYEELK DEATSCSLHR SAHNATHATY     60
TCHMDVYHFM ADDIFSVNIT DQSGNYSQEC GSFLLAESIK PAPPFNVTVT FSGQYNISWR     120
SDYEDPAFFL LKGKLQYELQ YRNRGDPWAV SPRRKLISVD SRSVSLLPLE FRKDSSYELQ     180
VRAGPMPGSS YQGTWSEWSD PVIFQTQSEE LKE                                 213

SEQ ID NO: 41            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 41
CPDLVCYTDY LQTVICILEM WNLHPSTLTL TWQDQYEELK DEATSCSLHR SAHNATHATY     60
TCHMDVFHFM AEDIFSVNIT DQSGNYSQEC GSFVLAESIK PAPPFNVTVT FSGQYNISWR     120
SDYEDPAFYM LKGKLQYELQ YRNRGDPWAV SPRRKLISVD SRSVSLLPLE FRKDSSYELQ     180
VRAGPMPGSS FQGTWSEWSD PVIFQTQSEE LKE                                 213

SEQ ID NO: 42            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 42
CPDLVCYTDY LQTVICILEM WNLHPSTLTL TWHDQYEELK DEATSCSLHR SAHNATHATY     60
TCHMDVFHFM ADDIFSVNIT DQSGNYSQEC GSFVLAESIK PAPPFNVTVT FSGQYNISWR     120
SDYEDPAFYL LKGKLQYELQ YRNRGDPWAV SPRRKLISVD SRSVSLLPLE FRKDSSYELQ     180
VRAGPMPGSS YQGTWSEWSD PVIFQTQSEE LKE                                 213

SEQ ID NO: 43            moltype = AA  length = 213
FEATURE                  Location/Qualifiers
REGION                   1..213
                         note = Synthetic sequence
source                   1..213
                         mol_type = protein
                         organism = synthetic construct
SEQUENCE: 43
CPDLVCYTDY LQTVICILEM WNLHPSTLTL TWQDQFEDLK DEATSCSLHR SAHNATHATY     60
TCHMDVYHFM ADDIFSVNIT DQSGNYSQEC GSFLLAESIK PAPPFNVTVT FSGQYNISWR     120
SDYEDPAFYM LKGKLQYELQ YRNRGDPWAV SPRRKLISVD SRSVSLLPLE FRKDSSYELQ     180
```

```
VRAGPMPGSS YQGTWSEWSD PVIFQTQSEE LKE                             213

SEQ ID NO: 44           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 44
CPDLVCYTDY LQTVICILEM WNLHPSTLTL TWQDQYEDLK DEATSCSLHR SAHNATHATY  60
TCHMDVFHFM AEDIFSVNIT DQSGNYSQEC GSFLLAESIK PAPPFNVTVT FSGQYNISWR  120
SDYEDPAFYL LKGKLQYELQ YRNRGDPWAV SPRRKLISVD SRSVSLLPLE FRKDSSYELQ  180
VRAGPMPGSS YQGTWSEWSD PVIFQTQSEE LKE                              213

SEQ ID NO: 45           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 45
CPDLVCYTDY LQTVICILEM WNLHPSTLTL TWQDQFEELK DEATSCSLHR SAHNATHATY  60
TCHMDVFHFI ADDIFSVNIT DQSGNYSQEC GSFVLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                              213

SEQ ID NO: 46           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 46
CPDLVCYTDY LQTVICILEM WNLHPSTLTL TWQDQYEELK DEATSCSLHR SAHNATHATY  60
TCHMDVYHFI ADDIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS FQGTWSEWSD PVIFQTQSEE LKE                              213

SEQ ID NO: 47           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 47
CPDLVCYTDY LQTVICILEM WNLHPSTLTL TWQDQHEELK DEATSCSLHR SAHNATHATY  60
TCHMDVFHFM ADDIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                              213

SEQ ID NO: 48           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 48
CPDLVCYTDY LQTVICILEM WNLHPSTLTL TWQDQYEELK DEATSCSLHR SAHNATHATY  60
TCHMDVFHLL ADIIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                              213

SEQ ID NO: 49           moltype = AA  length = 213
FEATURE                 Location/Qualifiers
REGION                  1..213
                        note = Synthetic sequence
source                  1..213
                        mol_type = protein
                        organism = synthetic construct
SEQUENCE: 49
CPDLVCYTDY LQTVICILEM WNLHPSTLTL TWQDQYEELK DEATSCSLHR SAHNATHATY  60
TCHMDVFHFM ADDIFSVNIT DQSGNYSQEC GSFLLAESIK PAPPFNVTVT FSGQYNISWR  120
SDYEDPAFHF LKGKLQYELQ YRNRGDPWAV SPRRKLISVD SRSVSLLPLE FRKDSSYELQ  180
VRAGPMPGSS YQGTWSEWSD PVIFQTQSEE LKE                              213
```

```
SEQ ID NO: 50           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 50
CPDLVCYTDY LQTVICILEM WNLHPSTLTL TWQDQYEELK DEATSCSLHR SAHNATHATY    60
TCHMDVFHFM ADDIFSVNIT DQSGNYSQEC GSFLLAESIK PAPPFNVTVT FSGQYNISWR   120
SDYEDPAFFS LKGKLQYELQ YRNRGDPWAV SPRRKLISVD SRSVSLLPLE FRKDSSYELQ   180
VRAGPMPGSS YQGTWSEWSD PVIFQTQSEE LKE                                213

SEQ ID NO: 51           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 51
CPDLVCYTDY LQTVICILEM WNLHPSTLTL TWQDQYEELK DEATSCSLHR SAHNATHATY    60
TCHMDVFHFM AKKIFSVNIT DQSGNYSQEC GSFLLAESIK PAPPFNVTVT FSGQYNISWR   120
SDYEDPAFYM LKGKLQYELQ YRNRGDPWAV SPRRKLISVD SRSVSLLPLE FRKDSSYELQ   180
VRAGPMPGSS YQGTWSEWSD PVIFQTQSEE LKE                                213

SEQ ID NO: 52           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 52
CPDLVCYTDY LQTVICILEM WNLHPSTLTL TWQDQYEKLK DEATSCSLHR SAHNATHATY    60
TCHMDVFHFM ADDIFSVNIT DQSGNYSQEC GSFLLAESIK PAPPFNVTVT FSGQYNISWR   120
SDYEDPAFYM LKGKLQYELQ YRNRGDPWAV SPRRKLISVD SRSVSLLPLE FRKDSSYELQ   180
VRAGPMPGSS YQGTWSEWSD PVIFQTQSEE LKE                                213

SEQ ID NO: 53           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 53
CPDLVCYTDY LQTVICILEM WNLHPSTLTL TWQDQYEELK DEATSCSLHR SAHNATHATY    60
TCHMDVFHFM ADDIFSVNIT DQSGNYSQEC GSFLLAESIK PAPPFNVTVT FSGQYNISWR   120
SDYEDPAFYM LKGKLQYELQ YRNRGDPWAV SPRRKLISVD SRSVSLLPLE FRKDSSYELQ   180
VRAGPMPGSS YQGTWSEWSD PVIFQTQSEE LKE                                213

SEQ ID NO: 54           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 54
CPDLVCYTDY LQTVICILEM WNLHPSTLTL TWQDQYEELK DEATSCSLHR SAHNATHATY    60
TCHMDVFHFL ADDIFSVNIT DQSGNYSQEC GSFLLAESIK PAPPFNVTVT FSGQYNISWR   120
SDYEDPAFYM LKGKLQYELQ YRNRGDPWAV SPRRKLISVD SRSVSLLPLE FRKDSSYELQ   180
VRAGPMPGSS YQGTWSEWSD PVIFQTQSEE LKE                                213

SEQ ID NO: 55           moltype = AA   length = 213
FEATURE                 Location/Qualifiers
REGION                  1..213
                        note = Synthetic sequence
source                  1..213
                        mol_type = protein
                        organism = synthetic construct
SEQUENCE: 55
CPDLVCYTDY LQTVICILEM WNLHPSTLTL TWQDQYEELK DEATSCSLHR SAHNATHATY    60
TCHMDVFHLM ADDIFSVNIT DQSGNYSQEC GSFLLAESIK PAPPFNVTVT FSGQYNISWR   120
SDYEDPAFYM LKGKLQYELQ YRNRGDPWAV SPRRKLISVD SRSVSLLPLE FRKDSSYELQ   180
VRAGPMPGSS YQGTWSEWSD PVIFQTQSEE LKE                                213
```

```
SEQ ID NO: 56              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 56
CPDLVCYTDY LQTVICILEM WNLHPSTLTL TWQDQYEELK DEATSCSLHR SAHNATHATY    60
TCHMDVFHFM ADIIFSVNIT DQSGNYSQEC GSFLLAESIK PAPPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                                213

SEQ ID NO: 57              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 57
CPDLVCYTDY LQTVICILEM WNLHPSTLTL TWQDQYEELK DEATSCSLHR SAHNATHATY    60
TCHMDVFHFM ADEIFSVNIT DQSGNYSQEC GSFLLAESIK PAPPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                                213

SEQ ID NO: 58              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 58
CPDLVCYTDY LQTVICILEM WNLHPSTLTL TWQDQYEELK DEATSCSLHR SAHNATHATY    60
TCHMDVFHFG ADEIFSVNIT DQSGNYSQEC GSFLLAESIK PAPPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                                213

SEQ ID NO: 59              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 59
CPDLVCYTDY LQTVICILEM WNLHPSTLTL TWHDQYEELK DEATSCSLHR SAHNATHATY    60
TCHMDVFHFG ADEIFSVNIT DQSGNYSQEC GSFLLAESIK PAPPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                                213

SEQ ID NO: 60              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 60
CPDLVCYTDY LQTVICILEM WNLHPSTLTL TWQDQYEKLK DEATSCSLHR SAHNATHATY    60
TCHMDVFHFI ADDIFSVNIT DQSGNYSQEC GSFLLAESIK PAPPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                                213

SEQ ID NO: 61              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 61
APWSHPQFEK GGGSGGGSGG SSAWSHPQFE KGGGGSGGGG SGGGGSQGQD QHMIRMRQLI    60
DIVDQLKNYV NDLVPEFLPA PEDVETNCEW SAFSCFQKAQ LKSANTGNNE RIINVSIKKL  120
KRKPPSTNAG RRQKHRLTCP SCDSYEKKPP KEFLERFKSL LQKMIHQHLS SRTHGSEDSG  180
GGGSGGGGSE QKLISEEDL                                               199

SEQ ID NO: 62              moltype = AA  length = 199
```

| FEATURE | Location/Qualifiers |
|---|---|
| REGION | 1..199 |
| | note = Synthetic sequence |
| source | 1..199 |
| | mol_type = protein |
| | organism = synthetic construct |

SEQUENCE: 62
```
APWSHPQFEK GGGSGGGSGG SSAWSHPQFE KGGGGSGGGG SGGGGSQGQD DHMIRMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 63 | moltype = AA length = 199 |
|---|---|
| FEATURE | Location/Qualifiers |
| REGION | 1..199 |
| | note = Synthetic sequence |
| source | 1..199 |
| | mol_type = protein |
| | organism = synthetic construct |

SEQUENCE: 63
```
APWSHPQFEK GGGSGGGSGG SSAWSHPQFE KGGGGSGGGG SGGGGSQGQD EHMIRMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 64 | moltype = AA length = 199 |
|---|---|
| FEATURE | Location/Qualifiers |
| REGION | 1..199 |
| | note = Synthetic sequence |
| source | 1..199 |
| | mol_type = protein |
| | organism = synthetic construct |

SEQUENCE: 64
```
APWSHPQFEK GGGSGGGSGG SSAWSHPQFE KGGGGSGGGG SGGGGSQGQD KHMIRMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 65 | moltype = AA length = 199 |
|---|---|
| FEATURE | Location/Qualifiers |
| REGION | 1..199 |
| | note = Synthetic sequence |
| source | 1..199 |
| | mol_type = protein |
| | organism = synthetic construct |

SEQUENCE: 65
```
APWSHPQFEK GGGSGGGSGG SSAWSHPQFE KGGGGSGGGG SGGGGSQGQD NHMIRMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 66 | moltype = AA length = 199 |
|---|---|
| FEATURE | Location/Qualifiers |
| REGION | 1..199 |
| | note = Synthetic sequence |
| source | 1..199 |
| | mol_type = protein |
| | organism = synthetic construct |

SEQUENCE: 66
```
APWSHPQFEK GGGSGGGSGG SSAWSHPQFE KGGGGSGGGG SGGGGSQGQD RHMERMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 67 | moltype = AA length = 199 |
|---|---|
| FEATURE | Location/Qualifiers |
| REGION | 1..199 |
| | note = Synthetic sequence |
| source | 1..199 |
| | mol_type = protein |
| | organism = synthetic construct |

SEQUENCE: 67
```
APWSHPQFEK GGGSGGGSGG SSAWSHPQFE KGGGGSGGGG SGGGGSQGQD RHMIEMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                                199
```

| SEQ ID NO: 68 | moltype = AA length = 199 |
|---|---|
| FEATURE | Location/Qualifiers |

```
REGION                     1..199
                           note = Synthetic sequence
source                     1..199
                           mol_type = protein
                           organism = synthetic construct
SEQUENCE: 68
APWSHPQFEK GGGSGGGSGG SSAWSHPQFE KGGGGSGGGG SGGGGSQGQD RHMIDMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 69              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 69
APWSHPQFEK GGGSGGGSGG SSAWSHPQFE KGGGGSGGGG SGGGGSQGQD RHMIKMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 70              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 70
APWSHPQFEK GGGSGGGSGG SSAWSHPQFE KGGGGSGGGG SGGGGSQGQD RHMINMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 71              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 71
APWSHPQFEK GGGSGGGSGG SSAWSHPQFE KGGGGSGGGG SGGGGSQGQD RHMIQMRQLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 72              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 72
APWSHPQFEK GGGSGGGSGG SSAWSHPQFE KGGGGSGGGG SGGGGSQGQD RHMIRMRVLI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 73              moltype = AA  length = 199
FEATURE                    Location/Qualifiers
REGION                     1..199
                           note = Synthetic sequence
source                     1..199
                           mol_type = protein
                           organism = synthetic construct
SEQUENCE: 73
APWSHPQFEK GGGSGGGSGG SSAWSHPQFE KGGGGSGGGG SGGGGSQGQD RHMIRMRQDI    60
DIVDQLKNYV NDLVPEFLPA PEDVETNCEW SAFSCFQKAQ LKSANTGNNE RIINVSIKKL   120
KRKPPSTNAG RRQKHRLTCP SCDSYEKKPP KEFLERFKSL LQKMIHQHLS SRTHGSEDSG   180
GGGSGGGGSE QKLISEEDL                                               199

SEQ ID NO: 74              moltype = AA  length = 199
FEATURE                    Location/Qualifiers
REGION                     1..199
```

```
                            note = Synthetic sequence
source                      1..199
                            mol_type = protein
                            organism = synthetic construct
SEQUENCE: 74
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKVL  120
KRKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 75               moltype = AA   length = 199
FEATURE                     Location/Qualifiers
REGION                      1..199
                            note = Synthetic sequence
source                      1..199
                            mol_type = protein
                            organism = synthetic construct
SEQUENCE: 75
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKDL  120
KRKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 76               moltype = AA   length = 199
FEATURE                     Location/Qualifiers
REGION                      1..199
                            note = Synthetic sequence
source                      1..199
                            mol_type = protein
                            organism = synthetic construct
SEQUENCE: 76
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKKL  120
DRKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 77               moltype = AA   length = 199
FEATURE                     Location/Qualifiers
REGION                      1..199
                            note = Synthetic sequence
source                      1..199
                            mol_type = protein
                            organism = synthetic construct
SEQUENCE: 77
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKKL  120
KEKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 78               moltype = AA   length = 199
FEATURE                     Location/Qualifiers
REGION                      1..199
                            note = Synthetic sequence
source                      1..199
                            mol_type = protein
                            organism = synthetic construct
SEQUENCE: 78
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKKL  120
KNKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 79               moltype = AA   length = 199
FEATURE                     Location/Qualifiers
REGION                      1..199
                            note = Synthetic sequence
source                      1..199
                            mol_type = protein
                            organism = synthetic construct
SEQUENCE: 79
APWSHPQFEK GGGSGGGSGG SSAWSHPQFE KGGGGSGGGG SGGGGSQGQD RHMIRMRQLI   60
DIVDQLKNYV NDLVPEFLPA PEDVETNCEW SAFSCFQKAQ LKSANTGNNE RIINVSIKKL  120
KAKPPSTNAG RRQKHRLTCP SCDSYEKKPP KEFLERFKSL LQKMIHQHLS SRTHGSEDSG  180
GGGSGGGSE QKLISEEDL                                                199

SEQ ID NO: 80               moltype = AA   length = 199
FEATURE                     Location/Qualifiers
REGION                      1..199
                            note = Synthetic sequence
```

```
source                    1..199
                          mol_type = protein
                          organism = synthetic construct
SEQUENCE: 80
APWSHPQFEK GGGSGGGSGG SSAWSHPQFE KGGGGSGGGG SGGGGSQGQD QHMIRMRQLI    60
DIVDQLKNYV NDLVPEFLPA PEDVETNCEW SAFSCFQKAQ LKSANTGNNE RIINVSIKKL   120
KEKPPSTNAG RRQKHRLTCP SCDSYEKKPP KEFLERFKSL LQKMIHQHLS SRTHGSEDSG   180
GGGSGGGGSE QKLISEEDL                                                199

SEQ ID NO: 81             moltype = AA  length = 199
FEATURE                   Location/Qualifiers
REGION                    1..199
                          note = Synthetic sequence
source                    1..199
                          mol_type = protein
                          organism = synthetic construct
SEQUENCE: 81
APWSHPQFEK GGGSGGGSGG SSAWSHPQFE KGGGGSGGGG SGGGGSQGQD QHMIRMRQLI    60
DIVDQLKNYV NDLVPEFLPA PEDVETNCEW SAFSCFQKAQ LKSANTGNNE RIINVSIKKL   120
KAKPPSTNAG RRQKHRLTCP SCDSYEKKPP KEFLERFKSL LQKMIHQHLS SRTHGSEDSG   180
GGGSGGGGSE QKLISEEDL                                                199

SEQ ID NO: 82             moltype = AA  length = 189
FEATURE                   Location/Qualifiers
REGION                    1..189
                          note = Synthetic sequence
source                    1..189
                          mol_type = protein
                          organism = synthetic construct
SEQUENCE: 82
APWSHPQFEK GGGSGGGSGG SSAWSHPQFE KEQKLISEED LGGGGSGGGG SGGGGSQGQD    60
RLMIRLSQLI DVVDQLKNYV NDLVPEFLPA PEDVETNCEW SAFSCFQKAQ LKSANTGNNE   120
RIINVSIKLL KHKLPSTNAG RRQKHRLTCP SCDSYEKKPP KEFLERFKSL LQKMIHQHLS   180
SRTHGSEDS                                                            189

SEQ ID NO: 83             moltype = AA  length = 189
FEATURE                   Location/Qualifiers
REGION                    1..189
                          note = Synthetic sequence
source                    1..189
                          mol_type = protein
                          organism = synthetic construct
SEQUENCE: 83
APWSHPQFEK GGGSGGGSGG SSAWSHPQFE KEQKLISEED LGGGGSGGGG SGGGGSQGQD    60
RLMIRLSQLI DVVDFLKNYV NDLVPEFLPA PEDVETNCEW SAFSCFQKAQ LKSANTGNNE   120
RSINVSIKLL KHKLPKTNAG RRQKHRLTCP SCDSYEKKPP KEFLERFKSL LQKMIHQHLS   180
SRTHGSEDS                                                            189

SEQ ID NO: 84             moltype = AA  length = 189
FEATURE                   Location/Qualifiers
REGION                    1..189
                          note = Synthetic sequence
source                    1..189
                          mol_type = protein
                          organism = synthetic construct
SEQUENCE: 84
APWSHPQFEK GGGSGGGSGG SSAWSHPQFE KEQKLISEED LGGGGSGGGG SGGGGSQGQD    60
RLMIRLTQLI DVVDQLKNYV NDLVPEFLPA PEDVETNCEW SAFSCFQKAQ LKSANTGNNE   120
RIINVSIKLL KHKLPVTNAG RRQKHRLTCP SCDSYEKKPI KEFLERFKSL LQKMIHQHLS   180
SRTHGSEDS                                                            189

SEQ ID NO: 85             moltype = AA  length = 538
FEATURE                   Location/Qualifiers
REGION                    1..538
                          note = Synthetic sequence
source                    1..538
                          mol_type = protein
                          organism = synthetic construct
SEQUENCE: 85
MPRGWAAPLL LLLLQGGWGC PDLVCYTDYL QTVICILEMW NLHPSTLTLT WQDQYETLKD    60
EATSCSLHRS AHNATHATYT CHMDVFHFIA DEIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS     538
```

```
SEQ ID NO: 86              moltype = AA   length = 538
FEATURE                    Location/Qualifiers
REGION                     1..538
                           note = Synthetic sequence
source                     1..538
                           mol_type = protein
                           organism = synthetic construct
SEQUENCE: 86
MPRGWAAPLL LLLLQGGWGC PDLVCYTDYL QTVICILEMW NLHPSTLTLT WQDQYEHLKD    60
EATSCSLHRS AHNATHATYT CHMDVFHFIA DEIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 87              moltype = AA   length = 538
FEATURE                    Location/Qualifiers
REGION                     1..538
                           note = Synthetic sequence
source                     1..538
                           mol_type = protein
                           organism = synthetic construct
SEQUENCE: 87
MPRGWAAPLL LLLLQGGWGC PDLVCYTDYL QTVICILEMW NLHPSTLTLT WQDQYEELKD    60
EATSCSLHRS AHNATHATYT CHMDVFHFIA DEIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 88              moltype = AA   length = 538
FEATURE                    Location/Qualifiers
REGION                     1..538
                           note = Synthetic sequence
source                     1..538
                           mol_type = protein
                           organism = synthetic construct
SEQUENCE: 88
MPRGWAAPLL LLLLQGGWGC PDLVCYTDYL QTVICILEMW NLHPSTLTLT WQDQYEELKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 89              moltype = DNA   length = 630
FEATURE                    Location/Qualifiers
misc_feature               1..630
                           note = Synthetic sequence
source                     1..630
                           mol_type = other DNA
                           organism = synthetic construct
SEQUENCE: 89
atgtacagga tgcaactcct gtcttgcatt gcactaagtc ttgcacttgt cacaaaacagt    60
gcccctggt cgcaccctca attcgaaaag ggtggcggat ccggggggagg cagcggtgga   120
agctcagcgt ggagccaccc gcagttcgag aaagaacaga agttgatttc agaagaagat   180
ctgggcggcg gcgggatcggg tggcggggga tccgtggcg gcggaagcca aggacaggac   240
cggctcatga tccggctctc gcagctcatt gatgtggtgg accagcttaa gaactacgtg   300
aatgacctgg tgccggaatt tctgccagca cccgaggacg tggagactaa ctgcgaatgg   360
tccgccttct cctgcttcca aaaggcccag tgaagtccg ccaacaccgg aaacaacgag   420
aggatcatca atgtgtcgat caagctcctt aagcacaagc tccctttcgac taacgctgga   480
agacggcaga agcaccggct cacgtgccct tcgtgcgact cctacgagaa aaagccaccc   540
aaggaattcc tcgagcgctt caagtcactg ctgcaaaaga tgatccatca gcacctttcc   600
tctcgcaccc atggatccga ggactcctga                                    630

SEQ ID NO: 90              moltype = DNA   length = 630
FEATURE                    Location/Qualifiers
misc_feature               1..630
                           note = Synthetic sequence
source                     1..630
```

```
                        mol_type = other DNA
                        organism = synthetic construct
SEQUENCE: 90
atgtacagga tgcaactcct gtcttgcatt gcactaagtc ttgcacttgt cacaaacagt    60
gccccctggt cgcaccctca attcgaaaag ggtggcggat ccggggagg cagcggtgga    120
agctcagcgt ggagccaccc gcagttcgag aaagaacaga agttgatttc agaagaagat    180
ctggcggcg gcggatcggg tggcggggga tccgtggcg gcggaagcca aggacaggac     240
cggctcatga tccggctctc gcagctcatt gatgtggtgg actttcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
aggtcgatca atgtgtcgat caagctcctt aagcacaagc tccctaagac taacgctgga    480
agacggcaga agcaccggct cacgtgccct tcgtgcgact cctacgagaa aaagccaccc    540
aaggaattcc tcgagcgctt caagtcactg ctgcaaaaga tgatccatca gcacctttcc    600
tctcgcaccc atggatccga ggactcctga                                    630

SEQ ID NO: 91        moltype = DNA   length = 630
FEATURE              Location/Qualifiers
misc_feature         1..630
                     note = Synthetic sequence
source               1..630
                     mol_type = other DNA
                     organism = synthetic construct
SEQUENCE: 91
atgtacagga tgcaactcct gtcttgcatt gcactaagtc ttgcacttgt cacaaacagt    60
gccccctggt cgcaccctca attcgaaaag ggtggcggat ccggggagg cagcggtgga    120
agctcagcgt ggagccaccc gcagttcgag aaagaacaga agttgatttc agaagaagat    180
ctggcggcg gcggatcggg tggcggggga tccgtggcg gcggaagcca aggacaggac     240
cggctcatga tccggctcac gcagctcatt gatgtggtgg accagcttaa gaactacgtg    300
aatgacctgg tgccggaatt tctgccagca cccgaggacg tggagactaa ctgcgaatgg    360
tccgccttct cctgcttcca aaaggcccag ctgaagtccg ccaacaccgg aaacaacgag    420
aggatcatca atgtgtcgat caagctcctt aagcacaagc tccctgtgac taacgctgga    480
agacggcaga agcaccggct cacgtgccct tcgtgcgact cctacgagaa aaagccaatc    540
aaggaattcc tcgagcgctt caagtcactg ctgcaaaaga tgatccatca gcacctttcc    600
tctcgcaccc atggatccga ggactcctga                                    630

SEQ ID NO: 92        moltype = DNA   length = 1617
FEATURE              Location/Qualifiers
misc_feature         1..1617
                     note = Synthetic sequence
source               1..1617
                     mol_type = other DNA
                     organism = synthetic construct
SEQUENCE: 92
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaac gctgaaggac   180
gaagccacct cctgttcact gcaccgctcc gcgcacaacg tcatcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccacctt tcaacgtcac cgtgactttt agcggacagt acaacatctc ctggcggagc   420
gactacgagg atccggcctt ctacatgctg aagggaaagc tgcagtacga actgcagtat   480
aggaatcgcg gggaccctgtg ggctgtctcc cctcggcgga agctgatttc cgtggattgc   540
agatccgtgt ccctgctccc actggaattc agaaaagatt cgtcctacga actccaagtc   600
cgcgcaggac ccatgcctgg aagctcatac cagggaacct ggtccgagtg gtcggatccc   660
gtgatcttcc aaacacagtc cgaagaattg aaggagggct ggaatcccca tctgctgctc   720
ctcctgttgc tggtcatcgt gttcattccg gcgttctggt cactcaagac tcacccctg    780
tggagactgt ggaagaaaat ctgggcagtg cccagtcccg agcgcttttt catgcctctg    840
tataagggc gctccggaga ctttaagaaa tgggtcggag cccccttcac cggatcgagc    900
ctcgagctgg gcccctggtc ccccgaagtg ccttcgcac tggaggtgta cagctgccac    960
ccgccaagaa gccccgctaa gcgcctgcag ctgaccgagc tgcaggaacc agccgaactg   1020
gtcgagtcag acggcgtgcc aaagccatcc ttctggccca ccgcccaaaa ctcgggtgga   1080
agcgcatact ccgaagagag ggacaggcg tacggactcg tgtccatcga taccgtgacc   1140
gtgctggacg ctgagggacc gtgcacttgg ccgtgttcgt gcgaggacga cggataccg    1200
gcgctgggatc tggatgctgg tctggagccg tcccggaacc tgcaggaacc agccgaactg   1260
gccgggacca ccgtgctgtc gtgcggatgc gtgtccgccg gtcccctgg tctgggcggg   1320
cctcttggtt ccctcctgga ccggcttaag ccccgctggg ctgacggaga ggactgggcc   1380
ggggactgc cttgggcgg acgctcacct ggggagtgt cggaatccga agccggctcc    1440
cctttggccg gactggacat ggacacattc gatagcggtt tcgtgggatc cgactgttct   1500
agcccgtgg agtgcgattt cacctccccg ggcgacgagg gtccgccgag atcctacttg   1560
cgccaatggg tggtcattcc ccctccactg tcctccccg ggcacaggc gtcttga       1617

SEQ ID NO: 93        moltype = DNA   length = 1617
FEATURE              Location/Qualifiers
misc_feature         1..1617
                     note = Synthetic sequence
source               1..1617
                     mol_type = other DNA
                     organism = synthetic construct
SEQUENCE: 93
```

```
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaca cctgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccacctt tcaacgtcac cgtgactttt agcggacagt acaacatctc ctggcggagc   420
gactacgagg atccggcctt ctacatgctg aagggaaagc tgcagtacga actgcagtat   480
aggaatcgcg gggaccgtg ggctgtctcc cctcggcgga agctgatttc cgtggattcg   540
agatccgtgt ccctgctccc actggaattc agaaaagatt cgtcctacga actccaagtc   600
cgcgcaggac ccatgcctgg aagctctac cagggaacct ggtccgagtg gtcggatccc   660
gtgatcttcc aaaacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttaagaaa tgggtcggag ccccttcac cggatcgagc   900
ctcgagctgg gccctggtc ccccgaagtg ccttcgaccc tggaggtgta cagctgccac   960
ccgcaagaa gccccgctaa cgcctgcag ctgaccgagc tgcaggaacc agccgaactg  1020
gtcgagtcag acggcgtgcc aaagccatcc ttctggccca ccgccaaaa ctcgggtgga  1080
agcgcatact ccgaagagag ggacaggcc tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtccctggt ctgggcgggg  1320
cctcttggtt ccctcctgga ccggcttaag ccccgctgg ctgacggaga ggactgggcc  1380
gggggactgc cttggggcgg acgctcacct ggggagtgt cggaatccga agccggctcc  1440
cctttggccg gactggacat ggacacattc gatagcggtt cgtgggatc cgactgttct  1500
agccccgtgg agtgcgattt cacctcccg ggcgacgagg tccgccgag atcctacttg  1560
cgccaatggg tggtcattcc ccctccactg tcctccccgg ggcacaggc gtcttga     1617
```

SEQ ID NO: 94                moltype = DNA   length = 1617
FEATURE                      Location/Qualifiers
misc_feature           1..1617
                            note = Synthetic sequence
source                       1..1617
                            mol_type = other DNA
                            organism = synthetic construct
SEQUENCE: 94

```
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaga actgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccacctt tcaacgtcac cgtgactttt agcggacagt acaacatctc ctggcggagc   420
gactacgagg atccggcctt ctacatgctg aagggaaagc tgcagtacga actgcagtat   480
aggaatcgcg gggaccgtg ggctgtctcc cctcggcgga agctgatttc cgtggattcg   540
agatccgtgt ccctgctccc actggaattc agaaaagatt cgtcctacga actccaagtc   600
cgcgcaggac ccatgcctgg aagcttctac cagggaacct ggtccgagtg gtcggatccc   660
gtgatcttcc aaaacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttaagaaa tgggtcggag ccccttcac cggatcgagc   900
ctcgagctgg gccctggtc ccccgaagtg ccttcgaccc tggaggtgta cagctgccac   960
ccgcaagaa gccccgctaa cgcctgcag ctgaccgagc tgcaggaacc agccgaactg  1020
gtcgagtcag acggcgtgcc aaagccatcc ttctggccca ccgccaaaa ctcgggtgga  1080
agcgcatact ccgaagagag ggacaggcc tacggactcg tgtccatcga taccgtgacc  1140
gtgctggacg ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg gtccctggt ctgggcgggg  1320
cctcttggtt ccctcctgga ccggcttaag ccccgctgg ctgacggaga ggactgggcc  1380
gggggactgc cttggggcgg acgctcacct ggggagtgt cggaatccga agccggctcc  1440
cctttggccg gactggacat ggacacattc gatagcggtt cgtgggatc cgactgttct  1500
agccccgtgg agtgcgattt cacctcccg ggcgacgagg tccgccgag atcctacttg  1560
cgccaatggg tggtcattcc ccctccactg tcctccccgg ggcacaggc gtcttga     1617
```

SEQ ID NO: 95                moltype = AA   length = 538
FEATURE                        Location/Qualifiers
REGION                       1..538
                            note = Synthetic sequence
source                       1..538
                            mol_type = protein
                            organism = synthetic construct
SEQUENCE: 95

```
MPRGWAAPLL LLLLQGGWGC PDLVCYTDYL QTVICILEMW NLHPSTLTLT WQDQYETLKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
```

```
AGTTVLSCGC VSAGSPGLGG PLGSLLDRLK PPLADGEDWA GGLPWGGRSP GGVSESEAGS    480
PLAGLDMDTF DSGFVGSDCS SPVECDFTSP GDEGPPRSYL RQWVVIPPPL SSPGPQAS     538

SEQ ID NO: 96              moltype = AA  length = 538
FEATURE                    Location/Qualifiers
REGION                     1..538
                           note = Synthetic sequence
source                     1..538
                           mol_type = protein
                           organism = synthetic construct
SEQUENCE: 96
MPRGWAAPLL LLLLQGGWGC PDLVCYTDYL QTVICILEMW NLHPSTLTLT WQDQYEHLKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 97              moltype = AA  length = 538
FEATURE                    Location/Qualifiers
REGION                     1..538
                           note = Synthetic sequence
source                     1..538
                           mol_type = protein
                           organism = synthetic construct
SEQUENCE: 97
MPRGWAAPLL LLLLQGGWGC PDLVCYTDYL QTVICILEMW NLHPSTLTLT WQDQYETLKD    60
EATSCSLHRS AHNATHATYT CHMDVFHFIA DEIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 98              moltype = AA  length = 538
FEATURE                    Location/Qualifiers
REGION                     1..538
                           note = Synthetic sequence
source                     1..538
                           mol_type = protein
                           organism = synthetic construct
SEQUENCE: 98
MPRGWAAPLL LLLLQGGWGC PDLVCYTDYL QTVICILEMW NLHPSTLTLT WQDQYEHLKD    60
EATSCSLHRS AHNATHATYT CHMDVFHFIA DEIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 99              moltype = AA  length = 538
FEATURE                    Location/Qualifiers
REGION                     1..538
                           note = Synthetic sequence
source                     1..538
                           mol_type = protein
                           organism = synthetic construct
SEQUENCE: 99
MPRGWAAPLL LLLLQGGWGC PDLVCYTDYL QTVICILEMW NLHPSTLTLT WQDQYETLKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538

SEQ ID NO: 100             moltype = AA  length = 538
FEATURE                    Location/Qualifiers
REGION                     1..538
                           note = Synthetic sequence
```

| source | 1..538 |
| --- | --- |
| | mol_type = protein |
| | organism = synthetic construct |

SEQUENCE: 100

```
MPRGWAAPLL LLLLQGGWGC PDLVCYTDYL QTVICILEMW NLHPSTLTLT WQDQYEHLKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538
```

| SEQ ID NO: 101 | moltype = AA   length = 538 |
| --- | --- |
| FEATURE | Location/Qualifiers |
| REGION | 1..538 |
| | note = Synthetic sequence |
| source | 1..538 |
| | mol_type = protein |
| | organism = synthetic construct |

SEQUENCE: 101

```
MPRGWAAPLL LLLLQGGWGC PDLVCYTDYL QTVICILEMW NLHPSTLTLT WQDQYEELKD    60
EATSCSLHRS AHNATHATYT CHMDVFHFIA DEIFSVNITD QSGNYSQECG SFLLAESIKP   120
APPFNVTVTF SGQYNISWRS DYEDPMFYML KGKLQYELQY RNRGDPWAVS PRRKLISVDS   180
RSVSLLPLEF RKDSSYELQV RAGPMPGSFY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS    538
```

| SEQ ID NO: 102 | moltype = DNA   length = 1617 |
| --- | --- |
| FEATURE | Location/Qualifiers |
| misc_feature | 1..1617 |
| | note = Synthetic sequence |
| source | 1..1617 |
| | mol_type = other DNA |
| | organism = synthetic construct |

SEQUENCE: 102

```
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaac gctgaaggac   180
gaagccacct cctgttcact gcaccgctcc gcgcacaacg cgactcacgc gacctacact   240
tgccacatgg acgtgttcca cttcatcgcc gacgagatct ctccgtgaa catcactgac   300
cagtcgggga actactccca agagtgcgga agctttcttc tggccgagag catcaagccc   360
gctccacctt tcaacgtcac cgtgactttt agcggacagt acaacatctc ctggcggagc   420
gactacgagg atccgatgtt ctacatgctg aagggaaagc tgcagtacga actgcagtat   480
aggaatcgcg gggaccgtgg ggctgtctcc cctcggcgga agctgatttc cgtggattcg   540
agatccgtgt ccctgctccc actggaattc agaaaagatt cgtcctacga actccaagtc   600
cgcgcaggac ccatgcctgg aagcttctac cagggaacct ggtccgagtg gtcggatccc   660
gtgatcttcc aaacacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttttaagaa tgggtcggag cccccttgc cggatcgagc   900
ctcgagctgg gccccctggtc ccccgaagtg ccttcgaccc tggaggtgta cagctgccac   960
ccgcaagaa gccccgctaa gcgcctcag ctgaccgagc tgcaggaacc agccgaactg   1020
gtcgagtcag acggcgtgcc aaagccatcc ttctggccca ccgccaaaaa ctcgggtgga  1080
agcgcatact ccgaagagag ggacaggccg tacggactcg tgtccatcga taccgtgacc  1140
gtgctggacg ctgagggacc gtgcacttgg ccgtgttcgt gcgaggacga cggataccgg  1200
gcgctggatc tggatgctgg tctgagccgc tccccgggac tggaagatcc gctgctggac  1260
gccgggacca ccgtgctgtc gtgcggatgc gtgtccgccg gtcccctggg tctgggcggg  1320
cctcttggtt ccctcctgga ccggcttaag ccccgctgg ctgacggaga ggactgggcc  1380
gggggactgc cttgggcggn acgctcacct ggggagtgt cggaatccga agccggctcc  1440
cctttggccg gactgacat ggacacattc gatagcggtt tcgtgggatc cgactgttct  1500
agccccgtgg agtgcgattt cacctccccg ggcgacgagg tcgccgag atcctacttg  1560
cgccaatggg tggtcattcc ccctccactg tcctccccgg ggcccacagg cgtcttga    1617
```

| SEQ ID NO: 103 | moltype = DNA   length = 1617 |
| --- | --- |
| FEATURE | Location/Qualifiers |
| misc_feature | 1..1617 |
| | note = Synthetic sequence |
| source | 1..1617 |
| | mol_type = other DNA |
| | organism = synthetic construct |

SEQUENCE: 103

```
atgccgcgtg gctgggccgc ccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaca cctgaaggac   180
```

| | |
|---|---|
| gaagccacct cctgttcact gcaccgctcc gcgcacaacg cgactcacgc gacctacact | 240 |
| tgccacatgg acgtgttcca cttcatcgcc gacgagatct tctccgtgaa catcactgac | 300 |
| cagtcgggga actactccca agagtgcgga agctttcttc tggccgagag catcaagccc | 360 |
| gctccacctt tcaacgtcac cgtgactttt agcggacagt acaacatctc ctggcggagc | 420 |
| gactacgagg atccgatgtt ctacatgctg aagggaaaac tgcagtacga actgcagtat | 480 |
| aggaatcgcg gggacccgtg ggctgtctcc cctcggcgga agctgatttc cgtggattcc | 540 |
| agatccgtgt ccctgctccc actggaattc agaaaagatt cgtcctacga actccaagtc | 600 |
| cgcgcaggac ccatgcctgg aagcttctac cagggaacct ggtccgagtg gtcggatccc | 660 |
| gtgatcttcc aaaacacagtc cgaagaattg aaggagggct ggaatcccca tctgctgctc | 720 |
| ctcctgttgc tggtcatcgt gttcattccg gcgttctggt cactcaagac tcaccctctg | 780 |
| tggagactgt ggaagaaaat ctgggcagtg cccagtcccg agcgcttttt catgcctctg | 840 |
| tataagggct gctccggaga ctttaagaaa tgggtcggag ccccttcac cggatcgagc | 900 |
| ctcgagctgg cccctggtc cccgaagtg ccttcgaccc tggaggtgta cagctgccac | 960 |
| ccgccaagaa gccccgctaa gcgcctgcag ctgaccgagc tgcaggaacc agccgaactg | 1020 |
| gtcgagtcag acggcgtgcc aaagccatcc ttctggccca ccgcccaaaa ctcgggtgga | 1080 |
| agcgcatact ccgaagagag ggacaggccg tacggactcg tgtccatcga taccgtgacc | 1140 |
| gtgctggacg ctgagggacc gtgcacttgg ccgtgttcgt gcgaggacga cggatacccg | 1200 |
| gcgctggatc tggatgctgg tctgagccg tccccgggac tggaagatcc gctgctggac | 1260 |
| gccgggacca ccgtgctgtc gtgcggatgc gtgtccgccg gtccccctgg tctgggcggg | 1320 |
| cctcttggtt ccctcctgga ccggcttaag ccccgctgg ctgacggaga ggactgggcc | 1380 |
| gggggactgc cttgggggcg acgctcacct ggggagtgt cggaatccga agccggctcc | 1440 |
| cctttggccg gactggacat ggacacattc gatagcggtt tcgtgggatc cgactgttct | 1500 |
| agccccgtgg agtgcgattt cacctccccg ggcgacgagg tccgccgag atcctacttg | 1560 |
| cgccaatggg tggtcattcc ccctccactg tcctccccgg ggccacaggc gtcttga | 1617 |

```
SEQ ID NO: 104         moltype = DNA   length = 1617
FEATURE                Location/Qualifiers
misc_feature           1..1617
                       note = Synthetic sequence
source                 1..1617
                       mol_type = other DNA
                       organism = synthetic construct
SEQUENCE: 104
```

| | |
|---|---|
| atgccgcgtg gctgggccgc ccccttgctc ctgctgctgc tccagggagg ctggggctgt | 60 |
| cctgaccttg tgtgctacac cgactatctg caaaccgtga tttgcattct cgagatgtgg | 120 |
| aacctccatc cgtcaaccct gaccctgacg tggcaggacc agtacgaaac gctgaaggac | 180 |
| gaagccacct cctgttcact gcaccgctcc gcgcacaacg cgactcacgc gacctacact | 240 |
| tgccacatgg acgtgttcca cttcatcgcc gacgagatct tctccgtgaa catcactgac | 300 |
| cagtcgggga actactccca agagtgcgga agctttcttc tggccgagag catcaagccc | 360 |
| gctccacctt tcaacgtcac cgtgactttt agcggacagt acaacatctc ctggcggagc | 420 |
| gactacgagg atccggcctt ctacatgctg aagggaaagc tgcagtacga actgcagtat | 480 |
| aggaatcgcg gggacccgtg ggctgtctcc cctcggcgga agctgatttc cgtggattcg | 540 |
| agatccgtgt ccctgctccc actggaattc agaaaagatt cgtcctacga actccaagtc | 600 |
| cgcgcaggac ccatgcctgg aagcttctac cagggaacct ggtccgagtg gtcggatccc | 660 |
| gtgatcttcc aaaacacagtc cgaagaattg aaggagggct ggaatcccca tctgctgctc | 720 |
| ctcctgttgc tggtcatcgt gttcattccg gcgttctggt cactcaagac tcaccctctg | 780 |
| tggagactgt ggaagaaaat ctgggcagtg cccagtcccg agcgcttttt catgcctctg | 840 |
| tataagggct gctccggaga ctttaagaaa tgggtcggag ccccttcac cggatcgagc | 900 |
| ctcgagctgg cccctggtc cccgaagtg ccttcgaccc tggaggtgta cagctgccac | 960 |
| ccgccaagaa gccccgctaa gcgcctgcag ctgaccgagc tgcaggaacc agccgaactg | 1020 |
| gtcgagtcag acggcgtgcc aaagccatcc ttctggccca ccgcccaaaa ctcgggtgga | 1080 |
| agcgcatact ccgaagagag ggacaggccg tacggactcg tgtccatcga taccgtgacc | 1140 |
| gtgctggacg ctgagggacc gtgcacttgg ccgtgttcgt gcgaggacga cggatacccg | 1200 |
| gcgctggatc tggatgctgg tctgagccg tccccgggac tggaagatcc gctgctggac | 1260 |
| gccgggacca ccgtgctgtc gtgcggatgc gtgtccgccg gtccccctgg tctgggcggg | 1320 |
| cctcttggtt ccctcctgga ccggcttaag ccccgctgg ctgacggaga ggactgggcc | 1380 |
| gggggactgc cttgggggcg acgctcacct ggggagtgt cggaatccga agccggctcc | 1440 |
| cctttggccg gactggacat ggacacattc gatagcggtt tcgtgggatc cgactgttct | 1500 |
| agccccgtgg agtgcgattt cacctccccg ggcgacgagg tccgccgag atcctacttg | 1560 |
| cgccaatggg tggtcattcc ccctccactg tcctccccgg ggccacaggc gtcttga | 1617 |

```
SEQ ID NO: 105         moltype = DNA   length = 1617
FEATURE                Location/Qualifiers
misc_feature           1..1617
                       note = Synthetic sequence
source                 1..1617
                       mol_type = other DNA
                       organism = synthetic construct
SEQUENCE: 105
```

| | |
|---|---|
| atgccgcgtg gctgggccgc ccccttgctc ctgctgctgc tccagggagg ctggggctgt | 60 |
| cctgaccttg tgtgctacac cgactatctg caaaccgtga tttgcattct cgagatgtgg | 120 |
| aacctccatc cgtcaaccct gaccctgacg tggcaggacc agtacgaaac cctgaaggac | 180 |
| gaagccacct cctgttcact gcaccgctcc gcgcacaacg cgactcacgc gacctacact | 240 |
| tgccacatgg acgtgttcca cttcatcgcc gacgagatct tctccgtgaa catcactgac | 300 |
| cagtcgggga actactccca agagtgcgga agctttcttc tggccgagag catcaagccc | 360 |
| gctccacctt tcaacgtcac cgtgactttt agcggacagt acaacatctc ctggcggagc | 420 |
| gactacgagg atccggcctt ctacatgctg aaggaaagc tgcagtacga actgcagtat | 480 |
| aggaatcgcg gggacccgtg ggctgtctcc cctcggcgga agctgatttc cgtggattcg | 540 |
| agatccgtgt ccctgctccc actggaattc agaaaagatt cgtcctacga actccaagtc | 600 |

```
cgcgcaggac ccatgcctgg aagcttctac cagggaacct ggtccgagtg gtcggatccc    660
gtgatcttcc aaaacacagtc cgaagaattg aaggagggct ggaatcccca tctgctgctc    720
ctcctgttgc tggtcatcgt gttcattccg gcgttctggt cactcaagac tcaccctctg    780
tggagactgt ggaagaaaat ctgggcagtg cccagtcccg agcgcttttt catgcctctg    840
tataagggct gctccggaga cttttaagaaa tgggtcggag ccccctttcac cggatcgagc    900
ctcgagctgg gccccctggtc ccccgaagtg ccttcgaccc tggaggtgta cagctgccac    960
ccgccaagaa gccccgctaa gcgcctgcag ctgaccgagc tgcaggaacc agccgaactg   1020
gtcgagtcag acggcgtgcc aaagccatcc ttctggccca ccgcccaaaa ctcgggtgga   1080
agcgcatact ccgaagagag ggacaggccg tacggactcg tgtccatcga taccgtgacc   1140
gtgctggacg ctgagggacc gtgcacttgg ccgtgttcgt gcgaggacga cggatacccg   1200
gcgctggatc tggatgctgg tctgagccgt ccccgggac tggaagatcc gctgctggac   1260
gccgggacca ccgtgctgtc gtgcggatgc gtgtccgccg gtccctgg tctgggcggg   1320
cctcttggtt ccctcctgga ccggcttaag ccccgctgg ctgacggaga ggactgggcc   1380
gggggactgc cttggggcgg acgctcacct ggggagtgt cggaatccga agccggctcc   1440
cctttggccg gactgacat ggacacattc gatagcggtt tcgtgggatc cgactgttct   1500
agcccgtgg agtgcgattt cacctccccg ggcgacgagg tccgccgag atcctacttg   1560
cgccaatggg tggtcattcc ccctccactg tcctccccgg ggccacaggc gtcttga      1617

SEQ ID NO: 106           moltype = DNA   length = 1617
FEATURE                  Location/Qualifiers
misc_feature             1..1617
                         note = Synthetic sequence
source                   1..1617
                         mol_type = other DNA
                         organism = synthetic construct
SEQUENCE: 106
atgccgcgtg gctgggccgc cccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaac gctgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccaccctt tcaacgtcac cgtgactttt agcggacagt acaacatcttc ctggcggagc   420
gactacgagg atccgatgtt ctacatgctg aagggaaagc tgcagtacga actgcagtat   480
aggaatcgcg ggaccgtg gctgtctcc cctcggcgga agctgatttc cgtggattcg   540
agatccgtgt ccctgctccc actggaattc agaaaagatt cgtcctacga actccaagtc   600
cgcgcaggac ccatgcctgg aagctcatac cagggaacct ggtccgagtg gtcggatccc   660
gtgatcttcc aaaacacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttttaagaaa tgggtcggag ccccctttcac cggatcgagc   900
ctcgagctgg gccccctggtc ccccgaagtg ccttcgaccc tggaggtgta cagctgccac   960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
agcgcatact ccgaagagag ggacaggccg tacggactcg tgtccatcga taccgtgacc  1140
gtgctggacg ctgagggacc gtgcacttgg ccgtgttcgt gcgaggacga cggatacccg  1200
gcgctggatc tggatgctgg tctgagccgt ccccgggac tggaagatcc gctgctggac  1260
gccgggacca ccgtgctgtc gtgcggatgc gtgtccgccg gtccctgg tctgggcggg  1320
cctcttggtt ccctcctgga ccggcttaag ccccgctgg ctgacggaga ggactgggcc  1380
gggggactgc cttggggcgg acgctcacct ggggagtgt cggaatccga agccggctcc  1440
cctttggccg gactgacat ggacacattc gatagcggtt tcgtgggatc cgactgttct  1500
agcccgtgg agtgcgattt cacctccccg ggcgacgagg tccgccgag atcctacttg  1560
cgccaatggg tggtcattcc ccctccactg tcctccccgg ggccacaggc gtcttga     1617

SEQ ID NO: 107           moltype = DNA   length = 1617
FEATURE                  Location/Qualifiers
misc_feature             1..1617
                         note = Synthetic sequence
source                   1..1617
                         mol_type = other DNA
                         organism = synthetic construct
SEQUENCE: 107
atgccgcgtg gctgggccgc cccccttgctc ctgctgctgc tccagggagg ctggggctgt    60
cctgaccttg tgtgctacac cgactatctg caaaccgtga tttgcattct cgagatgtgg   120
aacctccatc cgtcaaccct gaccctgacg tggcaggacc agtacgaaac cctgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccaccctt tcaacgtcac cgtgactttt agcggacagt acaacatcttc ctggcggagc   420
gactacgagg atccgatgtt ctacatgctg aagggaaagc tgcagtacga actgcagtat   480
aggaatcgcg ggaccgtg gctgtctcc cctcggcgga agctgatttc cgtggattcg   540
agatccgtgt ccctgctccc actggaattc agaaaagatt cgtcctacga actccaagtc   600
cgcgcaggac ccatgcctgg aagctcatac cagggaacct ggtccgagtg gtcggatccc   660
gtgatcttcc aaaacacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga cttttaagaaa tgggtcggag ccccctttcac cggatcgagc   900
ctcgagctgg gccccctggtc ccccgaagtg ccttcgaccc tggaggtgta cagctgccac   960
ccgccaagaa gccccgctaa gcgcctgcag ctgaccgagc tgcaggaacc agccgaactg  1020
```

```
gtcgagtcag acggcgtgcc aaagccatcc ttctggccca ccgcccaaaa ctcgggtgga   1080
agcgcatact ccgaagagag ggacaggccg tacggactcg tgtccatcga taccgtgacc   1140
gtgctgacg  ctgagggacc gtgcacttgg ccgtgttcgt gcgaggacga cggatacccg   1200
gcgctggatc tggatgctgg tctggagccg tccccgggac tggaagatcc gctgctggac   1260
gccgggacca ccgtgctgtc gtgcggatgc gtgtccgccg ggtcccctgg tctgggcggg   1320
cctcttggtt ccctcctgga ccggcttaag ccccgctgg  ctgacggaga ggactgggcc   1380
ggggactgc  cttggggcgg acgctcacct gggggagtgt cggaatccga agccggctcc   1440
cctttggccg gactggacat ggacacattc gatagcggtt tcgtgggatc cgactgttct   1500
agccccgtgg agtgcgattt cacctccccg ggcgacgagg gtccgccgag atcctacttg   1560
cgccaatggg tggtcattcc ccctccactg tcctccccgg ggccacaggc gtcttga      1617

SEQ ID NO: 108           moltype = DNA   length = 1617
FEATURE                  Location/Qualifiers
misc_feature             1..1617
                         note = Synthetic sequence
source                   1..1617
                         mol_type = other DNA
                         organism = synthetic construct
SEQUENCE: 108
atgccgcgtg gctgggccgc ccccttgctc ctgctgctgc tccagggagg ctggggctgt   60
cctgaccttg tgtgctacac cgactatctg caaaccgtga tttgcattct cgagatgtgg   120
aacctccatc cgtcaaccct gacctgacg  tggcaggacc agtacgaaga actgaaggac   180
gaagccacct cctgttcact gcaccgctcc gcgcacaacg cgactcacgc gacctacact   240
tgccacatgg acgtgttcca cttcatcgcc gacgagatct tctccgtgaa catcactgac   300
cagtcgggga actactccca agagtgcgga agctttcttc tggccgagag catcaagccc   360
gctccacctt tcaacgtcac cgtgactttt agccgacagt acaacatctc ctggcggagc   420
gactacgagg atccgatgtt ctacatgctg aagggaaagc tgcagtacga actgcagtat   480
aggaatcgcg gggaccgtg  ggctgtctcc cctcggcgga agctgatttc cgtggattcg   540
agatccgtgt ccctgctccc actggaattc agaaaagatt cgtcctacga actccaagtc   600
cgcgcaggac ccatgcctgg aagcttctac cagggaacct ggtccgagtg gtcggatccc   660
gtgatcttcc aaacacagtc cgaagaattg aaggagggct ggaatcccca tctgctgctc   720
ctcctgttgc tggtcatcgt gttcattccg gcgttctggt cactcaagac tcaccctctg   780
tggagactgt ggaagaaaat ctgggcagtg cccagtcccg agcgcttttt catgcctctg   840
tataagggct gctccggaga ctttaagaaa tgggtcggag ccccccttcac cggatcgagc   900
ctcgagctgg gccccttggtc ccccgaagtg ccttcgaccc tggaggtgta cagctgccac   960
ccgccaagaa gccccgctaa gcgcctgcag ctgaccgagc tgcaggaacc agccgaactg  1020
gtcgagtcag acggcgtgcc aaagccatcc ttctggccca ccgcccaaaa ctcgggtgga  1080
agcgcatact ccgaagagag ggacaggccg tacggactcg tgtccatcga taccgtgacc  1140
gtgctgacg  ctgagggacc gtgcacttgg ccgtgttcgt gcgaggacga cggatacccg  1200
gcgctggatc tggatgctgg tctggagccg tccccgggac tggaagatcc gctgctggac  1260
gccgggacca ccgtgctgtc gtgcggatgc gtgtccgccg ggtcccctgg tctgggcggg  1320
cctcttggtt ccctcctgga ccggcttaag ccccgctgg  ctgacggaga ggactgggcc  1380
ggggactgc  cttggggcgg acgctcacct gggggagtgt cggaatccga agccggctcc  1440
cctttggccg gactggacat ggacacattc gatagcggtt tcgtgggatc cgactgttct  1500
agccccgtgg agtgcgattt cacctccccg ggcgacgagg gtccgccgag atcctacttg  1560
cgccaatggg tggtcattcc ccctccactg tcctccccgg ggccacaggc gtcttga     1617
```